US007981659B2

(12) United States Patent
Kadoya et al.

(10) Patent No.: US 7,981,659 B2
(45) Date of Patent: Jul. 19, 2011

(54) BACILLUS SUBTILIS MUTANT STRAIN

(75) Inventors: Ryosuke Kadoya, Nara (JP); Keiji Endo, Tochigi (JP); Masatoshi Tohata, Tochigi (JP); Katsutoshi Ara, Tochigi (JP); Naotake Ogasawara, Nara (JP)

(73) Assignees: Kao Corporation, Tokyo (JP); Nara Institute of Science and Technology, Nara (JP)

( * ) Notice: Subject to any disclaimer, the term of this patent is extended or adjusted under 35 U.S.C. 154(b) by 34 days.

(21) Appl. No.: 12/083,539

(22) PCT Filed: Sep. 25, 2006

(86) PCT No.: PCT/JP2006/318986
§ 371 (c)(1),
(2), (4) Date: Nov. 4, 2008

(87) PCT Pub. No.: WO2007/043327
PCT Pub. Date: Apr. 19, 2007

(65) Prior Publication Data
US 2009/0221055 A1    Sep. 3, 2009

(30) Foreign Application Priority Data

Oct. 13, 2005  (JP) .................................. 2005-298406

(51) Int. Cl.
*C12N 1/20*  (2006.01)
(52) U.S. Cl. ................................. 435/252.31; 435/252.3
(58) Field of Classification Search .................. None
See application file for complete search history.

(56) References Cited

U.S. PATENT DOCUMENTS

| 4,450,235 A | 5/1984 | Dean et al. |
| 5,874,278 A | 2/1999 | Sloma et al. |
| 5,958,728 A | 9/1999 | Sloma et al. |
| 6,451,560 B1 | 9/2002 | Harwood et al. |

FOREIGN PATENT DOCUMENTS

| EP | 0 164 117 A2 | 12/1985 |
| JP | 58-190390 A | 11/1983 |
| JP | 61-001381 A | 1/1986 |
| JP | 4-190793 A | 7/1992 |
| JP | 11-509096 A | 8/1999 |
| JP | 2000-210081 A | 8/2000 |
| JP | 2001-503641 A | 3/2001 |
| JP | 3210315 B2 | 9/2001 |
| JP | 2001-527401 A | 12/2001 |
| JP | 2002-520017 A | 7/2002 |
| JP | 2004/313169 A | 11/2004 |
| JP | 2005/348641 A | 12/2005 |
| WO | WO 89/04866 | 6/1989 |
| WO | WO 97/03185 | 1/1997 |
| WO | WO 98-49328 | 11/1998 |
| WO | WO 03/083125 A1 | 10/2003 |

OTHER PUBLICATIONS

Morimoto, T., et al., "Enhanced Recombinant Protein Productivity by Genome Reduction in *Bacillus subtilis*," *DNA Research* 15:73-81, Oxford Univ. Press (Apr. 2008).

Ye, R. et al., "High-Level Secretory Production of Intact, Biologically Active Staphylokinase from *Bacillus subtilis*," *Biotechnol. Bioeng.* 62:87-96, John Wiley & Sons, Inc. (Jan. 1999).
Extended European Search Report for EPO Application No. 06798311.4-2406, European Patent Office, Munich, Germany, mailed on Dec. 15, 2008.
Akamastsu, T., et al., "Incorporation of the Whole Chromosomal DNA in Protoplast Lysates into Competent Cells of *Bascillus subtilis*," *Biosci. Biotechnol. Biochem.* 65:823-829, Japan Society for Bioscience, Biotechnology, and Agrochemistry (2001).
New Energy and Industrial Technology Development Organization, Development of Fundamental Technology for Production Process Using Biofunction (Development of Technology for Creation and Production of Host Cells) Accomplishment Report, pp. 35-72, Japan Bioindustry Association (in Japanese) (Mar. 2003).
Kunst, F., et al., "The complete genome sequence of the Gram-positive bacterium *Bacillus subtilis*," *Nature* 390:249-256, Nature Publishing Group (1997).
New Energy and Industrial Technology Development Organization, Development of Fundamental Technology for Production Process Using Biofunction (Development of Technology for Creation and Production of Host Cells) Accomplishment Report, Japan Bioindustry Association (Mar. 2003) (partial English Translation of document NPL2, corresponding to pp. 48, line 16 to p. 50, line 2 and p. 56, line 2 to p. 61, line 14).
Esp@cenet Database, English language abstract for JP 2004/313169 A (listed as document FP2 on the accompanying form PTO/SB/08A).
Esp@cenet Database, English language abstract for JP 2005/348641 A (listed as document FP3 on the accompanying form PTO/SB/08A).
International Search Report for International Application No. PCT/JP2006/318986, Japanese Patent Office, Japan, mailed on Dec. 26, 2006.
Written Opinion of the International Searching Authority for International Application No. PCT/JP2006/318986, mailed Dec. 26, 2006.
Written Opinion of the International Searching Authority for International Application No. PCT/JP2006/318986 (English language translation of NPL8).
Akamatsu, T. et al., "Characterization of chromosome and plasmid transformation in *Bacillus subtilis* using gently lysed protoplasts," *Arch Microbiol* 146(4): 353-357 (Jan. 1987), Springer-Verlag, Heidelberg, Germany.
Akamatsu, T. et al., "Incorporation of the whole chromosomal DNA in protoplast lysates into competent cells of *Bacillus subtilis*," *Biosci Biotechnol Biochem* 65(4): 823-829 (Apr. 2001), Japan Soc. Biosci, Biotech and Agrochem., Tokyo, Japan.
Hagihara, H. et al., "Novel χ-Amylase That Is Highly Resistant to Chelating Reagents and Chemical Oxidants from the Alkaliphilic *Bacillus* Isolate KSM-K38," *Appl. Envir. Microbiol.* 67: 1744-1750 (Apr. 2001), Am. Soc. Microbiology, Washington, DC.

(Continued)

*Primary Examiner* — Patricia A Duffy
(74) *Attorney, Agent, or Firm* — Sterne, Kessler, Goldstein & Fox P.L.L.C.

(57) ABSTRACT

Novel *Bacillus subtilis* mutant strains having good productivity of various enzymes are provided through extensive analysis of strains that are derived from *Bacillus subtilis* via gene disruption. The *Bacillus subtilis* mutant strains according to the present invention have genomic structures prepared by deletion of regions listed in the columns for deficient regions. Each of these *Bacillus subtilis* mutant strains exerts significantly improved secretory productivity of a protein when a gene encoding such a secretory target protein is introduced so that it can be expressed, compared with a case in which the same gene is introduced into a wild-type strain.

6 Claims, 8 Drawing Sheets

OTHER PUBLICATIONS

Henrissat, B., "A classification of glycosyl hydrolases based on amino acid sequence similarities," Biochem. J. 280: 309-316 (Dec. 1991), Portland Press, UK.

Hoch, J.A., et al., "Transformation and Transduction in Recombination-defective Mutants of *Bacillus subtilis*," J. Bacteriol. 93: 1925-1937 (Jun. 1967) Am. Soc. Microbiology, Washington, DC.

Horton, R.M. et al., "Engineering hybrid genes without the use of restriction enzymes: gene splicing by overlap extension," Gene 77(1): 61-68 (Apr. 1989), Elsevier Science Publishers, B.V., Amsterdam, The Netherlands.

Kobayashi, K. et al., "Essential *Bacillus subtilis* genes," Proc. Natl. Acad. Sci. USA 100: 4678-4683 (Apr. 2003), National Academy of Sciences, Washington, DC.

Kobayashi, T., et al., "Purification and properties of an alkaline protease from alkalophilic *Bacillus* sp. KSM-K16," Appl Microbiol Biotechnol 43(3): 473-481 (Jul. 1995), Springer-Verlag, Heidelberg, Germany.

Moriya, S. et al., "Cloning of an autonomously replicating sequence (ars) from the *Bacillus subtilis* chromosome," Mol Microbiol 6(3): 309-315 (Feb. 1992), Blackwell Scientific Publications Ltd., Oxford, UK.

Vagner, V. et al., "A vector for systematic gene inactivation in *Bacillus subtilis*," Microbiology 144: 3097-3104 (Nov. 1998), Soc. Gen. Microbiology, Reading, UK.

Dialog File 351, World Patents Index Accession No. 2761208, English language abstract and patent family for JP 58-190390 A, published Nov. 7, 1983.

Dialog File 351, World Patents Index Accession No. 3532683, English language abstract and patent family for JP 61-001381 A, published Jan. 7, 1986.

Dialog File 351, World Patents Index Accession No. 8025562, English language abstract and patent family for JP 11-059096 A, published Aug. 17, 1999.

Dialog File 351, World Patents Index Accession No. 5167714, English language abstract and patent family for JP 3210315 B2, published Sep. 17, 2001.

Dialog File 351, World Patents Index Accession No. 9104877, English language abstract and patent family for JP 2001-527401 A, published Dec. 25, 2001.

Dialog File 351, World Patents Index Accession No. 9875015, English language abstract and patent family for JP 2002-520017 A, published Jul. 9, 2002.

Dialog File 351, World Patents Index Accession No. 8769198, English language abstract and patent family for JP 2001-503641 A, published Mar. 21, 2001.

Dialog File 351, World Patents Index Accession No. 10283227, English language abstract and patent family for JP 2000-210081 A, published Aug. 2, 2000.

Dialog File 351, World Patents Index Accession No. 6043451, English language abstract and patent family for JP 4-190793 A, published Jul. 9, 1992.

BACILLUS SUBTILIS MUTANT STRAIN

TECHNICAL FIELD

The present invention relates to novel *Bacillus subtilis* mutant strains. The present invention particularly relates to novel *Bacillus subtilis* mutant strains having improved secretory productivity of various proteins.

Reference to a sequence listing submitted on compact disc
Pursuant to 37 CFR §§1.825 and 1.52, the sequence listing for this application is provided on compact disc. Disc 1 of 3 is the computer readable form of the substitute sequence listing on a replacement CD-R compact disc, labeled "Replacement Sequence Listing Computer Readable Format Prepared: Jan. 5, 2009." The CD-R compact disc is formatted for IBM-PC/MS-Windows and contains one file: "Substitute Sequence Listing.TXT," created on Jan. 5, 2009, comprising 180,884 bytes. Disc 2 of 3 is labeled "COPY 1 REPLACEMENT Jan. 5, 2009" and is provided on a CD-R compact disc formatted for IBM-PC/MS-Windows and contains one file: "Substitute Sequence Listing.TXT," created on Jan. 5, 2009, comprising 180,884 bytes. Disc 3 of 3 is labeled "COPY 2 REPLACEMENT Jan. 5, 2009" and is provided on a CD-R compact disc formatted for IBM-PC/MS-Windows and contains one file: "Substitute Sequence Listing.TXT," created on Jan. 5, 2009, comprising 180,884 bytes. The entire contents of the compact discs are expressly incorporated herein by reference.

BACKGROUND ART

*Bacillus subtilis* is not only subjected broadly to molecular biological studies as a Gram-positive bacterium model, but it is also used broadly in fermentation-related industries, the pharmaceutical industry, and the like, as a bacterium producing various enzymes such as amylase and protease. The entire nucleotide sequence of *Bacillus subtilis* genome has already been determined by the joint Japanese and European genome project. However, identification of the functions of approximately 4100 types of gene existing in the *Bacillus subtilis* genome has not yet been completed.

Strains having approximately 4100 types of disrupted gene existing in the *Bacillus subtilis* genome have been extensively studied to date. It has thus been suggested that 271 genes are essential for the growth (K. Kobayashi et al., Proc. Natl. Acad. Sci. U.S.A., 100, 4678-4683, 2003).

Furthermore, bacterial strains have each been constructed by deletion or inactivation of a gene involved in early spore formation of *Bacillus subtilis* or the like or a protease gene, a gene involved in D-alanine addition to teichoic acid within cell walls or cell membranes, or a gene involved in biosynthesis or secretion of Surfactin (see JP Patent Publication (Kokai) No. 58-190390 A (1983), JP Patent Publication (Kokai) No. 61-1381 A (1986), International Publication No. 89/04866 Pamphlet, JP Patent Publication (Kohyo) No. 11-509096 A (1999), JP Patent No. 321.0 315, JP Patent Publication (Kohyo) No. 2001-527401 A, JP Patent Publication (Kohyo) No. 2002-520017 A, and JP Patent Publication (Kohyo) No. 2001-503641 A). However, the degrees of improvement in protein productivity of these bacterial strains have been insufficient. Furthermore, no useful findings have been obtained to date concerning *Bacillus subtilis*-derived mutant strains having improved productivity of various proteins, or concerning extensive analysis of the mutant strains.

DISCLOSURE OF THE INVENTION

Object to be Achieved by the Invention

In view of the above circumstances, an object of the present invention is to provide novel *Bacillus subtilis* mutant strains having excellent productivity of various enzymes through the extensive analysis of gene-disrupted strains derived from *Bacillus subtilis*.

Means to Achieve the Object

To achieve the above object, the present inventors have extensively analyzed mutant strains obtained by deletion of large regions of the *Bacillus subtilis* genome, and thus they have succeeded in obtaining many *Bacillus subtilis* mutant strains having excellent productivity of various enzymes. Thus, the invention has been completed.

*Bacillus subtilis* mutant strains according to the present invention have genomic structures prepared by deletion of regions as listed in columns for deficient regions as shown in the following Table 1. Such *Bacillus subtilis* mutant strain is prepared by introducing a gene encoding a target protein so that the protein can be expressed, and the thus obtained *Bacillus subtilis* mutant strain possesses significantly improved secretory productivity of a target protein compared with a case in which the same gene is introduced into a wild-type strain. Moreover, such *Bacillus subtilis* mutant strain may be a mutant strain in which a gene encoding a target protein is introduced so that the gene can be expressed. Furthermore, a gene encoding a target protein may contain a nucleotide sequence that encodes a region corresponding to a secretion signal or may be appropriately ligated to DNA upstream thereof containing a nucleotide sequence that encodes a region corresponding to a secretion signal. Here the above target protein may be at least one enzyme selected from the group consisting of cellulase, protease, and amylase. Furthermore, such a *Bacillus subtilis* mutant strain may be prepared using the *Bacillus subtilis* 168 strain as a wild-type strain. Moreover, genomic regions listed in the columns for deficient regions, as listed in the following Table 1, may contain regions each located between oligonucleotides that form a set as listed in the following Table 2.

EFFECT OF THE INVENTION

According to the present invention, novel *Bacillus subtilis* mutant strains having excellent productivity of various enzymes can be provided. Through the use of the *Bacillus subtilis* mutant strains according to the present invention, not only can industrial methods for producing various enzymes with excellent productivity be realized, but also biological materials useful for elucidation of production mechanisms or the like of various enzymes can be provided.

This description includes part or all of the contents as disclosed in the description and/or drawings of Japanese Patent Application No. 2005-298406, which is a priority document of the present application.

PREFERRED EMBODIMENTS OF THE INVENTION

Figure 1:
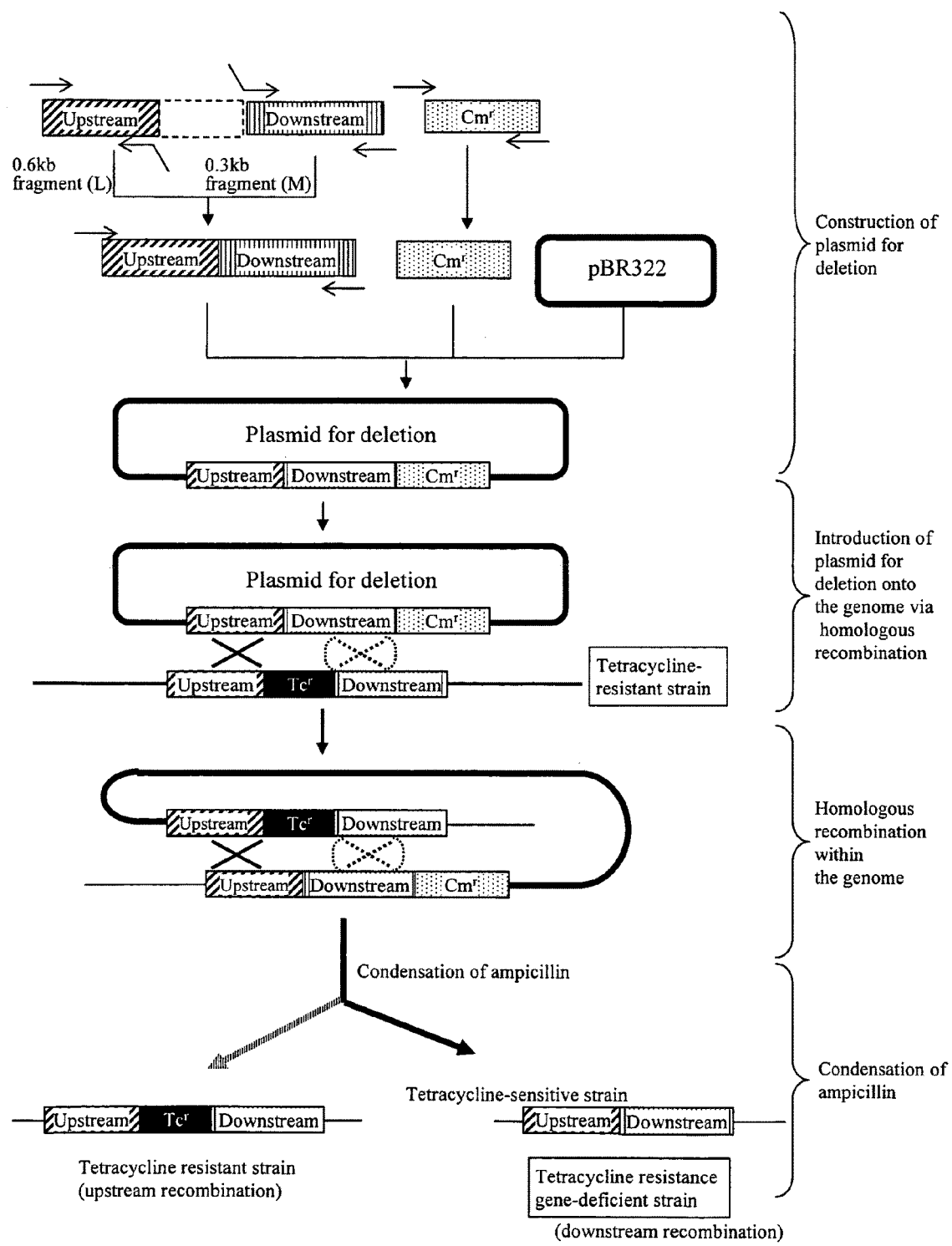
FIG. 1 is a schematic diagram for explanation of an example of a method for deletion of a predetermined region from the *Bacillus subtilis* genome.

The present invention is explained in detail as follows.

Novel *Bacillus subtilis* mutant strains provided according to the present invention can be obtained by deletion of large regions from the *Bacillus subtilis* genome. These *Bacillus subtilis* mutant strains possess improved secretory productivity of target proteins or polypeptides derived from cloned genes introduced therein. Genes to be introduced herein may be either exogenous or endogenous, as long as they encode proteins. An example of the genes may be a gene containing a nucleotide sequence that encodes a region corresponding to a secretion signal or may be a gene appropriately ligated to DNA upstream thereof containing a nucleotide sequence that encodes a region corresponding to a secretion signal. Moreover, an example of the genes may be introduced into the genome of a *Bacillus subtilis* mutant strain or may also be introduced into a *Bacillus subtilis* mutant strain as an expression vector. Furthermore, the number of such gene to be introduced herein may be one or a plural number thereof. When a plurality of genes are introduced, a plurality of genes may be introduced via arrangement thereof in a line on one DNA fragment, or may also be introduced as different DNA fragments. A technique for introduction of genes is not particularly limited. Conventionally known transformation methods, transduction methods, and the like can be used.

Examples of genes to be introduced herein include, but are not particularly limited to, secretory alkaline cellulase, secretory alkaline protease, and secretory alkaline amylase.

Novel *Bacillus subtilis* mutant strain names and deletion regions according to the present invention are listed in Table 1.

TABLE 1

| *Bacillus subtilis* mutant strain name | Deletion region |
|---|---|
| MGB533 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, and ydcL-ydeK-ydhU region |
| MGB559 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) pps (ppsE-ppsA) region, prophage2 (ydcL-ydeJ) region, ydcL-ydeK-ydhU region, and yisB-yitD region |
| MGB592 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, and yunA-yurT region |
| MGB604 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, and cgeE-ypmQ region |
| MGB625 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, and yeeK-yesX region |
| MGB653 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, and ydiM-gutR-yebA region |

TABLE 1-continued

| Bacillus subtilis mutant strain name | Deletion region |
| --- | --- |
| MGB683 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, ydiM-gutR-yebA region, and ykuS-ykqB region |
| MGB781 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, ydiM-gutR-yebA region, ykuS-ykqB region, and pdp-rocR region |
| MGB723 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, and pdp-rocR region |
| MGB773 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ yeeK-yesX region, pdp-rocR region, and ycxB-sipU region |
| MGB822 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, and SKIN-Pro7 (spoIVCB-yraK) region |
| MGB834 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, and sbo-ywhH region |
| MGB846 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, and cspB-yhcT region |
| MGB872 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2(ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, cspB-yhcT region, and yybP-yyaJ region |

TABLE 1-continued

| Bacillus subtilis mutant strain name | Deletion region |
|---|---|
| MGB885 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, cspB-yhcT region, yybP-yyaJ region, and ytxK-braB region |
| MGB913 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, ydiM-gutR-yebA region, pdp-rocR region, ycxB-sipU region, SKIN-Pro7 (spoIVCB-yraK) region, sbo-ywhH region, cspB-yhcT region, yybP-yyaJ region, and ytxK-braB region |
| MGB943 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, ydiM-gutR-yebA region, ykuS-ykqB region, pdp-rocR region, ycxB-sipU region, SKIN-Pro7 (spoIVCB-yraK) region, sbo-ywhH region, cspB-yhcT region, yybP-yyaJ region, and ytxK-braB region |
| MGB860 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, and yybP-yyaJ region |
| MGB874 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, yybP-yyaJ region, and yncM-fosB region |
| MGB887 strain | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, yybP-yyaJ region, ytxK-braB region, and yncM-fosB region |
| NED0100 strain | ybbU-ybdG-yceK region |
| NED0202 strain | ycxB-ydbP region |
| NED02021 strain | ycxB-sipU region |
| NED0301 strain | ydcD-ydcK region |
| NED0302 strain | ydcL-ydeK-ydhU region |
| NED0400 strain | ydiM-gutR-yebA region |
| NED0501 strain | yeeK-yesX region |
| NED0600 strain | cspB-yhcT region |
| NED0700 strain | yhdP-yhaL region |
| NED0802 strain | yhxD-yhjP region |
| NED0803 strain | yisB-yitD region |
| NED0804 strain | yitH-yitZ region |

TABLE 1-continued

| Bacillus subtilis mutant strain name | Deletion region |
|---|---|
| NED0900 strain | oppA-yjbK region |
| NED1002 strain | yjcM-ctaO-yjgB region |
| NED1003 strain | yjqB-htrA region |
| NED1100 strain | ykuS-ykqB region |
| NED1200 strain | slp-ylaM region |
| NED1300 strain | ctaA-ylbE region |
| NED1400 strain | gid-ylxL region |
| NED1500 strain | spoVS-ymzA region |
| NED1602 strain | yncM-fosB region |
| NED1802 strain | yoxC-yocS region |
| NED1901 strain | yojO-yozE region |
| NED1902 strain | cgeE-ypmQ region |
| NED2201 strain | ypzC-drm region |
| NED2202 strain | yqxK-yqjP region |
| NED2300 strain | zwf-yqzF region |
| NED2402 strain | yqgZ-yqgN region |
| NED2500 strain | yqeD-yrzL region |
| NED2602 strain | yrzF-yrxA region |
| NED2702 strain | ytxK-braB region |
| NED2802 strain | ytzH-ytbQ region |
| NED2900 strain | ytvB-ytoA region |
| NED3000 strain | pckA-mntA region |
| NED3200 strain | yunA-yurT region |
| NED3301 strain | yurZ-yuxN region |
| NED3303 strain | smpB-yvbK region |
| NED3402 strain | yvdM-yvcP region |
| NED3701 strain | sbo-ywhH region |
| NED3800 strain | ywcB-ywaE region |
| NED4000 strain | dltA-rocR region |
| NED4001 strain | dltA-hutM region |
| NED4002 strain | pdp-rocR region |
| NED4100 strain | yybP-yyaJ region |

In addition, deletion regions as listed in Table 1 can also be said as regions, each of which is located between oligonucleotides that form a set as listed in Table 2.

TABLE 2

| Region | Oligonucleotide set | | | |
|---|---|---|---|---|
| | 1st oligonucleotide | SEQ ID NO: | 2nd oligonucleotide | SEQ ID NO: |
| prophage1 (ybbU-ybdE) region | taagattatctaaaggggtg | SEQ ID NO: 1 | CATACAAGACGGAAATTT | SEQ ID NO: 2 |
| ybbU-ybdG-yceK region | taagattatctaaaggggtg | SEQ ID NO: 3 | CACCCATTATGTATTATAGT | SEQ ID NO: 4 |
| ycxB-ydbP region | atataaaaggatcagcactg | SEQ ID NO: 5 | TTGAAAAGGAGATGTGACAT | SEQ ID NO: 6 |
| ycxB-sipU region | atataaaaggatcagcactg | SEQ ID NO: 7 | CCATGTTCTTTTTGCATTGC | SEQ ID NO: 8 |
| ydcD-ydcK region | ggtggaggtgtatgtttttt | SEQ ID NO: 9 | CCATATTCGTCAACCTTTT | SEQ ID NO: 10 |
| prophage2 (ydcL-ydeJ) region | gcccacaaactgcccactta | SEQ ID NO: 11 | TCCTATCTATTCCATGGT | SEQ ID NO: 12 |
| ydcL-ydeK-ydhU region | gcccacaaactgcccactta | SEQ ID NO: 13 | GGGCAATCCGTGGAACGGGT | SEQ ID NO: 14 |
| prophage3 (ydiM-ydjC) region | agcgatgtgaggtgaaaatt | SEQ ID NO: 15 | TTATTAAAGTCTACAAAT | SEQ ID NO: 16 |
| ydiM-gutR-yebA region | agcgatgtgaggtgaaaatt | SEQ ID NO: 17 | TCCATAGCGCCGAAGAATCT | SEQ ID NO: 18 |
| yeeK-yesX region | atgtgaaggagagagtaaat | SEQ ID NO: 19 | CGTCTTATCCCTTAGTCCTC | SEQ ID NO: 20 |
| cspB-yhcT region | gcagttttcatatcaattt | SEQ ID NO: 21 | TCGAAAAGGAGCCATTTAAC | SEQ ID NO: 22 |
| yhdP-yhaL region | tatacaaggtgcttttctta | SEQ ID NO: 23 | CATTGAGCCGCACAGCTTTT | SEQ ID NO: 24 |
| yhxD-yhjP region | cagctcctttcataaagcta | SEQ ID NO: 25 | CAAAAAAGAACCCTCTTTTT | SEQ ID NO: 26 |
| yisB-yitD region | gatgtaagggaggagcggat | SEQ ID NO: 27 | CGACGAGAGCCCCGCAGCCG | SEQ ID NO: 28 |
| yitH-yitZ region | ctgttcgggaaaaaagaggg | SEQ ID NO: 29 | GCGGTGCCGCATTTCAGCCG | SEQ ID NO: 30 |
| oppA-yjbK region | tgaaaattattattagggggg | SEQ ID NO: 31 | GGGCGGAAAGGAAGAGCATC | SEQ ID NO: 32 |

TABLE 2-continued

| Region | Oligonucleotide set | | | |
|---|---|---|---|---|
| | 1st oligonucleotide | SEQ ID NO: | 2nd oligonucleotide | SEQ ID NO: |
| prophage4 (yjcM-yjdJ) region | ttattaagtagcggaaggca | SEQ ID NO: 33 | TGCAAAAAGAGCCACACA | SEQ ID NO: 34 |
| yjcM-cta0-yjgB region | aacgatttagtatcaattta | SEQ ID NO: 35 | GGTAGATCAATTAGGAGGGA | SEQ ID NO: 36 |
| PBSX (ykdA-xlyA) region | gacctgcaagtgctgctgat | SEQ ID NO: 37 | GATCTTCTCTTTCGTCGC | SEQ ID NO: 38 |
| yjqB-htrA region | ggtaaaggggggcgttcaag | SEQ ID NO: 39 | AGAGAAACGGAGTGAACATG | SEQ ID NO: 40 |
| ykuS-ykqB region | gcactctagtaaacggaggt | SEQ ID NO: 41 | GACGGCTTATTTGGCTGCTA | SEQ ID NO: 42 |
| slp-ylaM region | cccgctttgagcgagggct | SEQ ID NO: 43 | TAAGCATATGACATAAATTA | SEQ ID NO: 44 |
| ctaA-ylbE region | cgcctaaggctttggtctt | SEQ ID NO: 45 | CCCTTCTTCGGGGCCTTTTA | SEQ ID NO: 46 |
| gid-ylxL region | taaactaggagatgtgaaag | SEQ ID NO: 47 | CACAGCTTTATCCGACAATC | SEQ ID NO: 48 |
| pks (pksA-ymaC) region | atcagaggaaggtaataatg | SEQ ID NO: 49 | CATTCTGTTTCCAATTGT | SEQ ID NO: 50 |
| spoVS-ymzA region | aaaactaaggggggagcagaa | SEQ ID NO: 51 | CATAACATGAAAAAAAACTG | SEQ ID NO: 52 |
| prophage5 (ynxB-dut) region | ccataattacgttgaaatct | SEQ ID NO: 53 | AATCACACAGCATGGAGA | SEQ ID NO: 54 |
| yncM-fosB region | gcggcttttttgctgcttcgt | SEQ ID NO: 55 | CCTTATATGAAATATGGTTG | SEQ ID NO: 56 |
| pps (ppsE-ppsA) region | cctcttattatgagaactgg | SEQ ID NO: 57 | CTCTGTCCGCTAATCCGC | SEQ ID NO: 58 |
| prophage6 (yoaV-yobO) region | tgctgatatgctgcgggatt | SEQ ID NO: 59 | ACGCCACATTCGTGTGT | SEQ ID NO: 60 |
| yoxC-yocS region | ataagaaaaggagtgaacat | SEQ ID NO: 61 | GTACCCTTTTTGATGCATAT | SEQ ID NO: 62 |
| yojO-yozE region | cgccaaaaagcataggatta | SEQ ID NO: 63 | GACATCAGGAGGGGAAACCC | SEQ ID NO: 64 |
| spb (yodU-ypqP) region | atgtcattaatatcagtaca | SEQ ID NO: 65 | GTTCACAGGAGATACAGC | SEQ ID NO: 66 |
| cgeE-ypmQ region | ggtttgtgcaaacgcctatt | SEQ ID NO: 67 | GGCTGGAAAGGATGGATGTC | SEQ ID NO: 68 |
| ypzC-drm region | agcatgaggttacgggcagt | SEQ ID NO: 69 | GGAGGCTTTCAAGATGCCTG | SEQ ID NO: 70 |
| yqxK-yqjP region | gaactgagttaatctttagc | SEQ ID NO: 71 | TGAAGACAAGGAGCGAAAGG | SEQ ID NO: 72 |
| zwf-yqzF region | cgaataaagtgaggtacttt | SEQ ID NO: 73 | CGCGGGCTGACTTGATTGCG | SEQ ID NO: 74 |
| yqgZ-yqgN region | agcggatcttcggttttttca | SEQ ID NO: 75 | CTATTCCGAGGGGATGAGA | SEQ ID NO: 76 |
| skin (spoIVCB-spoIIIC) region | catacttttgtgaggtgac | SEQ ID NO: 77 | GAGATCCGGCTTCTTCTG | SEQ ID NO: 78 |
| prophage7 (yrkM-yraK) region | atcagaggaaggtaataatg | SEQ ID NO: 79 | CATTCTGTTTCCAATTGT | SEQ ID NO: 80 |
| SKIN-Pro7 (spoIVCB-yraK) region | catacttttgtgaggtgac | SEQ ID NO: 81 | CATTCTGTTTCCAATTGT | SEQ ID NO: 82 |
| yqeD-yrzL region | gagtgaccatagacatgtta | SEQ ID NO: 83 | GCGAATTTGGGAAAGAGG | SEQ ID NO: 84 |
| yrzF-yrxA region | gagcaaagaaggtgaatgaa | SEQ ID NO: 85 | GCCGGCTTCTTCGAGGGCTT | SEQ ID NO: 86 |
| ytxK-braB region | ctaagctgcttttaaaacac | SEQ ID NO: 87 | AACGCAGGCGTTCTGTGACA | SEQ ID NO: 88 |
| ytzH-ytbQ region | ctgaagggatgtgtaccgtt | SEQ ID NO: 89 | CGGCAAATTATGAGGAGCTG | SEQ ID NO: 90 |
| ytvB-ytoA region | cgggcggagattgaggacaa | SEQ ID NO: 91 | GGTAAAGTAAGACGAAGCAG | SEQ ID NO: 92 |
| pckA-mntA region | acgataaaggaaggtttcat | SEQ ID NO: 93 | TGGCAAAGAGGAGGAGAAAT | SEQ ID NO: 94 |
| yunA-yurT region | aaatttctcgacaagggaa | SEQ ID NO: 95 | TCGAAGGAGGGAAAAACAGT | SEQ ID NO: 96 |
| yurZ-yuxN region | ttttcggaatattccttctc | SEQ ID NO: 97 | GCTGTTCCGCATCTTTGGCG | SEQ ID NO: 98 |
| smpB-yvbK region | cgaatcaagcactatgcctt | SEQ ID NO: 99 | CGGCGGCTTTTTTATGCTTT | SEQ ID NO: 100 |
| yvdM-yvcP region | aggaattgactcccttattc | SEQ ID NO: 101 | GTACATATAAGGGGGATCAA | SEQ ID NO: 102 |
| sbo-ywhH region | gggaggattcaattatgaaa | SEQ ID NO: 103 | GACGATGTCTGGATGTTTTT | SEQ ID NO: 104 |
| ywcB-ywaE region | cgaataaaggaggaaagcc | SEQ ID NO: 105 | TACTGGATTCCCGTCAAAGC | SEQ ID NO: 106 |
| dltA-rocR region | ccgcgaataccggttcatat | SEQ ID NO: 107 | GATCAGGCTTCCTGCTCCGG | SEQ ID NO: 108 |

TABLE 2-continued

| | Oligonucleotide set | | | |
|---|---|---|---|---|
| Region | 1st oligonucleotide | SEQ ID NO: | 2nd oligonucleotide | SEQ ID NO: |
| dltA-hutM region | ccgcgaataccggttcatat | SEQ ID NO: 109 | CCATGCTGAGCGGGGTGTGC | SEQ ID NO: 110 |
| pdp-rocR region | ggcgccttcgcttccgcggc | SEQ ID NO: 111 | GATCAGGCTTCCTGCTCCGG | SEQ ID NO: 112 |
| yybP-yyaJ region | ccgcgtcgggatgcttttttc | SEQ ID NO: 113 | GCAGATCCGCACTGACTTTT | SEQ ID NO: 114 |

In addition, an example of each *Bacillus subtilis* mutant strain according to the present invention is a mutant strain having a genomic structure prepared by deletion of other regions in addition to deletion regions as defined above from the genomic DNA of a standard wild-type strain (e.g., *Bacillus subtilis* 168 strain). Examples of such "other regions" include gene regions excluding genes essential for growth and non-coding regions. Regions that do not lower the ability of performing above-described secretion and production even if they are deleted from the genome are preferable.

A method for deleting deletion regions listed in Table 1 from the *Bacillus subtilis* genome is not particularly limited. For example, a method as described below and shown in FIG. 1 can be applied herein.

Specifically, deletion regions listed in Table 1 are deleted from the *Bacillus subtilis* genome through the use of a two-staged single-cross method using a plasmid for deletion constructed via insertion of a DNA fragment for deletion (that is prepared by namely the SOE-PCR method (Gene, 77, 61 (1989)). A DNA fragment for deletion, which is used in the method, is a DNA fragment prepared by ligating an approximately 0.1-kb to 3-kb fragment (referred to as an upstream fragment) adjacent upstream of a subject region (region to be deleted) to an approximately 0.1-kb to 3-kb fragment (referred to as a downstream fragment) adjacent downstream of the same. Furthermore, a DNA fragment prepared by binding a drug resistance marker gene fragment such as a chloramphenicol resistance gene to downstream or upstream of the DNA fragment can also be used herein.

First, three fragments are prepared by the 1$^{st}$ PCR: an upstream fragment and a downstream fragment of a subject gene (to be subjected to deletion); and if necessary a drug resistance marker gene fragment. At this time, primers are designed in which the terminal 10- to 30-base-pair sequences of subject DNA fragments (to be subjected to binding) are added to the primers. For example, when an upstream fragment and a downstream fragment are ligated in this order: a sequence corresponding to 10 to 30 nucleotides on the upstream side of the downstream fragment is added to the 5' end of a primer located on (annealed to) the downstream end of the upstream fragment; and a sequence corresponding to 10 to 30 nucleotides on the downstream side of the upstream fragment is added to the 5' end of a primer located on (annealed to) the upstream end of the downstream fragment. When an upstream fragment and a downstream fragment are amplified with the use of the thus designed primer set: a region corresponding to that on the upstream side of the downstream fragment is added to the downstream side of the thus amplified upstream fragment; a region corresponding to that on the downstream side of the upstream fragment is added to the upstream side of the thus amplified downstream fragment.

Next, the upstream fragment and the downstream fragment prepared by the 1$^{st}$ PCR are mixed. The 2$^{nd}$ PCR is then performed using the resultant as a template and a pair of primers comprising a primer located on (annealed to) the upstream side of the upstream fragment and a primer located on (annealed to) the downstream side of the downstream fragment. A DNA fragment for deletion prepared by binding the upstream fragment to the downstream fragment in this order can be amplified by the 2$^{nd}$ PCR.

In addition, when a drug resistance marker gene fragment is ligated to a DNA fragment for deletion, the drug resistance marker gene fragment is amplified by the 1$^{st}$ PCR so as to add a region corresponding to that on the downstream side of a downstream fragment. Subsequently the 2$^{nd}$ PCR is performed using a pair of primers comprising a primer located on (annealed to) the upstream side of the upstream fragment and a primer located on (annealed to) the downstream side of the drug resistance marker gene fragment. Accordingly, a DNA fragment for deletion prepared by binding the upstream fragment, the downstream fragment, and the drug resistance marker gene fragment in this order can be amplified.

Furthermore, after amplification by the 2$^{nd}$ PCR of a DNA fragment for deletion prepared by binding a upstream fragment to a downstream fragment in this order, the DNA fragment for deletion is inserted into a plasmid containing the drug resistance marker gene. Then the DNA fragment for deletion having the upstream fragment, the downstream fragment, and the drug resistance marker gene fragment in this order may be prepared.

Furthermore, a plasmid for introduction of deletion is constructed by inserting a DNA fragment for deletion that is obtained by the above method or the like into a plasmid DNA that is not amplified within host bacteria using general restriction enzymes and DNA ligase or into a plasmid DNA (e.g., temperature-sensitive plasmid) that can be easily removed. Examples of such plasmid DNA that is not amplified within host bacteria include, but are not limited to, pUC18, pUC118, and pBR322 when *Bacillus subtilis* is used as a host, for example.

Subsequently, a host bacterium is transformed using such plasmid for deletion by a competent cell transformation method (J. Bacteriol. 93, 1925 (1967)) or the like. Thus, a transformant is obtained in which the plasmid for deletion is fused within the genomic DNA of the host bacterium can be obtained through single-cross homologous recombination between the upstream fragment or the downstream fragment inserted in the plasmid and the homologous region on the genome. Transformants may be selected using the drug resistance of a marker gene such as a chloramphenicol resistance gene of a plasmid for introduction of deletion as an indicator.

On the genome of the thus obtained transformant, the upstream and downstream region sequences of the drug resistance gene, which are to be deleted, are present redundantly. Specifically, such upstream and downstream region sequences derived from host bacterial genome and the same derived from the plasmid for deletion are present redundantly. Of these upstream or downstream regions, deletion of a target gene (to be deleted) such as the drug resistance gene on the genome takes place in addition to deletion of the region derived from the plasmid for deletion by causing homologous recombination to take place within the genome at a region differing from a region that has undergone homologous recombination when the transformant is acquired. An example of a method for causing homologous recombination within the genome is a method that involves induction of competence, for example (J. Bacteriol. 93, 1925 (1967)). Homologous recombination takes place by spontaneous induction even in a simple culture in general medium. Bacterial strains that have undergone homologous recombination within the genome as intended have simultaneously lost their resistance to the drug as a result of deletion of the relevant drug resistance gene. Hence, such bacterial strains that have undergone homologous recombination can be selected from the resulting drug-sensitive bacterial strains. Genomic DNA is extracted from these bacterial strains and then the deletion of a target gene may be confirmed by the PCR method or the like.

When target deletion strains are selected, direct selection of drug-sensitive bacterial strains altered from drug-resistant strains is difficult. Moreover, it is considered that homologous recombination within the genome takes place with a frequency as low as approximately $10^{-4}$ or less. Hence, it is desired to contrive ways such as a way of enhancing the proportion of existing drug-sensitive strains in order to efficiently obtain target deletion strains. An example of a method for condensing drug-sensitive strains is a condensation method that uses the fact that penicillin-based antibiotics such as ampicillin act on proliferated cells bacteriocidally, whereas such antibiotics do not act on un-proliferated cells (Methods in Molecular Genetics, Cold Spring Harbor Labs, (1970)). When condensation using ampicillin or the like is performed, this is effective for deletion of a resistance gene against a drug (e.g., tetracycline or chloramphenicol) that bacteriostatically acts on host cells. A resistant strain retaining such a drug resistance gene can be grown in appropriate medium containing an appropriate amount of the relevant drug with bacteriostatic effects. Drug-sensitive strains lacking the drug resistance gene neither proliferate nor die. Under such conditions, penicillin-based antibiotic such as ampicillin with an appropriate concentration is added and then culture is performed. Resistant strains to be proliferated die and sensitive strains remain unaffected by ampicillin or the like, so that the proportion of existing sensitive strains is increased. Appropriate agar medium is coated with a culture solution that has been subjected to such condensation procedure and then culture is performed. The presence or the absence of the resistance of colonies that have appeared against a marker drug is confirmed by a replica method or the like. Thus, efficient selection of sensitive strains is made possible.

As described above, a *Bacillus subtilis* mutant strain having a genomic structure lacking a predetermined single region on the genome can be produced. Furthermore, a *Bacillus subtilis* mutant strain having a genomic structure lacking a plurality of regions can be produced by namely an LP (lysis of protoplasts) transformation method. The LP transformation method can be used by referring to "T. Akamatsu and J. Sekiguchi, "Archives of Microbiology," 1987, vol. 146, p. 353-357" and "T. Akamatsu and H. Taguchi, "Bioscience, Biotechnology, and Biochemistry," 2001, vol. 65, No. 4, p. 823-829." Specifically, according to the LP transformation method, a protoplast obtained via the lysis of the cell wall is provided as a donor DNA for competent cells of a recipient bacterial strain. It is thought that the protoplast added herein is disrupted by osmotic shock and then the donor DNA released in a culture solution is incorporated into the competent cells of the recipient bacterial strain. Furthermore, damage to DNA to be introduced can be drastically reduced by the use of the LP transformation method unlike the use of a general transformation method.

Through application of the LP transformation method, another *Bacillus subtilis* mutant strain having a genomic structure prepared by deletion of a plurality of regions from a *Bacillus subtilis* mutant strain having a genomic structure having a single deletion can be produced. Specifically, first, protoplasts of a *Bacillus subtilis* mutant strain having a genomic structure lacking a predetermined region (referred to as a $1^{st}$ deletion region) are prepared. The protoplasts are caused to coexist with competent cells of a *Bacillus subtilis* mutant strain having a genomic structure lacking a different region ($2^{nd}$ deletion region). Thus, a set of a cross-strand exchange structure is formed between genomic DNA (donor DNA) having the 1st deletion region and genomic DNA (host DNA) having the $2^{nd}$ deletion region. This set of a cross-strand exchange structure is generated at a position where the 1st deletion region is located between them in donor DNA. Thus the $1^{st}$ deletion region in donor DNA is introduced into the host DNA. As described above, through application of the LP transformation method, a *Bacillus subtilis* mutant strain having a genomic structure lacking the $1^{st}$ deletion region and the $2^{nd}$ deletion region can be produced. Through application of this method, a *Bacillus subtilis* mutant strain having a genomic structure lacking a plurality of regions can be produced, as long as genes essential for growth are not deleted.

The *Bacillus subtilis* mutant strains according to the present invention that are produced as described above are characterized by having better ability to perform secretion and production of proteins or polypeptides that are encoded by introduced genes than a wild standard bacterial strain such as the *Bacillus subtilis* 168 strain. Examples of target proteins or target polypeptides that are produced using the *Bacillus subtilis* mutant strains of the present invention are not particularly limited and include enzymes for industrial use or physiologically active peptides, which are used for various industrial fields relating to detergents, foods, fibers, feedstuffs, chemical products, medicine, diagnosis, and the like. In particular, enzymes for industrial use are preferable. Examples of enzymes for industrial use include, when classified based on functions, oxidoreductase, transferase, hydrolase, lyase, isomerase, and Ligase/Synthetase. Of these, examples of target proteins that are produced using the *Bacillus subtilis* mutant strains of the present invention preferably include hydrolases such as cellulase, α-amylase, and protease.

For example, in a *Bacillus subtilis* mutant strain into which cellulase, protease, and amylase genes have been introduced, the production amounts of enzymes that are secreted out of the bacterial bodies are significantly improved compared with those of a wild standard bacterial strain into which the same enzymes have been introduced. The secretory productivity of these enzymes in the *Bacillus subtilis* mutant strains according to the present invention can be measured through application of various conventionally known techniques without limitation.

The productivity of cellulase can be measured as follows, for example. First, a test *Bacillus subtilis* mutant strain is transformed with a vector having a cellulase gene. Next, the thus obtained transformants are cultured and then culture supernatants are obtained by centrifugation or the like to remove bacterial bodies. p-nitrophenyl-β-D-cellotrioside (Seikagaku Corporation) is added as a substrate to each of the thus obtained supernatants, for example, and then reaction is performed for a predetermined time. The amount of p-nitrophenol liberated when the reaction is performed is quantified based on a change in absorbance (OD420 nm) at 420 nm. Therefore, the productivity of cellulase encoded by the cellulase gene that has been introduced into the test *Bacillus subtilis* mutant strain can be measured. In addition, cellulase productivity of a standard wild-type strain such as the *Bacillus subtilis* 168 strain is measured in the same manner, so that the cellulase productivity of the test *Bacillus subtilis* mutant strain can be evaluated as a value relative to that of the standard wild-type strain.

An example of cellulase is cellulase belonging to family 5 of the polysaccharide hydrolase classification (Biochem. J., 280, 309, 1991). Of such cellulases, cellulase derived from a microorganism, and in particular, derived from bacteria belonging to the genus *Bacillus*, is preferable. A more specific example of the same is: alkaline cellulase comprising the amino acid sequence represented by SEQ ID NO: 116 derived from the bacterium KSM-S237 strain (FERM BP-7875) belonging to the genus *Bacillus*; alkaline cellulase comprising the amino acid sequence represented by SEQ ID NO: 118 derived from the bacterium KSM-64 strain (FERM BP-2886) belonging to the genus *Bacillus*; or cellulase comprising an amino acid sequence having 70%, preferably 80%, more preferably 90% or more, further preferably 95% or more, and particularly preferably 98% or more identity with the relevant amino acid sequence. In addition, alkaline cellulase having the amino acid sequence represented by SEQ ID NO: 116 and alkaline cellulase having the amino acid sequence represented by SEQ ID NO: 118 show approximately 92% identity as a result of amino acid sequence comparison. Both cellulases are appropriate as specific examples of cellulases to be used in the present invention. Alkaline cellulase having the amino acid sequence represented by SEQ ID NO: 116 is more preferable.

For production of such cellulase, among the *Bacillus subtilis* mutant strains of the present invention, it is more preferable to use a *Bacillus subtilis* mutant strain selected from among MGB653 strain, MGB683 strain, MGB781 strain, MGB723 strain, MGB773 strain, MGB822 strain, MGB834 strain, MGB846 strain, MGB872 strain, MGB885 strain, MGB913 strain, MGB860 strain, MGB874 strain, MGB887 strain, NED02021 strain, NED0400 strain, NED0600 strain, NED0803 strain, NED0804 strain, NED1100 strain, NED1200 strain, NED1400 strain, NED1500 strain, NED1901 strain, NED1902 strain, NED2201 strain, NED2202 strain, NED2402 strain, NED2500 strain, NED2602 strain, NED2702 strain, NED2802 strain, NED3000 strain, NED3200 strain, NED3303 strain, NED3701 strain, NED3800 strain, NED4000 strain, NED4001 strain, NED4002 strain, and NED4100 strain as listed in Table 1.

The productivity of protease can be measured as follows, for example. First, a test *Bacillus subtilis* mutant strain is transformed with a vector having a protease gene. Next, the thus obtained transformants are cultured and then culture supernatants are obtained by centrifugation or the like to remove bacterial bodies. Succinyl-L-Alanyl-L-Alanyl-L-Alanine p-Nitroanilide (STANA PEPTIDE INSTITUTE, INC.) is added as a substrate to each of the thus obtained supernatants, for example, and then reaction is performed for a predetermined time. The amount of p-nitroaniline liberated when the reaction is performed is quantified based on a change in absorbance (OD420 nm) at 420 nm. Therefore, the productivity of protease encoded by the protease gene that has been introduced into the test *Bacillus subtilis* mutant strain can be measured. In addition, protease productivity of a standard wild-type strain such as the *Bacillus subtilis* 168 strain is measured in the same manner, so that the protease productivity of the test *Bacillus subtilis* mutant strain can be evaluated as a value relative to that of the standard wild-type strain.

Specific examples of protease include those derived from microorganisms and in particular serine protease derived from bacteria belonging to the genus *Bacillus* and metal protease. More specific examples of protease include alkaline protease comprising the amino acid sequence represented by SEQ ID NO: 119 derived from *Bacillus clausii* KSM-K16 strain (FERM BP-3376) and protease comprising an amino acid sequence that has 70%, preferably 80%, more preferably 90% or more, further preferably 95% or more, and particularly preferably 98% or more identity with the relevant amino acid sequence.

For production of such protease, among the *Bacillus subtilis* mutant strains of the present invention, it is more preferable to use a *Bacillus subtilis* mutant strain selected from among MGB533 strain, MGB592 strain, MGB604 strain, MGB625 strain, MGB653 strain, MGB683 strain, MGB781 strain, MGB723 strain, MGB773 strain, MGB822 strain, MGB834 strain, MGB846 strain, MGB872 strain, MGB885 strain, MGB913 strain, MGB943 strain, MGB860 strain, MGB874 strain, MGB887 strain, NED0302 strain, NED0400 strain, NED0600 strain, NED0803 strain, NED1500 strain, NED 1902 strain, and NED3200 strain.

The productivity of alkaline amylase can be measured as follows, for example. First, a test *Bacillus subtilis* mutant strain is transformed with a vector having an alkaline amylase gene. Next, the thus obtained transformants are cultured and then culture supernatants are obtained by centrifugation or the like to remove bacterial bodies. Then, for example, the activity of alkaline amylase contained in each of the supernatants can be determined using Liquitech Amy EPS (Roche Diagnostics) that is a kit for determining amylase activity. Therefore, the productivity of alkaline amylase encoded by the alkaline amylase gene that has been introduced into the test *Bacillus subtilis* mutant strain can be measured. In addition, alkaline amylase productivity of a standard wild-type strain such as the *Bacillus subtilis* 168 strain is measured in the same manner, so that the alkaline amylase productivity of the test *Bacillus subtilis* mutant strain can be evaluated as a value relative to that of the standard wild-type strain.

A specific example of amylase is α-amylase derived from a microorganism. In particular, amylase of liquefying type derived from bacteria belonging to the genus Bacillus is preferable. More specific examples of amylase include alkaline amylase comprising the amino acid sequence represented by SEQ ID NO: 120 derived from bacteria of KSM-K38 strain (FERM BP-6946) belonging to the genus *Bacillus* and amylase comprising an amino acid sequence having 70%, preferably 80%, more preferably 90% or more, further preferably 95% or more, and particularly preferably 98% or more identity with the relevant amino acid sequence.

For production of such α-amylase, among the *Bacillus subtilis* mutant strain of the present invention, it is more preferable to use a *Bacillus subtilis* mutant strain selected from among MGB653 strain, NED0301 strain, NED0302 strain, NED0400 strain, NED0600 strain, NED0802 strain, NED0804 strain, NED0900 strain, NED1002 strain, NED1003 strain, NED100 strain, NED1602 strain, NED2602 strain, NED2702 strain, NED3402 strain, NED3701 strain, and NED3800 strain.

A gene of a target protein or polypeptide, which is introduced into the *Bacillus subtilis* mutant strains of the present invention, desirably comprises one or more control regions (involved in transcription, translation, and secretion of the gene) that are bound upstream of the gene in a right form.

Specifically, such regions are selected from among a transcriptional initiation-controlling region containing a promoter and a transcription initiation point, a translation initiation region containing a ribosome-binding site and an initiation codon, and a secretion signal peptide region. In particular, three regions comprising a transcriptional initiation-controlling region, translational initiation-controlling region, and a secretion signal region are preferably bound. Furthermore, the three regions in which: a secretion signal peptide region is derived from a cellulase gene of bacteria of the genus *Bacillus*; and a transcription initiation region and a translation initiation region are included in a 0.6-kb to 1-kb region located upstream of the cellulase gene are desirably bound to the gene of a target protein or polypeptide in a right form. For example, it is desirable that a transcriptional initiation-controlling region, a translation initiation region, and a secretion signal peptide region of a cellulase gene derived from bacteria of the genus *Bacillus* described in JP Patent Publication (Kokai) No. 2000-210081 A, JP Patent Publication (Kokai) No. 4-190793 A (1992), and the like; that is, KSM-S237 strain (FERM BP-7875) or KSM-64 strain (FERM BP-2886) be properly bound to a structural gene of a target protein or polypeptide. More specifically, it is desirable that a nucleotide sequence ranging from nucleotide Nos. 1 to 659 of the nucleotide sequence represented by SEQ ID NO: 115, a nucleotide sequence ranging from nucleotide Nos. 1 to 696 of a cellulase gene comprising the nucleotide sequence represented by SEQ ID NO: 117, a DNA fragment comprising a nucleotide sequence having 70% or more, preferably 80% or more, more preferably 90% or more, further preferably 95% or more, and particularly preferably 98% or more identity with the relevant nucleotide sequence, or a DNA fragment comprising a nucleotide sequence derived from any one of the above nucleotide sequences by partial deletion be properly bound to a structural gene of a target protein or polypeptide. In addition, here, such a DNA fragment comprising a nucleotide sequence derived from any one of the above nucleotide sequences by partial deletion means a DNA fragment lacking a portion of the relevant nucleotide sequence, but retains functions involved in gene transcription, translation, and secretion.

EXAMPLES

The present invention will be further described specifically with reference to examples. However, the technical scope of the present invention is not limited by the following examples.

In the Examples, mutant strains were produced by deletion of various regions on the genome of the *Bacillus subtilis* 168 strain as a wild-type strain. In addition, regarding various primers used in the Examples, the correspondence among primer names, nucleotide sequences, and SEQ ID NOS: are listed in Table 10 at the end of the Examples.

Example 1

Preparation of Mutant Strains Lacking a Plurality of Regions

<Preparation of a Upp-Gene-Deficient Strain Containing a Cat-upp Cassette>

Figure 2:
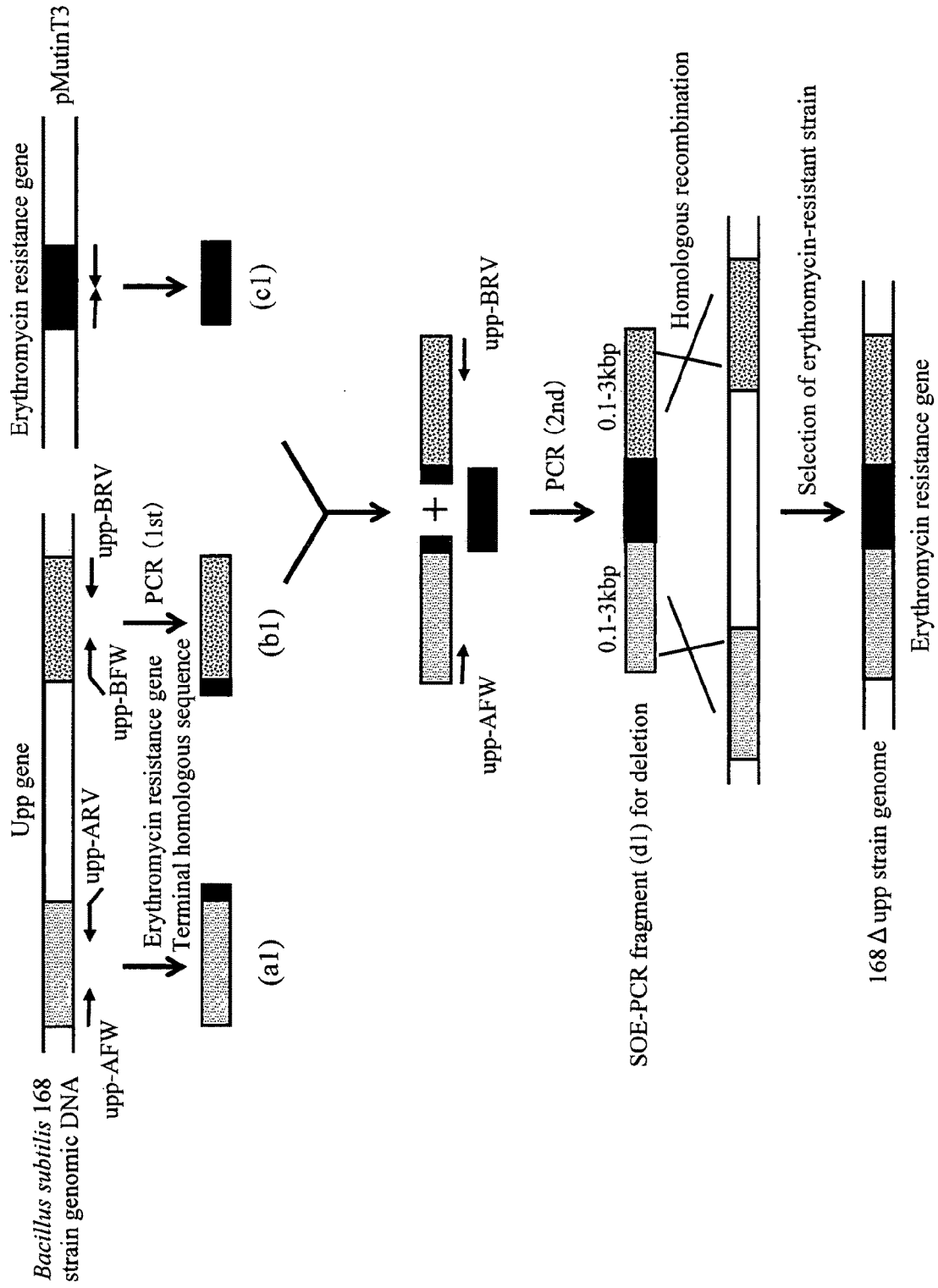
FIG. 2 is a schematic diagram for explanation of procedures for preparing the *Bacillus subtilis* 168Δupp strain from the *Bacillus subtilis* 168 strain.

As shown in FIG. 2, a 1.0-kb fragment (a1) adjacent upstream of the upp gene, (BG 13408; uracil phosphoribosyltransferase) in the genome and a 1.0-kb fragment (b1) adjacent downstream of the same were amplified by PCR using genomic DNA extracted from the *Bacillus subtilis* 168 strain as a template, a primer set of upp-AFW and upp-ARV, and a primer set of upp-BFW and upp-BRV. Moreover, a 1.2-kb fragment (c1) containing an erythromycin resistance gene was prepared by PCR using a plasmid pMutinT3 (Microbiology, 144, 3097, 1998) as a template and a primer set of Erm-FW and Erm-RV. In addition, PCR reaction was performed according to attached protocols using 20 μL of a reaction system and LATaq polymerase (produced by TAKARA BIO INC.). For preparation of (a1) and (b1), 50 ng of *Bacillus subtilis* 168 strain genome (the template DNA) was used. For preparation of (c1), 1 ng of plasmid DNA, 200 nM each of the above primers, 200 μM each of dATP, dTTP, dCTP, and dGTP, 0.2 U of LATaq, and an attached 10× buffer solution were mixed to obtain a 1× solution. A PCR system (produced by Applied Biosystems, GeneAmp9700) was used for an amplification reaction, by which 5 minutes of thermal denaturation was performed at 95° C.; 25 reaction cycles each consisting of 95° C. for 15 seconds, 55° C. for 30 seconds, and 72° C. for 60 seconds were performed; and then 30 seconds of reaction was finally performed at 72° C. so as to complete elongation. The three PCR amplification fragments (a1), (b1), and (c1) obtained as described above were purified with Centricon (produced by Millipore Corporation) and then they (0.5 μL each) were mixed. Primers upp-AFW and upp-BRV were further added, the time for reaction at 72° C. in the above PCR conditions was changed to 3 minutes, and then SOE-PCR was performed. As a result of the PCR, a 3.2-kb DNA fragment (d1) was obtained in which the three fragments were bound in the order of (a1), (c1), and (b1). The *Bacillus subtilis* 168 strain was transformed by a competent method (J. Bacteriol., 81, 741, 1960) using the DNA fragment. Specifically, the *Bacillus subtilis* 168 strain was subjected to shake culture in SPI medium (0.20% ammonium sulfate, 1.40% dipotassium hydrogen phosphate, 0.60% potassium dihydrogen phosphate, 0.10% trisodium citrate dihydrate, 0.50% glucose, 0.02% casamino acid (Difco), 5 mM magnesium sulfate, 0.25 μM manganese chloride, and 50 μg/ml tryptophan) at 37° C. until the degree of growth (OD600) reached approximately 1. After shake culture, a portion of the culture solution was inoculated to SPII medium (0.20% ammonium sulfate, 1.40% dipotassium hydrogen phosphate, 0.60% potassium dihydrogen phosphate, 0.10% trisodium citrate dihydrate, 0.50% glucose, 0.01% casamino acid (Difco), 5 mM magnesium sulfate, 0.40 μM manganese chloride, and 5 Hg/ml tryptophan) in an amount 9 times greater than that of the culture solution, followed by shake culture until the degree of growth (OD600) reached approximately 0.4. Thus, competent cells of the *Bacillus subtilis* 168 strain were prepared. Subsequently, 5 μL of a solution (reaction solution of the above SOE-PCR) containing the above DNA fragment (d1) was added to 100 μL of the thus prepared competent cell suspension (culture solution of SPII medium). After shake culture was performed at 37° C. for 1 hour, LB agar medium (1% trypton, 0.5% yeast extract, 1% NaCl, and 1.5% agar) containing 0.5 g/mL erythromycin was coated with the entire amount of the solution. After static culture was performed at 37° C., colonies that had grown were separated as transformants. Genome was extracted from the thus obtained transformants. PCR was performed using the genome as a template, so that deletion of the upp gene from the genome and substitution of the upp gene with an erythromycin resistance gene were confirmed. This strain is herein after denoted as 168Δupp. In addition, transformation using the competent method as described below was performed in the same manner as that of the above method except that DNA to be used and agar medium for selection of transformants were adequately varied.

<Construction of a Cat-upp Cassette DNA Fragment>

Figure 3:
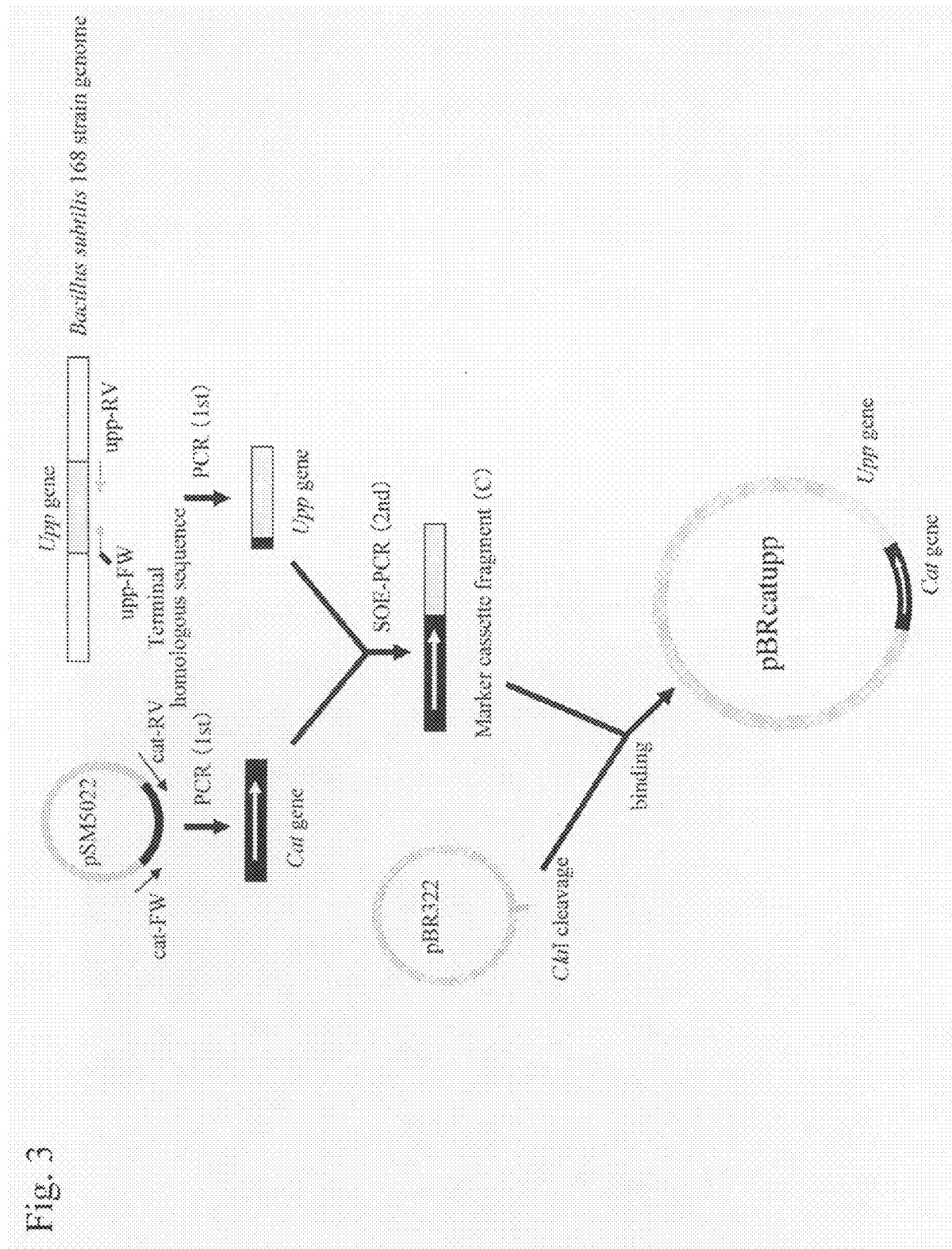
FIG. 3 is a schematic diagram for explanation of procedures for constructing a recombinant plasmid pBRcatupp via insertion of a cat-upp cassette DNA fragment.

As shown in FIG. 3, an upp gene was ligated downstream of a chloramphenicol resistance gene (cat) of plasmid pSM5022 (Mol. Microbiol. 6, 309, 1992), the transcription of which had been confirmed in *Bacillus subtilis*, so as to ensure the transcription of the upp gene and the cat gene. Specifically, a 1.3-kb DNA fragment containing cat was amplified by PCR using a primer set of cat-Fw and cat-Rv and pSM5022 as a template. Moreover, PCR was performed using primers upp-Fw and upp-RV and the 168 strain genome as a template, so that a 1.1-kb DNA fragment containing the upp gene could be obtained. Next, these two fragments were purified and then bound by SOE-PCR. Thus a 2.4-kb ca-upp cassette DNA fragment (C) was prepared, in which the upp gene was bound downstream of the cat gene. Furthermore, the fragment was inserted into a Cla I cleavage site of a plasmid pBR322, so that a recombinant plasmid pBRcatupp was obtained.

<Preparation of a Pro1-Region-Deficient Strain Containing a Cat-upp Cassette Fragment>

Figure 4:
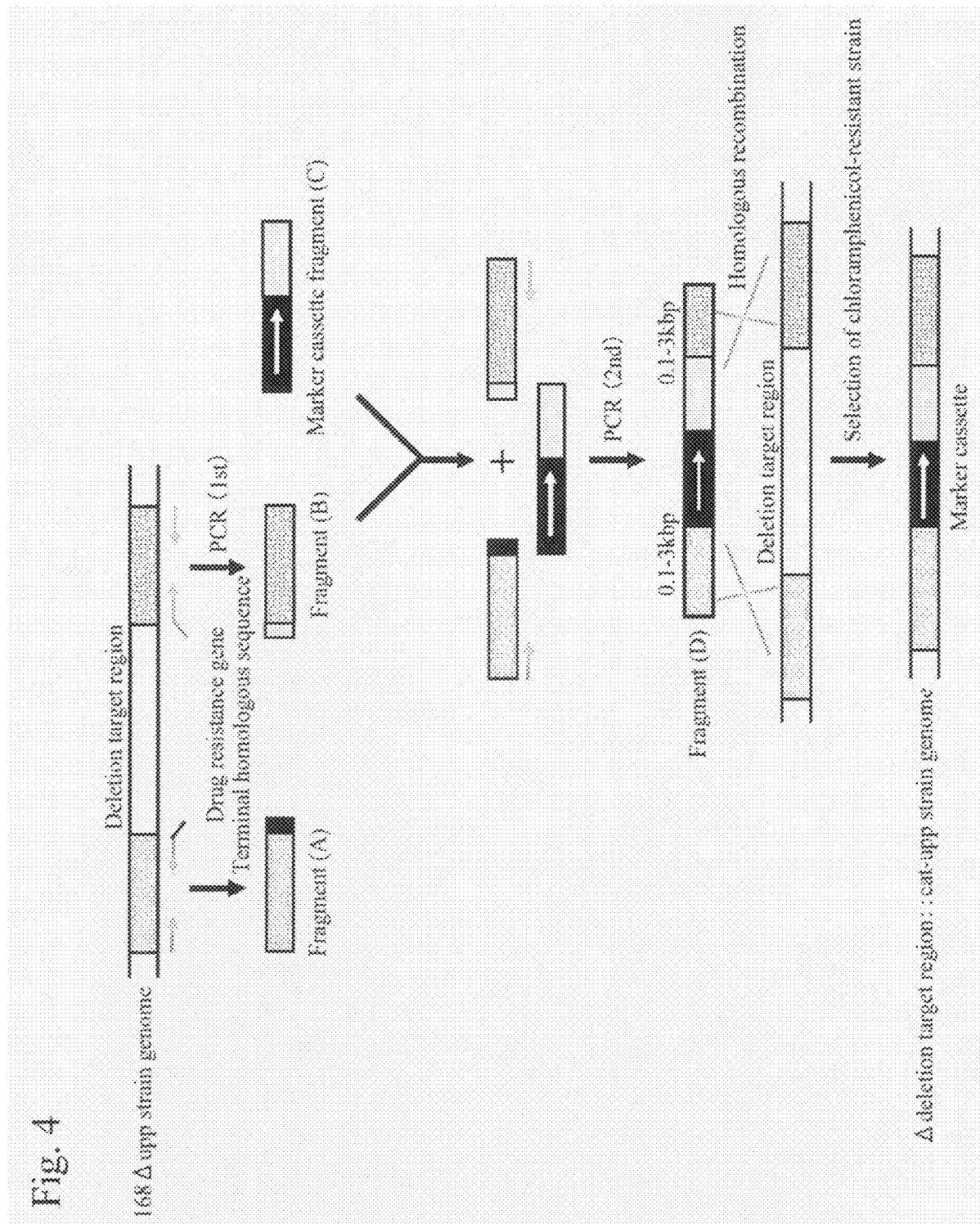
FIG. 4 is a schematic diagram for explanation of procedures for preparing a Δdeletion target region::cat-upp strain.

As shown in FIG. 4, a 0.6-kb fragment (A) adjacent upstream of a Pro1 region and a 0.3-kb fragment (B) adjacent downstream of the same region were prepared by PCR using a primer set of Pro1-AFW and Pro1-ARV, a primer set of Pro1-BFW and Pro1-BRV, and the genome of the 168 strain as a template. In addition, in FIG. 4, the Pro1 region is denoted as a "deletion target region."

Next, SOE-PCR was performed using the thus obtained PCR amplification fragments (A) and (B) and the above cat-upp cassette fragment (C) as templates and primers Pro1-AFW and Pro1-BRV, so that the three fragments were bound in the order of (A), (C), and (B). The 168Δupp strain described in Example 2 was transformed by the competent method using the thus obtained DNA fragment (D). Transformants capable of growing in LB agar medium containing 10 ppm chloramphenicol were separated. It was confirmed that in the thus obtained transformants, the Pro1 region had been deleted from the genome and substituted with the cat-upp cassette DNA fragment as a result of PCR. Furthermore, the transformants were cultured on Cg+ glucose agar medium (7% dipotassium hydrogen phosphate, 3% potassium dihydrogen phosphate, 0.5% sodium citrate, 1% ammonium sulfate, 0.1% magnesium sulfate, 0.05% glutamic acid, 0.5% glucose, 10 ng/mL L-tryptophan, 0.55 μg/mL calcium chloride, 0.17 μg/mL zinc chloride, 43 ng/mL copper chloride dihydrate, 60 ng/mL cobalt chloride hexahydrate, 60 ng/mL sodium molybdate (IV) dihydrate, and 1.5% agar) supplemented with various concentrations of 5FU (produced by Sigma-Aldrich Corporation). No growth was observed on medium supplemented with 5FU having a concentration of 0.5 μg/mL or more. On the other hand, the growth of the 168Δupp strain, the parent strain of the transformants, was observed even on medium supplemented with 5 μg/mL 5FU under the same conditions. Based on the above results, it was inferred that the upp gene introduced into the transformants had been expressed via transcription from the cat gene promoter so that the transformants had become sensitive to 5FU. The thus obtained strain was designated as the ΔPro1::cat-upp strain. In addition, in FIG. 4, the ΔPro1::cat-upp strain is denoted as the Δdeletion target region::cat-upp strain.

<Deletion of the cat-upp Cassette Fragment (C) from the Pro1 Region-Deficient Strain>

Figure 5:
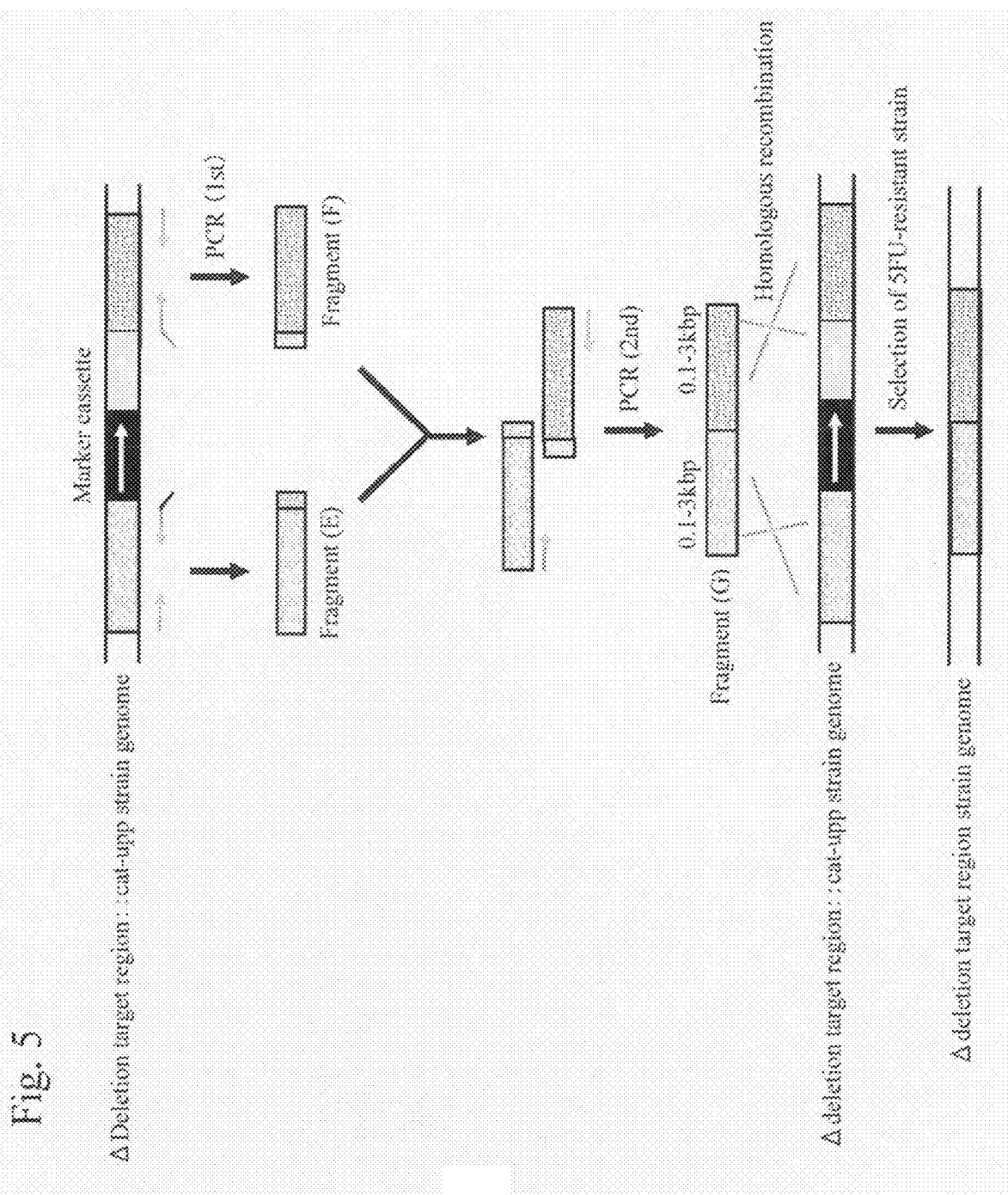
FIG. 5 is a schematic diagram for explanation of procedures for preparing a Δdeletion target region strain.

As shown in FIG. 5, a 0.6-kb fragment (E) adjacent upstream of the cat-upp cassette fragment (C) and a 0.3-kb fragment (F) adjacent downstream of the same were amplified using ΔPro1::cat-upp strain genome as a template, a primer set of Pro1-AFW and Pro1-ERV, and a primer set of Pro1-FFW and Pro1-BRV. Furthermore, SOE-PCR was performed using both the thus obtained DNA fragments as templates and a primer set of Pro1-AFW and Pro1-BRV, so that a 0.9-kb fragment (G) was prepared in which both fragments had been bound to each other. The above ΔPro1::cat-upp strain was transformed by a competent method using the fragment (G). Thus, a strain capable of growing in Cg+glucose agar medium supplemented with 1 μg/mL 5FU was obtained. The thus obtained strain was confirmed to be susceptible to chloramphenicol and to lack the Pro1 region and the cat-upp cassette DNA fragment on the genome. This strain was designated the ΔPro1 strain. In addition, in FIG. 5, the ΔPro1::cat-upp strain and the ΔPro1 strain are denoted as the "Δdeletion target region::cat-upp strain" and the "Δdeletion target region strain," respectively.

<Preparation 1 of Single-Region-Deficient Strains>

According to the above procedures for preparation of the ΔPro1 strain, a ΔPro2::cat-upp strain, a ΔPro3::cat-upp strain, a ΔPro4::cat-upp strain, a ΔPro5::cat-upp strain, a ΔPro6::cat-upp strain, a ΔPro7::cat-upp strain, a ΔPBSX::cat-upp strain, a ΔSPβ::cat-upp strain, a ΔSKIN::cat-upp strain, a Δpks::cat-upp strain, and a Δpps::cat-upp strain were prepared by the method explained in FIG. 4. Furthermore, a ΔPro2 strain, a ΔPro3 strain, a ΔPro4 strain, a ΔPro5 strain, a ΔPro6 strain, a ΔPro7 strain, a ΔPBSX strain, a ΔSPβ strain, a ΔSKIN strain, a Δpks strain, and a Δpps strain were prepared by the method explained in FIG. 5. Primer sets used in steps of preparing each of these strains for amplification of fragments (A) to (G) are listed in the following Table 3.

TABLE 3

| | Deletion target region | | | | | |
|---|---|---|---|---|---|---|
| | Pro1 | Pro3 | Pro4 | Pro7 | PBSX | SPβ |
| Fragment (A) | Pro1-AFW | Pro3-AFW | Pro4-AFW | Pro7-AFW | PBSX-AFW | spB-AFW |
| | Pro1-ARV | Pro3-ARV | Pro4-ARV | Pro7-ARV | PBSX-ARV | spB-ARV |
| Fragment (B) | Pro1-BFW | Pro3-BFW | Pro4-BFW | Pro7-BFW | PBSX-BFW | spB-BFW |
| | Pro1-BRV | Pro3-BRV | Pro4-BRV | Pro7-BRV | PBSX-BRV | spB-BRV |
| Fragment (C) | cat-FW | cat-FW | cat-FW | cat-FW | cat-FW | cat-FW |
| | upp-RV | upp-RV | upp-RV | upp-RV | upp-RV | upp-RV |
| Fragment (D) | Pro1-AFW | Pro3-AFW | Pro4-AFW | Pro7-AFW | PBSX-AFW | spB-AFW |
| | Pro1-BRV | Pro3-BRV | Pro4-BRV | Pro7-BRV | PBSX-BRV | spB-BRV |
| Fragment (E) | Pro1-AFW | Pro3-AFW | Pro4-AFW | Pro7-AFW | PBSX-AFW | spB-AFW |
| | Pro1-ERV | Pro3-ERV | Pro4-ERV | Pro7-ERV | PBSX-ERV | spB-ERV |
| Fragment (F) | Pro1-FFW | Pro3-FFW | Pro4-FFW | Pro7-FFW | PBSX-FFW | spB-FFW |
| | Pro1-BRV | Pro3-BRV | Pro4-BRV | Pro7-BRV | PBSX-BRV | spB-BRV |
| Fragment (G) | Pro1-AFW | Pro3-AFW | Pro4-AFW | Pro7-AFW | PBSX-AFW | spB-AFW |
| | Pro1-BRV | Pro3-BRV | Pro4-BRV | Pro7-BRV | PBSX-BRV | spB-BRV |

TABLE 3-continued

|  | Deletion target region | | | | | |
|---|---|---|---|---|---|---|
|  | pks | Pro2 | Pro5 | Pro6 | SKIN | pps |
| Fragment (A) | pks-AFW | Pro2-AFW | Pro5-AFW | Pro6-AFW | skin-AFW | pps-AFW |
|  | pks-ARV | Pro2-ARV | Pro5-ARV | Pro6-ARV | skin-ARV | pps-ARV |
| Fragment (B) | pks-BFW | Pro2-BFW | Pro5-BFW | Pro6-BFW | skin-BFW | pps-BFW |
|  | pks-BRV | Pro2-BRV | Pro5-BRV | Pro6-BRV | skin-BRV | pps-BRV |
| Fragment (C) | cat-FW | cat-FW | cat-FW | cat-FW | cat-FW | cat-FW |
|  | upp-RV | upp-RV | upp-RV | upp-RV | upp-RV | upp-RV |
| Fragment (D) | pks-AFW | Pro2-AFW | Pro5-AFW | Pro6-AFW | skin-AFW | pps-AFW |
|  | pks-BRV | Pro2-BRV | Pro5-BRV | Pro6-BRV | skin-BRV | pps-BRV |
| Fragment (E) | pks-AFW | Pro2-AFW | Pro5-AFW | Pro6-AFW | skin-AFW | pps-AFW |
|  | pks-ERV | Pro2-ERV | Pro5-ERV | Pro6-ERV | skin-ERV | pps-ERV |
| Fragment (F) | pks-FFW | Pro2-FFW | Pro5-FFW | Pro6-FFW | skin-FFW | pps-FFW |
|  | pks-BRV | Pro2-BRV | Pro5-BRV | Pro6-BRV | skin-BRV | pps-BRV |
| Fragment (G) | pks-AFW | Pro2-AFW | Pro5-AFW | Pro6-AFW | skin-AFW | pps-AFW |
|  | pks-BRV | Pro2-BRV | Pro5-BRV | Pro6-BRV | skin-BRV | pps-BRV |

<Construction of Multiple-Deficient Strains (MGB01 Strain to MGB07 Strain)>

Next, with the use of the ΔPro7 strain (also referred to as the MGB01 strain), a strain (multiple-deficient strain) lacking a plurality of regions was constructed. First, a double-deficient strain lacking Pro7 and Pro6 regions was constructed as follows. Specifically, the ΔPro7 strain was transformed by the competent method using the genomic DNA of the ΔPro6::cat-upp strain in which the Pro6 region had been substituted with a cat-upp cassette fragment. Colonies that had grown on LB agar medium containing 10 ppm chloramphenicol were separated as transformants. Next, the thus obtained chloramphenicol-resistant transformants were transformed by the competent method using the genomic DNA of the ΔPro6 strain. Thus, a strain capable of growing in Cg+ glucose agar medium supplemented with 1 μg/mL 5FU was obtained. The thus obtained strain was confirmed to be susceptible to chloramphenicol and to lack both Pro6 and Pro7 regions. Furthermore, a double-deficient strain lacking the cat-upp cassette fragment was separated. This strain was named the MGB02 strain.

Similar procedures were repeated, so that a MGB03 strain was constructed in which the Pro7 region, the Pro6 region, and the Pro1 region had been deleted in that order. Similar procedures were repeated, so that a MGB04 strain was constructed in which the Pro7 region, the Pro6 region, the Pro1 region, and the Pro4 region had been deleted in that order. Similar procedures were repeated, so that a MGB05 strain was constructed in which the Pro7 region, the Pro6 region, the Pro1 region, the Pro4 region, and the PBSX region had been deleted in that order. Similar procedures were repeated, so that a MGB06 strain was constructed in which the Pro7 region, the Pro6 region, the Pro1 region, the Pro4 region, the PBSX region, and the Pro5 region had been deleted in that order. Similar procedures were repeated, so that a MGB07 strain was constructed in which the Pro7 region, the Pro6 region, the Pro1 region, the Pro4 region, the PBSX region, the Pro5 region, and the Pro3 region had been deleted in that order.

<Preparation 2 of Each Single-Region-Deficient Strain>

With a method differing from that employed for the above-mentioned <preparation 1 of single-region-deficient strains>, an SPβ-region-deficient strain, a pks-region-deficient strain, an SKIN-region-deficient strain, a pps-region-deficient strain, a Pro2-region-deficient strain, a Pro5-region-deficient strain, an NED0302-region-deficient (ydcL-ydhU-region-deficient) strain, an NED0803-region-deficient (yisB-yitD-region-deficient) strain, an NED3200-region-deficient (yunA-yurt-region-deficient) strain, an NED1902-region-deficient (cgeE-ypmQ-region-deficient) strain, an NED0501-region-deficient (yeeK-yesX-region-deficient) strain, an NED0400-region-deficient (ydiM-yebA region-deficient) strain, an NED1100-region (ykuS-ykqB-region)-deficient strain, an NED4002-region-deficient (pdp-rocR-region-deficient) strain, an NED02021-region-deficient (ycxB-sipU-region-deficient) strain, a SKIN-Pro7-region-deficient (spoIVCB-yraK-region-deficient) strain, an NED3701-region-deficient (sbo-ywhH-region-deficient) strain, an NED0600-region-deficient (cspB-yhcT-region-deficient) strain, an NED4100-region-deficient (yybP-yyaJ-region-deficient) strain, an NED2702-region-deficient (ytxK-braB-region-deficient) strain, and an NED1602-region-deficient (yncM-fosB-region-deficient) strain were constructed.

Figure 6:
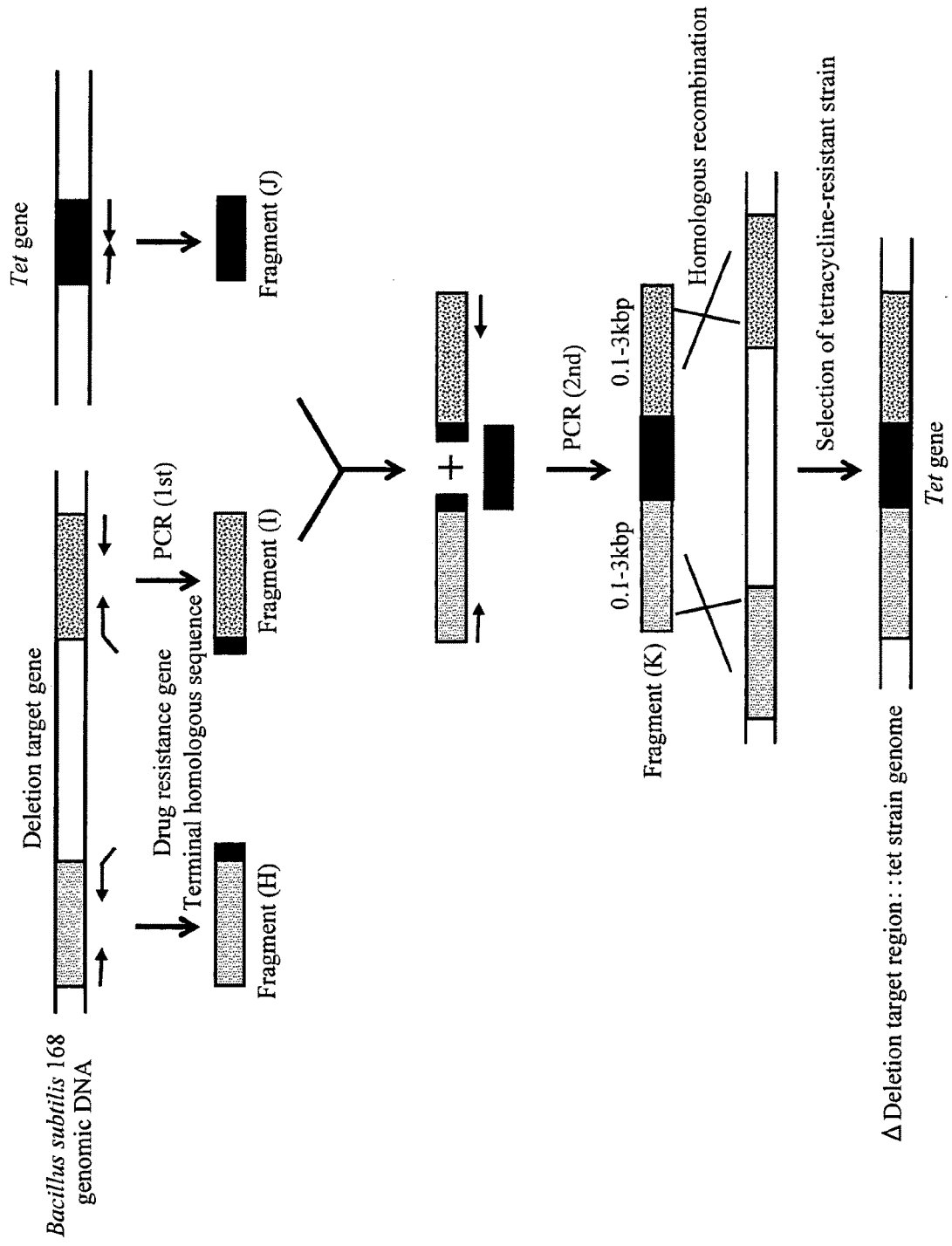
FIG. 6 is a schematic diagram for explanation of procedures for preparing a Δdeletion target region::tet strain.

An example of the construction of a strain lacking an SPβ region alone is described below. As shown in FIG. 6, a 0.6-kb fragment (H) adjacent upstream of the SPβ region and a 0.3-kb fragment (I) adjacent downstream of the same were prepared by PCR using a primer set of spB-AFW and spB-ARV2, a primer set of spB-BFW2 and spB-BRV, and the 168 strain genome as a template. In addition, in FIG. 6, SPβ is denoted as "deletion target region."

A tetracycline resistance gene region fragment (J) was amplified using a primer set of tet-FW and tet-RV. Subsequently, SOE-PCR was performed using the thus obtained PCR amplification fragments (H), (I), and (J) as templates and primers spB-AFW and spB-BRV, so that the three fragments were bound in the order of (H), (J), and (I). The above 168Δupp strain was transformed by the competent method using the thus obtained DNA fragment (K). Thus, transformants capable of growing in LB agar medium containing 15 ppm tetracycline were separated. It was confirmed that in the thus obtained transformants, the SPβ region had been deleted from the genome and substituted with the tetracycline resistance gene fragment as a result of PCR. The strain was designated the ΔSPβ::tet strain. In addition, in FIG. 6, the ΔSPβ::tet strain is denoted as the "Δdeletion target region::tet strain."

Similarly, strains each lacking a region described above were prepared. Each of the thus prepared strains is referred to as a "Δdeletion target region::tet strain" in the same manner as the ΔSPβ::tet strain.

<Deletion of the SPβ Region from the MGB07 Strain>

The ΔPro7 strain was transformed using the genomic DNA of the ΔSPβ::tet strain prepared above, so that a tetracycline-resistant MGB07ΔSPβ::tet strain was obtained. Meanwhile, the tetracycline resistance gene fragment was eliminated from the genome as described below.

Figure 7:
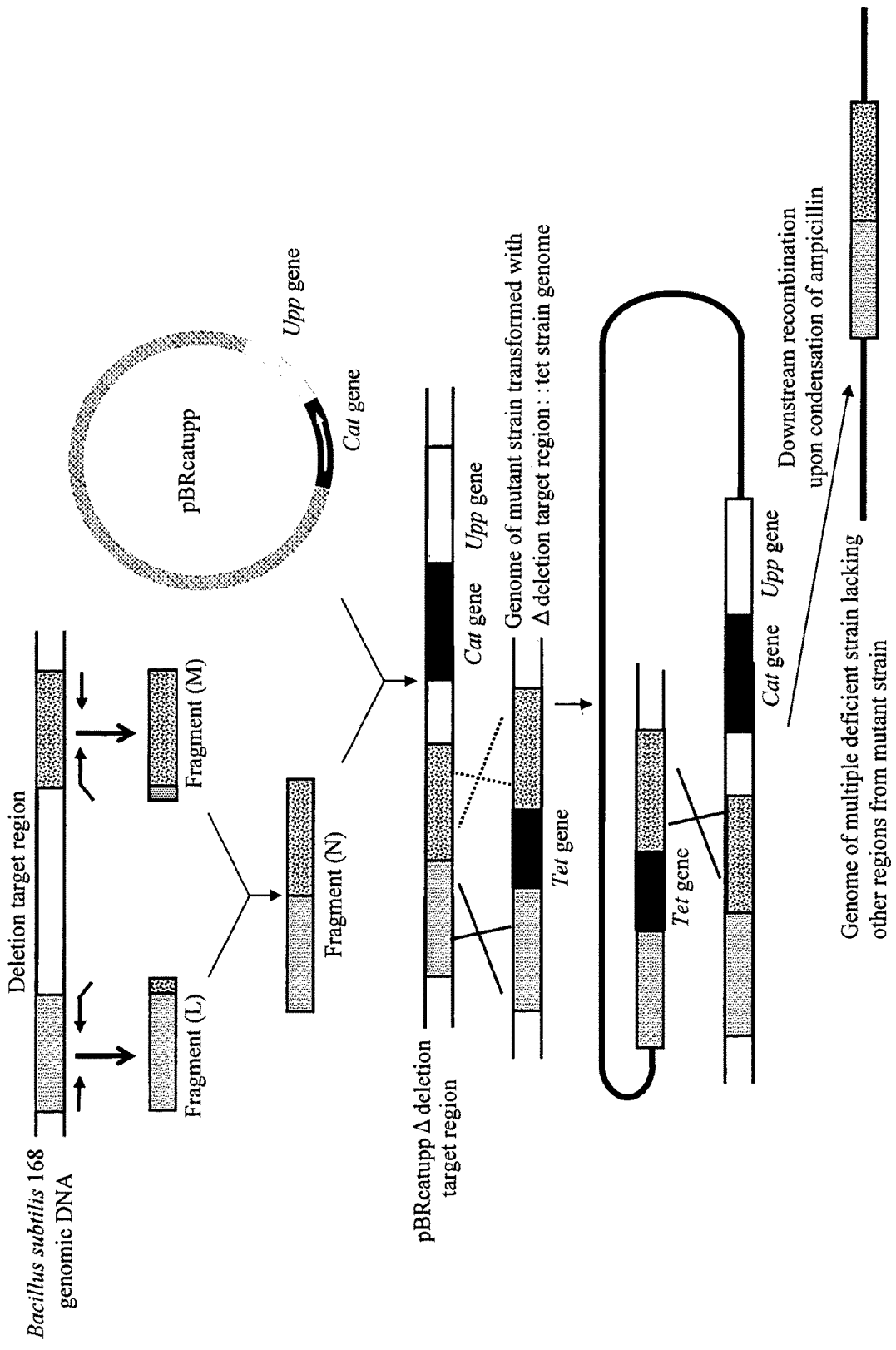
FIG. 7 is a schematic diagram for explanation of procedures for deleting a deletion target region in a predetermined mutant strain with the use of the pBRcatuppΔ deletion target region.

As shown in FIG. 7, a 0.6-kb fragment (L) adjacent upstream of the SPβ region and a 0.3-kb fragment (M) adjacent downstream of the same were prepared by PCR using a primer set of spB-AFW and spB-ERV, and a primer set of spB-FFW and spB-BRV, and the 168 strain genome as a template. In addition, in FIG. 7, SPβ is denoted as "deletion target region."

Subsequently, SOE-PCR was performed using the thus obtained PCR amplification fragments (L) and (M) as templates and primers spB-AFW and spB-BRV, so that the 2 fragments were bound in the order of (L) and (M). The thus obtained DNA fragment (N) was inserted into the sac I-Kpn I restriction enzyme site (blunt-ended after cleavage) of the above pBRcatupp, so that a plasmid pBRcatuppΔSPβ for elimination of the tetracycline resistance gene fragment was constructed. In addition, in FIG. 7, pBRcatuppΔSPβ is denoted as "pBRcatuppΔdeletion target region."

The MGB07ΔSPβ::tet strain was transformed with the constructed pBRcatuppΔSPβ. Single-crossover recombination took place between a region upstream or downstream of SPβ on the plasmid and a region upstream or downstream of SPβ on the genome, so that the plasmid is introduced onto the genome and a MGB07ΔSPβ (pBR) strain showing chloramphenicol resistance was obtained.

The thus obtained transformant MGB07ΔSPβ (pBR) strain was inoculated in 50 mL of LB medium (500-mL Sakaguchi flask) containing 1.5 μg/mL tetracycline to achieve OD600=0.3, followed by shake culture at 37° C. After one hour of shake culture, 15 mg of ampicillin (300 μg/mL) was added, and then culture was continued while adding 15 mg of ampicillin every 2 hours after addition. After 8.5 hours of culture, the culture solution was washed with a 2% sodium chloride aqueous solution and then drug-free LB agar medium was coated with the solution. Among colonies that had grown, colonies that had become susceptible to chloramphenicol along with the deletion of the plasmid region were selected.

PCR was performed using the genomic DNA of the selected bacterial strain as a template, so that deletion of the SPβ region and the tetracycline resistance gene fragment was confirmed. Thus, an MGB08 strain was obtained.

<Deletion of the pks Region from the MGB08 Strain and the Reversion of the Pro5 Region>

The pks region was deleted from the MGB08 strain prepared above according to the above method (FIG. 7) using the Δpks::tet strain. A strain prepared by deletion of the pks region from the MGB08 strain was named the MGB09 strain. The genomic DNA of the thus obtained MGB09 strain was confirmed by PCR. The pks region had been deleted, but the presence of a sequence within the Pro5 region located near the pks region on the genome was confirmed, demonstrating the reversion of the Pro5 region. This may be caused by, when the MGB08 strain was transformed using the genomic DNA of the Δpks::tet strain, homologous recombination that took place between: an upstream region of the pks region on the Δpks::tet strain genome and a downstream region of the Pro5 region on the same; and the corresponding regions on the MGB08 strain genome, simultaneously with introduction of the tetracycline resistance gene along with the deletion of the pks region.

<Deletion of the SKIN Region from the MGB09 Strain and Reversion of the Pro7 Region>

The SKIN region was deleted from the MGB09 strain prepared above according to the above method (FIG. 7) using a ΔSKIN::tet strain. A strain prepared by deletion of the SKIN region from the MGB09 strain was named the MGB10 strain. The genomic DNA of the thus obtained MGB10 strain was confirmed by PCR. The SKIN region had been deleted, but the presence of a sequence within the Pro7 region located near the SKIN region on the genome was confirmed, demonstrating the reversion of the Pro7 region. This may be caused by, when the MGB09 strain was transformed using the genomic DNA of the ΔSKIN::tet strain, homologous recombination that took place between: an upstream region of the SKIN region on the ΔSKIN::tet strain genome and a downstream region of the Pro7 region on the same; and the corresponding regions on the MGB09 strain genome, simultaneously with introduction of the tetracycline resistance gene along with the deletion of the SKIN region.

<Deletion of the pps Region from the MGB10 Strain>

The pps region was deleted from the MGB10 strain prepared above according to the above method (FIG. 7) using the Δpps::tet strain. A strain prepared by deletion of the pps region from the MGB10 strain was named the MGB11 strain. The genomic DNA of the thus obtained MGB1 strain was confirmed by PCR, and the pps region had been deleted without reversion of other regions.

<Deletion of the Pro2 Region from the MGB11 Strain>

The Pro2 region was deleted from the MGB11 strain prepared above according to the above method (FIG. 7) using the ΔPro2::tet strain. A strain prepared by deletion of the Pro2 region from the MGB11 strain was named the MGB12 strain. The genomic DNA of the thus obtained MGB12 strain was confirmed by PCR, and the Pro2 region had been deleted without reversion of other regions.

<Deletion of the Pro5 Region from the MGB12 Strain>

To delete again the Pro5 region that had undergone reversion upon preparation of the MGB09 strain, the Pro5 region was deleted from the MGB12 strain prepared above according to the above method (FIG. 7) using the ΔPro5::tet strain. A strain prepared by deletion of the Pro5 region from the MGB12 strain was named the MGB11d strain. The genomic DNA of the thus obtained MGB11d strain was confirmed by PCR, and the Pro5 region had been deleted without reversion of other regions.

The MGB11d strain prepared as described above had a genomic structure from which a Pro6 (yoaV-yobO) region, a Pro1 (ybbU-ybdE) region, a Pro4 (yjcM-yjdJ) region, a PBSX (ykdA-xlyA) region, a Pro5 (ynxB-dut) region, a Pro3 (ydiM-ydjC) region, an SPβ (yodU-ypqP) region, a pks (pksA-ymaC) region, a SKIN (spoIVCB-spoIIIC) region, a pps (ppsE-ppsA) region, and a Pro2 (ydcL-ydeJ) region of the *Bacillus subtilis* 168 strain had been deleted.

<Construction of *Bacillus subtilis* Mutant Strains According to the Present Invention>

Figure 8:
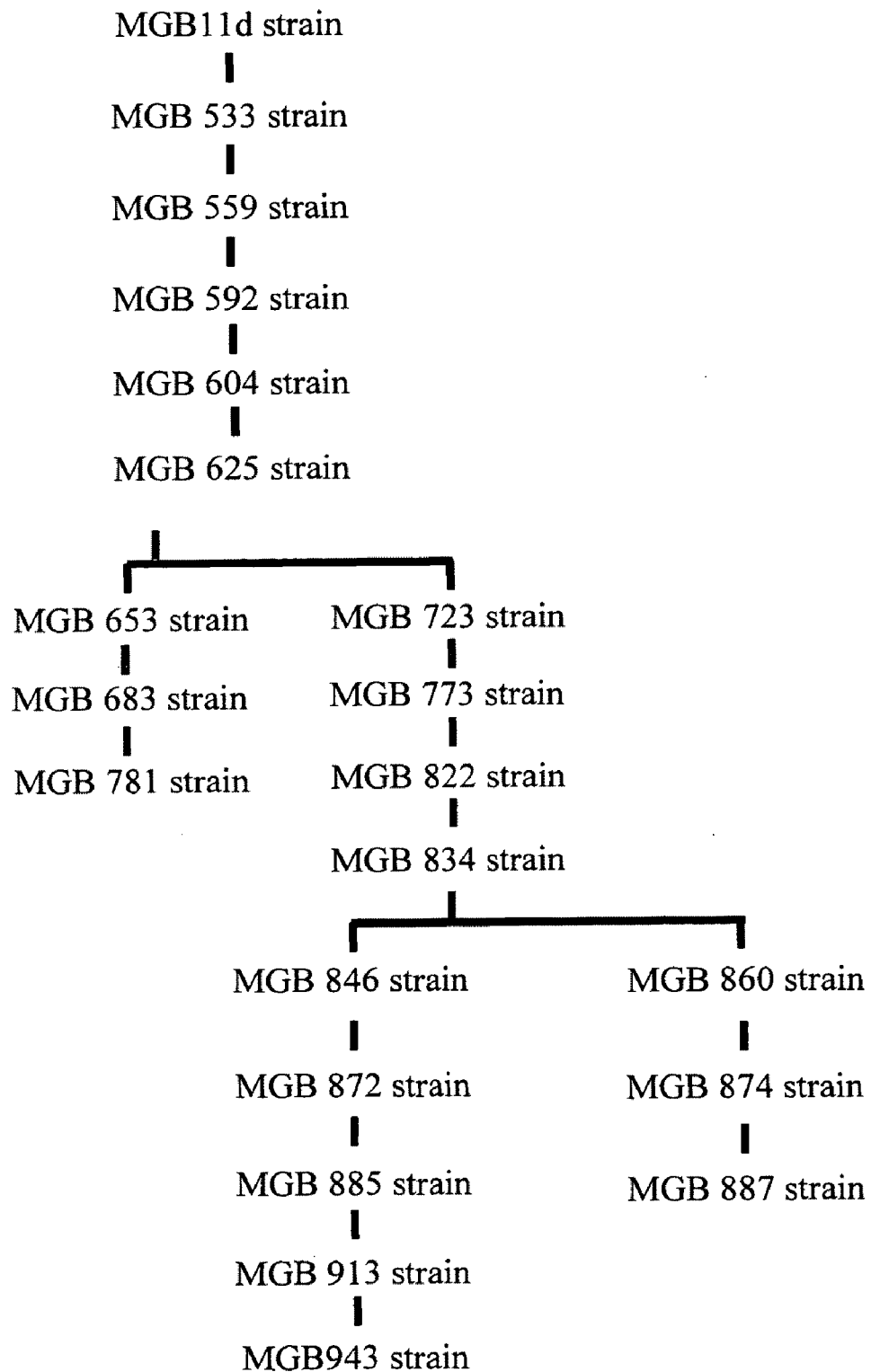
FIG. 8 is a schematic diagram for explanation of the processes employed for preparing a *Bacillus subtilis* mutant strain according to the present invention from which a plurality of deletion regions have been deleted.

*Bacillus subtilis* mutant strains according to the present invention were prepared from the MGB11d strain prepared as described above (see FIG. 8). Specifically, an NED0302 region was deleted from the MGB11d strain according to the above method (FIG. 7) using a ΔNED0302::tet strain. A strain prepared by deletion of the NED0302 region from the MGB11d strain was named the MGB533 strain. The thus obtained MGB533 strain had a genomic structure from which the NED0302 region had been deleted, in addition to deleted regions in the MGB11d strain.

Subsequently, the NED0803 region, the NED3200 region, the NED1902 region, the NED0501 region, the NED0400 region, the NED1100 region, and the NED4002 region were deleted in that order, so that mutant strains were constructed. The thus constructed mutant strains were named the MGB559 strain, MGB592 strain, MGB604 strain, MGB625 strain, MGB653 strain, MGB683 strain, and MGB781 strain, respectively.

In addition, the NED3200 region contained the Pro2 region. A ydeK-ydhU region had actually been deleted from the MGB559 strain upon construction of the MGB592 strain. Moreover, the NED1902 region contained the SPβ region. Regions that had actually been deleted from the MGB592 strain upon construction of the MGB604 strain were the cgeE-phy and yppQ-ypmQ regions. Similarly, the NED0400 region contained the Pro3 region. A gutR-yebA region had actually been deleted from the MGB625 strain upon construction of the MGB653 strain.

Next, the NED40002 region was deleted from the constructed MGB625 strain according to the above method (FIG. 7) using a ΔNED40002::tet strain. A strain prepared by deletion of the NED40002 region from the MGB625 strain was named the MGB723 strain.

Subsequently, the NED02021 region, the SKIN-Pro7 region, the NED3701 region, the NED0600 region, the NED4100 region, the NED2702 region, the NED0400 region, and the NED1100 region were deleted in that order, so that mutant strains were constructed. The thus constructed mutant strains were named the MGB773 strain, MGB822 strain, MGB834 strain, MGB846 strain, MGB872 strain, MGB885 strain, MGB913 strain, and MGB943 strain, respectively.

In addition, the SKIN-Pro7 region contained the SKIN region. A yrkS-yraK region had actually been deleted from the MGB773 strain upon construction of the MGB822 strain. Similarly, NED0400 contained the Pro3 region, a gutR-yebA region had actually been deleted from the MGB885 strain upon construction of the MGB913 strain.

Next, the NED4100 region was deleted from the constructed MGB834 strain according to the above method (FIG. 7) using a ΔNED4100::tet strain. A strain prepared by deletion of the NED4100 region from the MGB834 strain was named the MGB860 strain.

Subsequently, mutant strains were constructed by deletion of the NED1602 region and the NED2702 region in that order. The thus constructed mutant strains were named the MGB874 strain and the MGB887 strain, respectively.

Primer sets used for amplification of fragments (H) to (N) in the steps for preparation of each of these strains are listed in Table 4 below.

TABLE 4

| | \multicolumn{8}{c}{Deletion target region} | | | | | | | |
|---|---|---|---|---|---|---|---|---|
| | SPβ | pks | SKIN | pps | Pro2 | Pro5 | NED02021 | NED0302 |
| Fragment (H) | spB-AFW<br>spB-ARV2 | pks-AFW<br>pks-ARV2 | skin-AFW<br>skin-ARV2 | pps-AFW<br>pps-ARV2 | pro2-AFW<br>pro2-ARV2 | pro5-AFW<br>pro5-ARV2 | NED0202-AFW<br>NED0202-ARV | NED0302-AFW<br>NED0302-ARV |
| Fragment (I) | spB-BFW2<br>spB-BRV | pks-BFW2<br>pks-BRV | skin-BFW2<br>skin-BRV | pps-BFW2<br>pps-BRV | pro2-BFW2<br>pro2-BRV | pro5-BFW2<br>pro5-BRV | NED02021-BFW<br>NED02021-BRV | NED0302-BFW<br>NED0302-BRV |
| Fragment (J) | tet-FW<br>tet-RV | tet-FW<br>tet-RV | tet-FW<br>tet-RV | tet-FW<br>tet-RV | tet-FW<br>tet-RV | tet-FW<br>tet-RV | tet-FW<br>tet-RV | tet-FW<br>tet-RV |
| Fragment (K) | spB-AFW<br>spB-BRV | pks-AFW<br>pks-BRV | skin-AFW<br>skin-BRV | pps-AFW<br>pps-BRV | pro2-AFW<br>pro2-BRV | pro5-AFW<br>pro5-BRV | NED0202-AFW<br>NED02021-BRV | NED0302-AFW<br>NED0302-BRV |
| Fragment (L) | spB-AFW<br>spB-ERV | pks-AFW<br>pks-ERV | skin-AFW<br>skin-ERV | pps-AFW<br>pps-ERV | pro2-AFW<br>pro2-ERV | pro5-AFW<br>pro5-ERV | NED0202-AFW<br>NED02021-ERV | NED0302-AFW<br>NED0302-ERV |
| Fragment (M) | spB-FFW<br>spB-BRV | pks-FFW<br>pks-BRV | skin-FFW<br>skin-BRV | pps-FFW<br>pps-BRV | pro2-FFW<br>pro2-BRV | pro5-FFW<br>pro5-BRV | NED02021-FFW<br>NED02021-BRV | NED0302-FFW<br>NED0302-BRV |
| Fragment (N) | spB-AFW<br>spB-BRV | pks-AFW<br>pks-BRV | skin-AFW<br>skin-BRV | pps-AFW<br>pps-BRV | pro2-AFW<br>pro2-BRV | pro5-AFW<br>pro5-BRV | NED0202-AFW<br>NED02021-BRV | NED0302-AFW<br>NED0302-BRV |

| | \multicolumn{7}{c}{Deletion target region} | | | | | | |
|---|---|---|---|---|---|---|---|
| | NED0400 | NED0501 | NED0600 | NED1602 | NED1902 | SKIN-Pro7 | NED2702 |
| Fragment (H) | NED0400-AFW<br>NED0400-ARV | NED0501-AFW<br>NED0501-ARV | NED0600-AFW<br>NED0600-ARV | NED1602-AFW<br>NED1602-ARV | NED1902-AFW<br>NED1902-ARV | skin-AFW<br>skin-ARV2 | NED2702-AFW<br>NED2702-ARV |
| Fragment (I) | NED0400-BFW<br>NED0400-BRV | NED0501-BFW<br>NED0501-BRV | NED0600-BFW<br>NED0600-BRV | NED1602-BFW<br>NED1602-BRV | NED1902-BFW<br>NED1902-BRV | Pro7-BFW2<br>Pro7-BRV | NED2702-BFW<br>NED2702-BRV |
| Fragment (J) | tet-FW<br>tet-RV | tet-FW<br>tet-RV | tet-FW<br>tet-RV | tet-FW<br>tet-RV | tet-FW<br>tet-RV | tet-FW<br>tet-RV | tet-FW<br>tet-RV |
| Fragment (K) | NED0400-AFW<br>NED0400-BRV | NED0501-AFW<br>NED0501-BRV | NED0600-AFW<br>NED0600-BRV | NED1602-AFW<br>NED1602-BRV | NED1902-AFW<br>NED1902-BRV | skin-AFW<br>Pro7-BRV | NED2702-AFW<br>NED2702-BRV |
| Fragment (L) | NED0400-AFW<br>NED0400-ERV | NED0501-AFW<br>NED0501-ERV | NED0600-AFW<br>NED0600-ERV | NED1602-AFW<br>NED1602-ERV | NED1902-AFW<br>NED1902-ERV | skin-AFW<br>skin-ERV2 | NED2702-AFW<br>NED2702-ERV |
| Fragment (M) | NED0400-FFW<br>NED0400-BRV | NED0501-FFW<br>NED0501-BRV | NED0600-FFW<br>NED0600-BRV | NED1602-FFW<br>NED1602-BRV | NED1902-FFW<br>NED1902-BRV | Pro7-FFW2<br>Pro7-BRV | NED2702-FFW<br>NED2702-BRV |
| Fragment (N) | NED0400-AFW<br>NED0400-BRV | NED0501-AFW<br>NED0501-BRV | NED0600-AFW<br>NED0600-BRV | NED1602-AFW<br>NED1602-BRV | NED1902-AFW<br>NED1902-BRV | skin-AFW<br>Pro7-BRV | NED2702-AFW<br>NED2702-BRV |

| | \multicolumn{6}{c}{Deletion target region} | | | | | |
|---|---|---|---|---|---|---|
| | NED3701 | NED40002 | NED4100 | NED0803 | NED1100 | NED3200 |
| Fragment (H) | NED3701-AFW<br>NED3701-ARV | NED40002-AFW<br>NED40002-ARV | NED4100-AFW<br>NED4100-ARV | NED0803-AFW<br>NED0803-ARV | NED1100-AFW<br>NED1100-ARV | NED3200-AFW<br>NED3200-ARV |
| Fragment (I) | NED3701-BFW<br>NED3701-BRV | NED40002-BFW<br>NED40002-BRV | NED4100-BFW<br>NED4100-BRV | NED0803-BFW<br>NED0803-BRV | NED1100-BFW<br>NED1100-BRV | NED3200-BFW<br>NED3200-BRV |
| Fragment (J) | tet-FW<br>tet-RV | tet-FW<br>tet-RV | tet-FW<br>tet-RV | tet-FW<br>tet-RV | tet-FW<br>tet-RV | tet-FW<br>tet-RV |
| Fragment (K) | NED3701-AFW<br>NED3701-BRV | NED40002-AFW<br>NED40002-BRV | NED4100-AFW<br>NED4100-BRV | NED0803-AFW<br>NED0803-BRV | NED1100-AFW<br>NED1100-BRV | NED3200-AFW<br>NED3200-BRV |
| Fragment (L) | NED3701-AFW<br>NED3701-ERV | NED40002-AFW<br>NED40002-ERV | NED4100-AFW<br>NED4100-ERV | NED0803-AFW<br>NED0803-ERV | NED1100-AFW<br>NED1100-ERV | NED3200-AFW<br>NED3200-ERV |

TABLE 4-continued

| | | | | | | |
|---|---|---|---|---|---|---|
| Fragment (M) | NED3701-FFW | NED40002-FFW | NED4100-FFW | NED0803-FFW | NED1100-FFW | NED3200-FFW |
| | NED3701-BRV | NED40002-BRV | NED4100-BRV | NED0803-BRV | NED1100-BRV | NED3200-BRV |
| Fragment (N) | NED3701-AFW | NED40002-AFW | NED4100-AFW | NED0803-AFW | NED1100-AFW | NED3200-AFW |
| | NED3701-BRV | NED40002-BRV | NED4100-BRV | NED0803-BRV | NED1100-BRV | NED3200-BRV |

Example 2

Mutant Strains Each Lacking a Single Region

In this example, each specific region of the *Bacillus subtilis* 168 strain was substituted with a cat-upp cassette or a chloramphenicol resistance gene, so that mutant strains each lacking the specific region were prepared.
<Construction of Single-Region-Deficient Strains Via Substitution with the cat-upp Cassette>
Regions to be subjected to substitution with the cat-upp cassette are as listed in Table 5 below.

TABLE 5

| Name | Deletion target region |
|---|---|
| NED0100 | ybbU-yceK |
| NED0202 | ycxB-ydbP |
| NED0302 | ydcL-ydhU |
| NED0802 | yhxD-yhjP |
| NED0803 | yisB-yitD |
| NED0804 | yitH-yitZ |
| NED0900 | oppA-yjbK |
| NED1400 | gid-ylxL |

TABLE 5-continued

| Name | Deletion target region |
|---|---|
| NED1500 | spoVS-ymzA |
| NED1802 | yoxC-yocS |
| NED2500 | yqeD-yrzL |
| NED3402 | yvdM-yvcP |
| NED4000 | dltA-rocR |

In addition, the NED0100 region contained the Pro1 region. The NED0302 region contained the Pro2 region, the NED1500 region contained the pks region, the NED1802 region contained the Pro6 region, and the NED2500 region contained the SKIN-Pro7 region.

In this example, mutant strains were constructed via substitution of specific regions with the cat-upp cassette fragment prepared in Example 1 according to the method described in FIG. 4. Furthermore, in this example, fragment (A), fragment (B), fragment (C), and fragment (D) in FIG. 4 are referred to as fragment (O), fragment (P), fragment (Q), and fragment (R), respectively. Primer sets used for amplification of fragments (P) to (R) in the steps for preparation of each of these strains are listed in Table 6 below.

TABLE 6

| | Deletion target region | | | | |
|---|---|---|---|---|---|
| | Pro1 | NED0100 | NED0202 | NED0302 | NED0802 |
| Fragment (O) | Pro1-AFW | NED0100-AFW | NED0202-AFW | NED0302-AFW | NED0802-AFW |
| | Pro1-ARV | NED0100-ARV | NED0202-ARV | NED0302-ARV2 | NED0802-ARV |
| Fragment (P) | Pro1-BFW | NED0100-BFW | NED0202-BFW | NED0302-BFW2 | NED0802-BFW |
| | Pro1-BRV | NED0100-BRV | NED0202-BRV | NED0302-BRV | NED0802-BRV |
| Fragment (Q) | cat-FW | cat-FW | cat-FW | cat-FW | cat-FW |
| | upp-RV | upp-RV | upp-RV | upp-RV | upp-RV |
| Fragment (R) | Pro1-AFW | NED0100-AFW | NED0202-AFW | NED0302-AFW | NED0802-AFW |
| | Pro1-BRV | NED0100-BRV | NED0202-BRV | NED0302-BRV | NED0802-BRV |

| | Deletion target region | | | | |
|---|---|---|---|---|---|
| | NED0803 | NED0804 | NED0900 | NED1002 | NED1400 |
| Fragment (O) | NED0803-AFW | NED0804-AFW | NED0900-AFW | NED1002-AFW | NED1400-AFW |
| | NED0803-ARV | NED0804-ARV | NED0900-ARV | NED1002-ARV | NED1400-ARV |
| Fragment (P) | NED0803-BFW | NED0804-BFW | NED0900-BFW | NED1002-BFW | NED1400-BFW |
| | NED0803-BRV | NED0804-BRV | NED0900-BRV | NED1002-BRV | NED1400-BRV |
| Fragment (Q) | cat-FW | cat-FW | cat-FW | cat-FW | cat-FW |
| | upp-RV | upp-RV | upp-RV | upp-RV | upp-RV |
| Fragment (R) | NED0803-AFW | NED0804-AFW | NED0900-AFW | NED1002-AFW | NED1400-AFW |
| | NED0803-BRV | NED0804-BRV | NED0900-BRV | NED1002-BRV | NED1400-BRV |

| | Deletion target region | | | |
|---|---|---|---|---|
| | NED1500 | NED2500 | NED3402 | NED4000 |
| Fragment (O) | NED1500-AFW | NED2500-AFW | NED3402-AFW | NED4000-AFW |
| | NED1500-ARV | NED2500-ARV | NED3402-ARV | NED4000-ARV |
| Fragment (P) | NED1500-BFW | NED2500-BFW | NED3402-BFW | NED4000-BFW |
| | NED1500-BRV | NED2500-BRV | NED3402-BRV | NED4000-BRV |
| Fragment (Q) | cat-FW | cat-FW | cat-FW | cat-FW |
| | upp-RV | upp-RV | upp-RV | upp-RV |
| Fragment (R) | NED1500-AFW | NED2500-AFW | NED3402-AFW | NED4000-AFW |
| | NED1500-BRV | NED2500-BRV | NED3402-BRV | NED4000-BRV |

<Construction of Single-region-deficient Strains Via Substitution with a Chloramphenicol Resistance Gene>

Substitution of a region with a chloramphenicol resistance gene was performed by substituting a target region with a tetracycline resistance gene and then substituting the central portion of the tetracycline resistance gene with a chloramphenicol resistance gene. Regions subjected to substitution with a chloramphenicol resistance gene are listed in Table 7 below.

TABLE 7

| Name | Deletion target region |
| --- | --- |
| NED0301 | ydcD-ydcK |
| NED0400 | ydiM-yebA |
| NED0501 | yeeK-yesX |
| NED0600 | cspB-yhcT |
| NED0700 | yhdP-yhaL |
| NED1002 | yjcM-yjgB |
| NED1003 | yjqB-htrA |
| NED1100 | ykuS-ykqB |
| NED1200 | slp-ylaM |
| NED1300 | ctaA-ylbE |
| NED1602 | yncM-fosB |
| NED1901 | yojO-yozE |
| NED1902 | cgeE-ypmQ |
| NED2201 | ypzC-drm |
| NED2202 | yqxK-yqjP |
| NED2300 | zwf-yqzF |
| NED2402 | yqgZ-yqgN |
| NED2602 | yrzF-yrxA |
| NED2702 | ytxK-braB |
| NED2802 | ytzH-ytbQ |
| NED2900 | ytvB-ytoA |
| NED3000 | pckA-mntA |
| NED3200 | yunA-yurT |
| NED3301 | yurZ-yuxN |
| NED3303 | smpB-yvbK |
| NED3701 | sbo-ywhH |
| NED3800 | ywcB-ywaE |
| NED4001 | dltA-hutM |
| NED4002 | pdp-rocR |
| NED4100 | yybP-yyaJ |

In addition, the NED0400 region contained the Pro3 region, the NED1002 region contained the Pro4 region, NED1003 region contained the PBSX region, and the NED1902 region contained the SPβ region.

First, a method for deleting the NED0301 region is as explained below. A 0.6-kb fragment (S) adjacent upstream of the NED0301 region and a 0.3-kb fragment (T) adjacent downstream of the same were amplified by PCR using a primer set of NED0301-AFW and NED0301-ARV, a primer set of NED0301-BFW and NED0301-BRV, and the 168 strain genome as a template. Furthermore, a tetracycline resistance gene region fragment (U) was amplified using a primer set of tet-FW and tet-RV. Subsequently, SOE-PCR was performed using the thus obtained PCR amplification fragments (S), (T), and (U) as templates and primers NED0301-AFW and NED0301-BRV. Thus, a fragment (V) was obtained in which the three fragments were bound in the order of (S), (U), and (T). The 168Δupp strain prepared in Example 1 was transformed by the competent method using the thus obtained fragment (V). Transformants capable of growing in LB agar medium containing 15 ppm tetracycline were separated. It was confirmed that in the thus obtained transformants the NED0301 region had been deleted from the genome and substituted with the tetracycline resistance gene fragment as a result of PCR. Next, a 0.5-kb fragment (W) on the upstream side of the tetracycline resistance gene and a 0.5-kb fragment (X) on the downstream side of the same were amplified using a primer set of tet-FW and tet-ARV and a primer set of tet-BFW and tet-RV. Furthermore, a 1.3-kb fragment (Y) containing a chloramphenicol resistance gene was amplified using a plasmid pSM5022 (used in Example 1) as a template, cat-FW, and cat-RV. Subsequently, SOE-PCR was performed using the thus obtained PCR amplification fragments (W), (X), and (Y) as templates and primers tet-FW and tet-RV. Thus, a fragment (Z) was obtained, in which three fragments were bound in the order of (W), (Y), and (X). The above tetracycline-resistant strain was transformed by the competent method using the thus obtained fragment (Z). Thus, transformants capable of growing on LB agar medium containing 10 ppm chloramphenicol were separated. It was confirmed that in the thus obtained transformants a portion of the tetracycline resistance gene had been deleted and substituted with the chloramphenicol resistance gene as a result of PCR. A bacterial strain lacking the NED0301 region was named NED0301 strain.

Similarly, mutant strains each lacking a region listed in Table 7 above were prepared. Each of the thus prepared strains is named in the same manner as that for the NED0301 strain. Primer sets used for amplification of fragments (S) to (V) in the steps for preparation of each of these strains are listed in Table 8 below.

TABLE 8

| | Deletion target region | | | | | | |
| --- | --- | --- | --- | --- | --- | --- | --- |
| | NED0301 | NED0400 | NED0501 | NED0600 | NED0700 | NED1003 | NED1100 |
| Fragment (S) | NED0301-AFW | NED0400-AFW | NED0501-AFW | NED0600-AFW | NED0700-AFW | NED1003-AFW | NED1100-AFW |
| | NED0301-ARV | NED0400-ARV2 | NED0501-ARV2 | NED0600-ARV2 | NED0700-ARV | NED1003-ARV | NED1100-ARV |
| Fragment (T) | NED0301-BFW | NED0400-BFW | NED0501-BFW2 | NED0600-BFW2 | NED0700-BFW | NED1003-BFW | NED1100-BFW |
| | NED0301-BRV | NED0400-BRV | NED0501-BRV | NED0600-BRV | NED0700-BRV | NED1003-BRV | NED1100-BRV |
| Fragment (U) | tet-FW | tet-FW | tet-FW | tet-FW | tet-FW | tet-FW | tet-FW |
| | tet-RV | tet-RV | tet-RV | tet-RV | tet-RV | tet-RV | tet-RV |
| Fragment (V) | NED0301-AFW | NED0400-AFW | NED0501-AFW | NED0600-AFW | NED0700-AFW | NED1003-AFW | NED1100-AFW |
| | NED0301-BRV | NED0400-BRV | NED0501-BRV | NED0600-BRV | NED0700-BRV | NED1003-BRV | NED1100-BRV |
| Fragment (W) | tet-FW | tet-FW | tet-FW | tet-FW | tet-FW | tet-FW | tet-FW |
| | tet-ARV | tet-ARV | tet-ARV | tet-ARV | tet-ARV | tet-ARV | tet-ARV |
| Fragment (X) | tet-BFW | tet-BFW | tet-BFW | tet-BFW | tet-BFW | tet-BFW | tet-BFW |
| | tet-RV | tet-RV | tet-RV | tet-RV | tet-RV | tet-RV | tet-RV |
| Fragment (Y) | cat-FW | cat-FW | cat-FW | cat-FW | cat-FW | cat-FW | cat-FW |
| | cat-RV | cat-RV | cat-RV | cat-RV | cat-RV | cat-RV | cat-RV |
| Fragment (Z) | tet-FW | tet-FW | tet-FW | tet-FW | tet-FW | tet-FW | tet-FW |
| | tet-RV | tet-RV | tet-RV | tet-RV | tet-RV | tet-RV | tet-RV |

TABLE 8-continued

| | \multicolumn{6}{c}{Deletion target region} | | | | | |
|---|---|---|---|---|---|---|
| | NED1200 | NED1300 | NED1602 | NED1802 | NED1901 | NED1902 |
| Fragment (S) | NED1200-AFW<br>NED1200-ARV | NED1300-AFW<br>NED1300-ARV | NED1602-AFW<br>NED1602-ARV2 | NED1802-AFW<br>NED1802-ARV | NED1901-AFW<br>NED1901-ARV | NED1902-AFW<br>NED1902-ARV |
| Fragment (T) | NED1200-BFW<br>NED1200-BRV | NED1300-BFW<br>NED1300-BRV | NED1602-BFW2<br>NED1602-BRV | NED1802-BFW<br>NED1802-BRV | NED1901-BFW<br>NED1901-BRV | NED1902-BFW<br>NED1902-BRV |
| Fragment (U) | tet-FW<br>tet-RV | tet-FW<br>tet-RV | tet-FW<br>tet-RV | tet-FW<br>tet-RV | tet-FW<br>tet-RV | tet-FW<br>tet-RV |
| Fragment (V) | NED1200-AFW<br>NED1200-BRV | NED1300-AFW<br>NED1300-BRV | NED1602-AFW<br>NED1602-BRV | NED1802-AFW<br>NED1802-BRV | NED1901-AFW<br>NED1901-BRV | NED1902-AFW<br>NED1902-BRV |
| Fragment (W) | tet-FW<br>tet-ARV | tet-FW<br>tet-ARV | tet-FW<br>tet-ARV | tet-FW<br>tet-ARV | tet-FW<br>tet-ARV | tet-FW<br>tet-ARV |
| Fragment (X) | tet-BFW<br>tet-RV | tet-BFW<br>tet-RV | tet-BFW<br>tet-RV | tet-BFW<br>tet-RV | tet-BFW<br>tet-RV | tet-BFW<br>tet-RV |
| Fragment (Y) | cat-FW<br>cat-RV | cat-FW<br>cat-RV | cat-FW<br>cat-RV | cat-FW<br>cat-RV | cat-FW<br>cat-RV | cat-FW<br>cat-RV |
| Fragment (Z) | tet-FW<br>tet-RV | tet-FW<br>tet-RV | tet-FW<br>tet-RV | tet-FW<br>tet-RV | tet-FW<br>tet-RV | tet-FW<br>tet-RV |

| | \multicolumn{6}{c}{Deletion target region} | | | | | |
|---|---|---|---|---|---|---|
| | NED2201 | NED2202 | NED2300 | NED2402 | NED2602 | NED2701 |
| Fragment (S) | NED2201-AFW<br>NED2201-ARV | NED2202-AFW<br>NED2202-ARV | NED2300-AFW<br>NED2300-ARV | NED2402-AFW<br>NED2402-ARV | NED2602-AFW<br>NED2602-ARV | NED2701-AFW<br>NED2701-ARV |
| Fragment (T) | NED2201-BFW<br>NED2201-BRV | NED2202-BFW<br>NED2202-BRV | NED2300-BFW<br>NED2300-BRV | NED2402-BFW<br>NED2402-BRV | NED2602-BFW<br>NED2602-BRV | NED2701-BFW<br>NED2701-BRV |
| Fragment (U) | tet-FW<br>tet-RV | tet-FW<br>tet-RV | tet-FW<br>tet-RV | tet-FW<br>tet-RV | tet-FW<br>tet-RV | tet-FW<br>tet-RV |
| Fragment (V) | NED2201-AFW<br>NED2201-BRV | NED2202-AFW<br>NED2202-BRV | NED2300-AFW<br>NED2300-BRV | NED2402-AFW<br>NED2402-BRV | NED2602-AFW<br>NED2602-BRV | NED2701-AFW<br>NED2701-BRV |
| Fragment (W) | tet-FW<br>tet-ARV | tet-FW<br>tet-ARV | tet-FW<br>tet-ARV | tet-FW<br>tet-ARV | tet-FW<br>tet-ARV | tet-FW<br>tet-ARV |
| Fragment (X) | tet-BFW<br>tet-RV | tet-BFW<br>tet-RV | tet-BFW<br>tet-RV | tet-BFW<br>tet-RV | tet-BFW<br>tet-RV | tet-BFW<br>tet-RV |
| Fragment (Y) | cat-FW<br>cat-RV | cat-FW<br>cat-RV | cat-FW<br>cat-RV | cat-FW<br>cat-RV | cat-FW<br>cat-RV | cat-FW<br>cat-RV |
| Fragment (Z) | tet-FW<br>tet-RV | tet-FW<br>tet-RV | tet-FW<br>tet-RV | tet-FW<br>tet-RV | tet-FW<br>tet-RV | tet-FW<br>tet-RV |

| | \multicolumn{6}{c}{Deletion target region} | | | | | |
|---|---|---|---|---|---|---|
| | NED2702 | NED2802 | NED2900 | NED3000 | NED3100 | NED3200 |
| Fragment (S) | NED2702-AFW<br>NED2702-ARV | NED2802-AFW<br>NED2802-ARV | NED2900-AFW<br>NED2900-ARV | NED3000-AFW<br>NED3000-ARV | NED3100-AFW<br>NED3100-ARV | NED3200-AFW<br>NED3200-ARV2 |
| Fragment (T) | NED2702-BFW2<br>NED2702-BRV2 | NED2802-BFW<br>NED2802-BRV | NED2900-BFW<br>NED2900-BRV | NED3000-BFW<br>NED3000-BRV | NED3100-BFW<br>NED3100-BRV | NED3200-BFW2<br>NED3200-BRV |
| Fragment (U) | tet-FW<br>tet-RV | tet-FW<br>tet-RV | tet-FW<br>tet-RV | tet-FW<br>tet-RV | tet-FW<br>tet-RV | tet-FW<br>tet-RV |
| Fragment (V) | NED2702-AFW<br>NED2702-BRV | NED2802-AFW<br>NED2802-BRV | NED2900-AFW<br>NED2900-BRV | NED3000-AFW<br>NED3000-BRV | NED3100-AFW<br>NED3100-BRV | NED3200-AFW<br>NED3200-BRV |
| Fragment (W) | tet-FW<br>tet-ARV | tet-FW<br>tet-ARV | tet-FW<br>tet-ARV | tet-FW<br>tet-ARV | tet-FW<br>tet-ARV | tet-FW<br>tet-ARV |
| Fragment (X) | tet-BFW<br>tet-RV | tet-BFW<br>tet-RV | tet-BFW<br>tet-RV | tet-BFW<br>tet-RV | tet-BFW<br>tet-RV | tet-BFW<br>tet-RV |
| Fragment (Y) | cat-FW<br>cat-RV | cat-FW<br>cat-RV | cat-FW<br>cat-RV | cat-FW<br>cat-RV | cat-FW<br>cat-RV | cat-FW<br>cat-RV |
| Fragment (Z) | tet-FW<br>tet-RV | tet-FW<br>tet-RV | tet-FW<br>tet-RV | tet-FW<br>tet-RV | tet-FW<br>tet-RV | tet-FW<br>tet-RV |

| | \multicolumn{6}{c}{Deletion target region} | | | | | |
|---|---|---|---|---|---|---|
| | NED3301 | NED3303 | NED3701 | NED3800 | NED40001 | NED4100 |
| Fragment (S) | NED3301-AFW<br>NED3301-ARV | NED3303-AFW<br>NED3303-ARV | NED3701-AFW<br>NED3701-ARV2 | NED3800-AFW<br>NED3800-ARV | NED40001-AFW<br>NED40001-ARV | NED4100-AFW<br>NED4100-ARV2 |
| Fragment (T) | NED3301-BFW<br>NED3301-BRV | NED3303-BFW<br>NED3303-BRV | NED3701-BFW2<br>NED3701-BRV | NED3800-BFW<br>NED3800-BRV | NED40001-BFW<br>NED40001-BRV | NED4100-BFW2<br>NED4100-BRV |
| Fragment (U) | tet-FW<br>tet-RV | tet-FW<br>tet-RV | tet-FW<br>tet-RV | tet-FW<br>tet-RV | tet-FW<br>tet-RV | tet-FW<br>tet-RV |
| Fragment (V) | NED3301-AFW<br>NED3301-BRV | NED3303-AFW<br>NED3303-BRV | NED3701-AFW<br>NED3701-BRV | NED3800-AFW<br>NED3800-BRV | NED40001-AFW<br>NED40001-BRV | NED4100-AFW<br>NED4100-BRV |
| Fragment (W) | tet-FW<br>tet-ARV | tet-FW<br>tet-ARV | tet-FW<br>tet-ARV | tet-FW<br>tet-ARV | tet-FW<br>tet-ARV | tet-FW<br>tet-ARV |
| Fragment (X) | tet-BFW<br>tet-RV | tet-BFW<br>tet-RV | tet-BFW<br>tet-RV | tet-BFW<br>tet-RV | tet-BFW<br>tet-RV | tet-BFW<br>tet-RV |

TABLE 8-continued

| Fragment (Y) | cat-FW | cat-FW | cat-FW | cat-FW | cat-FW | cat-FW |
| | cat-RV | cat-RV | cat-RV | cat-RV | cat-RV | cat-RV |
| Fragment (Z) | tet-FW | tet-FW | tet-FW | tet-FW | tet-FW | tet-FW |
| | tet-RV | tet-RV | tet-RV | tet-RV | tet-RV | tet-RV |

Example 3

Evaluation of Mutant Strains

In Example 3, the *Bacillus subtilis* mutant strains according to the present invention prepared in Examples 1 and 2 were evaluated in terms of secretory productivity. In this Example, alkaline cellulase, alkaline protease, and alkaline amylase were used as target proteins to be introduced into the *Bacillus subtilis* mutant strains.

<Evaluation of Secretion and Production of Alkaline Cellulase>

Evaluation of secretory productivity of alkaline cellulase was performed as described below. Specifically, a recombinant plasmid pHY-S237, in which an alkaline cellulase gene (JP Patent Publication (Kokai) No. 2000-210081 A) fragment (3.1 kb) derived from *Bacillus* sp.) KSM-S237 strain (FERM BP-7875) had been inserted into the BamH I restriction enzyme cleavage point of a shuttle vector pHY300PLK, was introduced into each bacterial strain by the protoplast transformation method. Each of the thus obtained recombinant bacterial strains was shake-cultured overnight at 37° C. in 10 mL of LB medium. Furthermore, 0.05 mL of the culture solution was inoculated in 50 mL of 2×L-maltose medium (2% trypton, 1% yeast extract, 1% NaCl, 7.5% maltose, 7.5 ppm manganese sulfate 4-5 hydrate, and 15 ppm tetracycline), followed by 3 days of shake culture at 30° C. Bacterial bodies were removed by centrifugation from the supernatants of the culture solutions. Alkaline cellulase activity in each of such supernatants was determined, so that the amount of alkaline cellulase that had been secreted and produced outside the bacterial bodies by culture was found.

Cellulase activity was determined as follows. 50 µL of 0.4 mM p-nitrophenyl-β-D-cellotrioside (Seikagaku Corporation) was added to and then mixed with 50 µL of a sample solution that had been adequately diluted with a 1/7.5M phosphate buffer solution (pH7.4 Wako Pure Chemical Industries, Ltd.), followed by reaction at 30° C. The amount of p-nitrophenol that had been liberated by the reaction was quantified based on a change in absorbance (OD420 nm) measured at 420 nm. The amount of enzyme that had caused liberation of 1 µmol p-nitrophenol per minute was determined to be 1 U.

<Evaluation of Secretion and Production of Alkaline Protease>

The secretory productivity of alkaline protease was evaluated as described below. Specifically, PCR was performed using genomic DNA extracted from the *Bacillus clausii* KSM-K16 strain (FERM BP-3376) as a template and a primer set of S237pKAPpp-F and KAPter-R (BglII). Thus, a 1.3-kb DNA fragment encoding alkaline protease (Appl. Microbiol. Biotechnol., 43, 473, (1995)) having an amino acid sequence was amplified. Furthermore, PCR was performed using genomic DNA extracted from the (*Bacillus* sp.) KSM-S237 strain (FERM BP-7875) as a template and a primer set of S237ppp-F2 (BamH I) and S237pKAPpp-R. A 0.6-kb DNA fragment containing a promoter region of the alkaline cellulase gene (JP Patent Publication (Kokai) No. 2000-210081 A) was amplified. Subsequently, SOE-PCR was performed using a mixture of the 2 thus obtained fragments as a template and a primer set of S237 ppp-F2 (BamH I) and KAPter-R (Bgl II). Thus, a 1.8-kb DNA fragment was obtained, in which the alkaline protease gene was ligated downstream of the promoter region of the alkaline cellulase gene. The thus obtained 1.8-kb DNA fragment was inserted to the BamH I-Bgl II restriction enzyme cleavage point of a shuttle vector pHY300PLK (Yakult Honsha Co., Ltd.), so that a plasmid pHYKAP (S237p) for evaluation of the productivity of alkaline protease was constructed.

The thus constructed plasmid pHYKAP (S237p) was introduced into each bacterial strain by the protoplast transformation method. The thus obtained recombinant bacterial strains were shake-cultured for 3 days under the same conditions as those employed for <Evaluation of the secretion and production of alkaline cellulase> above. After culture, bacterial bodies were removed by centrifugation from the supernatants of the culture solutions. Alkaline protease activity in the supernatants was determined. The amounts of alkaline protease that had been secreted and produced outside the bacterial bodies by culture were found. Protease activity in the culture supernatants was determined as follows. Specifically, 100 µL of a 75 mM boric acid —KCl buffer solution (pH 10.5) containing 7.5 mM Succinyl-L-Alanyl-L-Alanyl-L-Alanine p-Nitroanilide (STANA PEPTIDE INSTITUTE, INC.) as a substrate was added to and mixed with 50 µl of a culture supernatant that had been adequately diluted with a 2 mM $CaCl_2$ solution, followed by reaction at 30° C. The amount of p-nitroaniline that had been liberated by the reaction was quantified based on a change in absorbance (OD420 nm) measured at 420 nm. The amount of enzyme that had caused liberation of 1 µmol p-nitroaniline per minute was determined to be 1 U.

<Evaluation of the Secretion and Production of Alkaline Amylase>

The secretory productivity of alkaline amylase was evaluated as follows. Specifically, PCR was performed using genomic DNA extracted from the *Bacillus* sp. KSM-K38 strain (FERM BP-6946) as a template and a primer set of K38matu-F2 (ALAA) and SP64K38-R (Xba I), so that a 1.5-kb DNA fragment encoding alkaline amylase (Appl. Environ. Microbiol., 67, 1744, (2001)) was amplified. Furthermore, PCR was performed using genomic DNA extracted from the *Bacillus* sp. KSM-S237 strain (FERM BP-7875) as a template and a primer set of S237 ppp-F2 (BamH I) and S237ppp-R2 (ALAA), so that a 0.6-kb DNA fragment containing a promoter region and a region encoding a secretion signal sequence of an alkaline cellulase gene (JP Patent Publication (Kokai) No. 2000-210081 A) was amplified. Subsequently, SOE-PCR was performed using as a template a mixture obtained by mixing the thus obtained two fragments and a primer set of S237 ppp-F2 (BamH I) and SP64K38-R (Xba I). Thus, a 2.1-kb DNA fragment was obtained, in which the alkaline amylase gene was ligated downstream of the promoter region and the region encoding the secretion signal sequence of the alkaline cellulase gene. The thus obtained 2.1-kb DNA fragment was inserted into the BamH I-Xba I restriction enzyme cleavage point of a shuttle vector pHY300PLK (Yakult Honsha Co., Ltd.), so that a plasmid pHYK38 (S237ps) for evaluation of the productivity of alkaline amylase was constructed.

The thus constructed plasmid pHYK38 (S237ps) was introduced into each bacterial strain by the protoplast transformation method. The thus obtained recombinant bacterial strains were shake-cultured for 5 days under the same conditions as those employed for <Evaluation of the secretion and production of alkaline cellulase> above. After culture, bacterial bodies were removed by centrifugation from the supernatants of the culture solutions. Alkaline amylase activity in the supernatants was determined, so that the amounts of amylase that had been secreted and produced outside the bacterial bodies by culture were found. Liquitech Amy EPS (Roche Diagnostics) was used for determination of amylase activity in the culture supernatants. Specifically, 100 μL of an R1·R2 mixture (R1 (coupling enzyme):R2 (amylase substrate)=5:1 (Vol.)) was added to and mixed with 50 μL of a sample solution that had been adequately diluted with a 1% NaCl-1/7.5 M phosphate buffer solution (pH 7.4; Wako Pure Chemical Industries, Ltd.), followed by reaction at 30° C. The amount of p-nitrophenol that had been liberated by the reaction was quantified based on a change in absorbance (OD405 nm) measured at 405 nm. The amount of enzyme that had caused liberation of 1 μmol p-nitrophenol per minute was determined to be 1 U.

<Results>

The ability to perform secretion and production of alkaline cellulase, alkaline protease, and alkaline amylase are summarized in Table 9. In addition, in Table 9, the ability to perform secretion and production of each enzyme is expressed by a relative value relative to the amount of the relevant enzyme (produced by the *Bacillus subtilis* 168 strain into which each gene had been similarly introduced) designated with the value 100.

TABLE 9

| *Bacillus subtilis* mutant strain | Productivity Cellulase Wild strain100 | Productivity protease Wild strain100 | Productivity Amylase Wild strain100 |
|---|---|---|---|
| MGB533 strain | 87 | 101 | 86 |
| MGB559 strain | 95 | 96 | 58 |
| MGB592 strain | 90 | 102 | 69 |
| MGB604 strain | 89 | 109 | 78 |
| MGB625 strain | 91 | 111 | 52 |
| MGB653 strain | 134 | 200 | 104 |
| MGB683 strain | 116 | 237 | 10 |
| MGB781 strain | 149 | 280 | 25 |
| MGB723 strain | 141 | 164 | 17 |
| MGB773 strain | 164 | 222 | 10 |
| MGB822 strain | 147 | 208 | 9 |
| MGB834 strain | 158 | 258 | 6 |
| MGB846 strain | 153 | 236 | 15 |
| MGB872 strain | 145 | 195 | 11 |
| MGB885 strain | 147 | 279 | 7 |
| MGB913 strain | 144 | 280 | 6 |
| MGB943 strain | 39 | 264 | |
| MGB860 strain | 166 | 252 | 6 |
| MGB874 strain | 167 | 250 | 4 |
| MGB887 strain | 171 | 270 | 3 |
| NED0100 strain | 86 | | 84 |
| NED0202 strain | 95 | | 96 |
| NED02021 strain | 104 | | |
| NED0301 strain | 91 | | 211 |
| NED0302 strain | 83 | | 116 |
| NED0400 strain | 127 | | 153 |
| NED0501 strain | 96 | | 95 |
| NED0600 strain | 132 | | 102 |
| NED0700 strain | 96 | | 59 |
| NED0802 strain | 94 | | 135 |
| NED0803 strain | 146 | | 96 |
| NED0804 strain | 136 | | 177 |
| NED0900 strain | 100 | | 103 |
| NED1002 strain | 91 | | 119 |
| NED1003 strain | 92 | | 108 |
| NED1100 strain | 144 | | 102 |
| NED1200 strain | 114 | | 66 |
| NED1300 strain | 2 | | 0 |
| NED1400 strain | 104 | | 98 |
| NED1500 strain | 132 | | 16 |
| NED1602 strain | 100 | | 101 |
| NED1802 strain | 2 | | 0 |
| NED1901 strain | 133 | | 35 |
| NED1902 strain | 117 | | 87 |
| NED2201 strain | 139 | | 93 |
| NED2202 strain | 102 | | 41 |
| NED2300 strain | 3 | | |
| NED2402 strain | 111 | | 87 |
| NED2500 strain | 107 | | 97 |
| NED2602 strain | 112 | | 108 |
| NED2702 strain | 131 | | 120 |
| NED2802 strain | 144 | | 77 |
| NED2900 strain | 90 | | 95 |
| NED3000 strain | 133 | | 92 |
| NED3200 strain | 124 | | 94 |
| NED3301 strain | 7 | | 1 |
| NED3303 strain | 102 | | 95 |
| NED3402 strain | 99 | | 128 |
| NED3701 strain | 107 | | 101 |
| NED3800 strain | 114 | | 105 |
| NED4000 strain | 107 | | 99 |
| NED4001 strain | 120 | | |
| NED4002 strain | 125 | | |
| NED4100 strain | 107 | | 87 |

TABLE 10

| Primer name | Nucleotide sequence | SEQ ID NO: |
|---|---|---|
| upp-AFW | AGTCAACTTCAGCGGTGTTC | SEQ ID NO: 121 |
| upp-ARV | GTGCGCGGAACCCCTATTTGTCCCATCAACAATTACACACTTC | SEQ ID NO: 122 |
| upp-BFW | CGTTACTAAAGGGAATGTATGAAATCCCCAAAAGGGGG | SEQ ID NO: 123 |
| upp-BRV | GCGGACGAAATCAACAATCC | SEQ ID NO: 124 |
| Erm-FW | ACAAATAGGGGTTCCGCGCAC | SEQ ID NO: 125 |
| Erm-RV | ACATTCCCTTTAGTAACG | SEQ ID NO: 126 |
| cat-FW | CGCATTAAAGCTTATCGGCAATAGTTACCC | SEQ ID NO: 127 |
| cat-RV | GCCCAAGCGGGTTTTAGGATCATCGATCCCGGAAATCGATTATAGGTATGTGGTTTTGTATTGG | SEQ ID NO: 128 |
| upp-FW | GCCATTCCAATACAAAACCACATACCTATAATCGATGATCCTAAAACCCGCTTGGGCTTATGCCC | SEQ ID NO: 129 |
| upp-RV | ATCGATTTCCGGTACCGGAACTCGAGCCTTGAGCTCAAAAAATCATTCATCCGCAAGCCTTGC | SEQ ID NO: 130 |
| Pro1-AFW | CTGCAAACGCAATGGAAGCTCTATGCG | SEQ ID NO: 131 |
| Pro1-ARV | GGGTAACTATTGCCGATAAGCTTTAATGCGATAAAAACACCCCTTTAGATAATCTTATCC | SEQ ID NO: 132 |
| Pro1-BFW | AAGGCTCGAGTTCCGGTACCGGAAATCGATAAATTTCCGTCTTGTATGTGCGACAAACGG | SEQ ID NO: 133 |

TABLE 10-continued

| Primer name | Nucleotide sequence | SEQ ID NO: |
|---|---|---|
| Pro1-BRV | TGAAAACTTGCTGTACAGCCCC | SEQ ID NO: 134 |
| Pro1-ERV | CCGTTTGTCGCACATACAAGACGGAAATTTATAAAAACACCCCTTTAGATAATCTTATCC | SEQ ID NO: 135 |
| Pro1-FFW | GGATAAGATTATCTAAAGGGGTGTTTTTATAAATTTCCGTCTTGTATGTGCGACAAACGG | SEQ ID NO: 136 |
| Pro3-AFW | CCAGATTTAGATGGAAAGCC | SEQ ID NO: 137 |
| Pro3-ARV | GGGTAACTATTGCCGATAAGCTTTAATGCGATAAAAAGGGGCAGAACTGATTCAGC | SEQ ID NO: 138 |
| Pro3-BFW | AAGGCTCGAGTTCCGGTACCGGAAATCGATATTTGTAGACTTTAATAAGAAACGAAAGGC | SEQ ID NO: 139 |
| Pro3-BRV | TCACGATGCCTATGATCTAAAGGTTTGGGG | SEQ ID NO: 140 |
| Pro3-ERV | GCCTTTCGTTTCTTATTAAAGTCTACAAATCCCCAATCAAATAGATGGAAAATTAGGCTC | SEQ ID NO: 141 |
| Pro3-FFW | GAGCCTAATTTTCCATCTATTTGATTGGGGATTTGTAGACTTTAATAAGAAACGAAAGGC | SEQ ID NO: 142 |
| Pro4-AFW | GCCAGTCCAAGACCGTCACTTCAGCCATGC | SEQ ID NO: 143 |
| Pro4-ARV | GGGTAACTATTGCCGATAAGCTTTAATGCGATAAAAAATGCCTTCCGCTACTTAATAAGCTGTTGGG | SEQ ID NO: 144 |
| Pro4-BFW | AAGGCTCGAGTTCCGGTACCGGAAATCGATTGTGTGGCTCTTTTTGCATC | SEQ ID NO: 145 |
| Pro4-BRV | CGGTATGGGTGAAACGAACGTCTGTGTGGAGC | SEQ ID NO: 146 |
| Pro4-ERV | GATGCAAAAAGAGCCACACACTACTTAATAAGCTGTTGGG | SEQ ID NO: 147 |
| Pro4-FFW | CCCAACAGCTTATTAAGTAGTGTGTGGCTCTTTTTGCATC | SEQ ID NO: 148 |
| Pro7-AFW | TCCGCACTACACATTGCCGTGATAAATGGG | SEQ ID NO: 149 |
| Pro7-ARV | GGGTAACTATTGCCGATAAGCTTTAATGCGATAAAAACATTATTACCTTCCTCTGATAATGAAATA | SEQ ID NO: 150 |
| Pro7-BFW | AAGGCTCGAGTTCCGGTACCGGAAATCGATCGGAACAATTGGAAACAGAATGGGTTGAATTC | SEQ ID NO: 151 |
| Pro7-BRV | GCCTCATGAGCTGCCAATGTTTGATGATCC | SEQ ID NO: 152 |
| Pro7-ERV | GAATTCAACCCATTCTGTTTCCAATTGTTCCG CATTATTACCTTCCTCTGATAATGAAATAT | SEQ ID NO: 153 |
| Pro7-FFW | ATATTTCATTATCAGAGGAAGGTAATAATG CGGAACAATTGGAAACAGAATGGGTTGAATTC | SEQ ID NO: 154 |
| PBSX-AFW | TGCGGAGGCCCAAGGACGCC | SEQ ID NO: 155 |
| PBSX-ARV | GGGTAACTATTGCCGATAAGCTTTAATGCGATAAAAAATCAGCAGCACTTGCAGGTCGCT | SEQ ID NO: 156 |
| PBSX-BFW | AAGGCTCGAGTTCCGGTACCGGAAATCGATGCGACGAAAGAGAAGATCGCAG | SEQ ID NO: 157 |
| PBSX-BRV | GTCTGACAGCATTGTCACGG | SEQ ID NO: 158 |
| PBSX-ERV | GCGATCTTCTCTTTCGTCGCCAGCAGCACTTGCAGGTCGC | SEQ ID NO: 159 |
| PBSX-FFW | GCGACCTGCAAGTGCTGCTGGCGACGAAAGAGAAGATCGC | SEQ ID NO: 160 |
| spB-AFW | TTTTTCCCTAGTTACGTCCG | SEQ ID NO: 161 |
| spB-ARV | GGGTAACTATTGCCGATAAGCTTTAATGCGATAAAAATGTACTGATATTAATGACATGC | SEQ ID NO: 162 |
| spB-BFW | AAGGCTCGAGTTCCGGTACCGGAAATCGATGCTGTATCTCCTGTGAACACAATGGGTGCC | SEQ ID NO: 163 |
| spB-BRV | TCTTTCGTAATGAGCGGGGC | SEQ ID NO: 164 |
| spB-ERV | GTGTTCACAGGAGATACAGCTACTGATATTAATGACATGC | SEQ ID NO: 165 |
| spB-FFW | GCATGTCATTAATATCAGTAGCTGTATCTCCTGTGAACAC | SEQ ID NO: 166 |
| pks-AFW | CTGCAAGCGCGATGGCCGCG | SEQ ID NO: 167 |
| pks-ARV | GGGTAACTATTGCCGATAAGCTTTAATGCGATAAAAAATGTCCTTAATTCGGTCCGTTACCTTTTCT | SEQ ID NO: 168 |
| pks-BFW | AAGGCTCGAGTTCCGGTACCGGAAATCGATAAATCAAGGAGCATCAATATGTGGTGGCTT | SEQ ID NO: 169 |
| pks-BRV | CGATAGGAGCAGCCATGCT | SEQ ID NO: 170 |
| pks-ERV | CCACCACATATTGATGCTCCCCTAATTCGGTCCGTTACC | SEQ ID NO: 171 |
| pks-FFW | GGTAACGGACCGAATTAAGGGGAGCATCAATATGTGGTGG | SEQ ID NO: 172 |
| Pro2-AFW | AGTTCTCAACCATCGGCCCG | SEQ ID NO: 173 |
| Pro2-ARV | GGGTAACTATTGCCGATAAGCTTTAATGCGATAAAAATAAGTGGGCAGTTTGTGGGC | SEQ ID NO: 174 |
| Pro2-BFW | AAGGCTCGAGTTCCGGTACCGGAAATCGATACCATGGAATAGATAGGATG | SEQ ID NO: 175 |
| Pro2-BRV | AACTTTCACGGCGTCTGGGG | SEQ ID NO: 176 |
| Pro2-ERV | CATCCTATCTATTCATGGTTAAGTGGGCAGTTTGTGGGC | SEQ ID NO: 177 |
| Pro2-FFW | GCCCACAAACTGCCCACTTAACCATGGAATAGATAGGATG | SEQ ID NO: 178 |
| Pro5-AFW | TAGCGTATTGCTTGCTGCAGGATTAGACGG | SEQ ID NO: 179 |
| Pro5-ARV | GGGTAACTATTGCCGATAAGCTTTAATGCGATAAAAAAGATTTCAACGTAATTATGGATTCATTTG | SEQ ID NO: 180 |
| Pro5-BFW | AAGGCTCGAGTTCCGGTACCGGAAATCGATTCTCCATGCTGTGTGATTGATCAATGGAGG | SEQ ID NO: 181 |
| Pro5-BRV | CTATTTATTCCCTGGCGACATACCGGGGGC | SEQ ID NO: 182 |
| Pro5-ERV | CCTCCATTGATCAATCACACAGCATGGAGAAGATTTCAACGTAATTATGGATTCATTTGG | SEQ ID NO: 183 |
| Pro5-FFW | CCAAATGAATCCATAATTACGTTGAAATCTTCTCCATGCTGTGTGATTGATCAATGGAGG | SEQ ID NO: 184 |
| Pro6-AFW | AATTCATGACATCCCCCCGC | SEQ ID NO: 185 |
| Pro6-ARV | GGGTAACTATTGCCGATAAGCTTTAATGCGATAAAAAAATCCCGCAGCATATCAGCAGTGCGCCGAG | SEQ ID NO: 186 |
| Pro6-BFW | AAGGCTCGAGTTCCGGTACCGGAAATCGATCACACACGAATGTGGCGTGTGGTGCATCGC | SEQ ID NO: 187 |
| Pro6-BRV | CATCGCTTCCGTTCTATCGG | SEQ ID NO: 188 |
| Pro6-ERV | GGAGGGCGAAGGAATGCAAGTGAAGCCCAAATGACAGGGG | SEQ ID NO: 189 |
| Pro6-FFW | CCCCTGTCATTTGGGCTTCACTTGCATTCCTTCGCCCTCC | SEQ ID NO: 190 |
| skin-AFW | ACCACTTCGGCTCATTACCC | SEQ ID NO: 191 |
| skin-ARV | GGGTAACTATTGCCGATAAGCTTTAATGCGATAAAAAGTCACCTCCACAAAAGTATG | SEQ ID NO: 192 |
| skin-BFW | AAGGCTCGAGTTCCGGTACCGGAAATCGATCAGAAGAAGCCGGATCTC | SEQ ID NO: 193 |

The invention claimed is:

1. A *Bacillus subtilis* mutant strain, comprising a genomic structure of a *Bacillus subtilis* 168 wild-type strain from which an entire deletion region or group of deletion regions selected from the group consisting of:

| | Deletion region(s) |
|---|---|
| (a) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, and ydcL-ydeK-ydhU region |
| (b) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) pps (ppsE-ppsA) region, prophage2 (ydcL-ydeJ) region, ydcL-ydeK-ydhU region, and yisB-yitD region |
| (c) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, and yunA-yurT region |
| (d) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, and cgeE-ypmQ region |
| (e) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, and yeeK-yesX region |
| (f) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, and ydiM-gutR-yebA region |
| (g) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, ydiM-gutR-yebA region, and ykuS-ykqB region |
| (h) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, ydiM-gutR-yebA region, ykuS-ykqB region, and pdp-rocR region |
| (i) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, and pdp-rocR region |
| (j) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ yeeK-yesX region, pdp-rocR region, and ycxB-sipU region |

| | Deletion region(s) |
|---|---|
| (k) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, and SKIN-Pro7 (spoIVCB-yraK) region |
| (l) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, and sbo-ywhH region |
| (m) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, and cspB-yhcT region |
| (n) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2(ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, cspB-yhcT region, and yybP-yyaJ region |
| (o) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, cspB-yhcT region, yybP-yyaJ region, and ytxK-braB region |
| (p) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, ydiM-gutR-yebA region, pdp-rocR region, ycxB-sipU region, SKIN-Pro7 (spoIVCB-yraK) region, sbo-ywhH region, cspB-yhcT region, yybP-yyaJ region, and ytxK-braB region |
| (q) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, ydiM-gutR-yebA region, ykuS-ykqB region, pdp-rocR region, ycxB-sipU region, SKIN-Pro7 (spoIVCB-yraK) region, sbo-ywhH region, cspB-yhcT region, yybP-yyaJ region, and ytxK-braB region |
| (r) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, and yybP-yyaJ region |
| (s) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, yybP-yyaJ region, and yncM-fosB region |
| (t) | prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, yybP-yyaJ region, ytxK-braB region, and yncM-fosB region |
| (u) | ycxB-sipU region |
| (v) | ydiM-gutR-yebA region |
| (w) | cspB-yhcT region |
| (x) | ykuS-ykqB region |
| (y) | ytxK-braB region |
| (z) | sbo-ywhH region, and |
| (aa) | pdp-rocR region | has been deleted, wherein the region to be deleted compared to the wild-type *Bacillus subtilis* 168 strain is located between an oligonucleotide set as set forth below:

| | Oligonucleotide set | | | |
|---|---|---|---|---|
| Region | 1st oligo-nucleotide | SEQ ID NO: | 2nd oligo-nucleotide | SEQ ID NO: |
| prophage1 (ybbU-ybdE) region | taagattatc taaaggggtg | SEQ ID NO: 1 | CATACAAGAC GGAAATTT | SEQ ID NO: 2 |
| ycxB-sipU region | atataaaagg atcagcactg | SEQ ID NO: 7 | CCATGTTCTT TTTGCATTGC | SEQ ID NO: 8 |
| prophage2 (ydcL-ydeJ) region | gcccacaaac tgcccactta | SEQ ID NO: 11 | TCCTATCTAT TCCATGGT | SEQ ID NO: 12 |
| ydcL-ydeK-ydhU region | gcccacaaac tgcccactta | SEQ ID NO: 13 | GGGCAATCCG TGGAACGGGT | SEQ ID NO: 14 |
| prophage3 (ydiM-ydjC) region | agcgatgtga ggtgaaaatt | SEQ ID NO: 15 | TTATTAAAGT CTACAAAT | SEQ ID NO: 16 |
| ydiM-gutR-yebA region | agcgatgtga ggtgaaaatt | SEQ ID NO: 17 | TCCATAGCGC CGAAGAATCT | SEQ ID NO: 18 |
| yeeK-yesX region | atgtgaagga gagagtaaat | SEQ ID NO: 19 | CGTCTTATCC CTTAGTCCTC | SEQ ID NO: 20 |
| cspB-yhcT region | gcagttttc atatcaattt | SEQ ID NO: 21 | TCGAAAGGA GCCATTTAAC | SEQ ID NO: 22 |
| yisB-yitD region | gatgtaaggg aggagcggat | SEQ ID NO: 27 | CGACGAGAGC CCCGCAGCCG | SEQ ID NO: 28 |
| prophage4 (yjcM-yjdJ) region | ttattaagta gcggaaggca | SEQ ID NO: 33 | TGCAAAAGA GCCACACA | SEQ ID NO: 34 |
| PBSX (ykdA-xlyA) region | gacctgcaag tgctgctgat | SEQ ID NO: 37 | GATCTTCTCT TTCGTCGC | SEQ ID NO: 38 |

| Region | 1st oligo-nucleotide | SEQ ID NO: | 2nd oligo-nucleotide | SEQ ID NO: |
|---|---|---|---|---|
| ykuS-ykqB region | gcactctagt aaacggaggt | SEQ ID NO: 41 | GACGGCTTAT TTGGCTGCTA | SEQ ID NO: 42 |
| pks (pksA-ymaC) region | atcagaggaa ggtaataatg | SEQ ID NO: 49 | CATTCTGTTT CCAATTGT | SEQ ID NO: 50 |
| prophage5 (ynxB-dut) region | ccataattac gttgaaatct | SEQ ID NO: 53 | AATCACACAG CATGGAGA | SEQ ID NO: 54 |
| yncM-fosB region | gcggcttttt gctgcttcgt | SEQ ID NO: 55 | CCTTATATGA AATATGGTTG | SEQ ID NO: 56 |
| pps (ppsE-ppsA) region | cctcttatta tgagaactgg | SEQ ID NO: 57 | CTCTGTCCGC TAATCCGC | SEQ ID NO: 58 |
| prophage6 (yoaV-yobO) region | tgctgatatg ctgcgggatt | SEQ ID NO: 59 | ACGCCACATT CGTGTGTG | SEQ ID NO: 60 |
| spb (yodU-ypqP) region | atgtcattaa tatcagtaca | SEQ ID NO: 65 | GTTCACAGGA GATACAGC | SEQ ID NO: 66 |
| cgeE-ypmQ region | ggtttgtgca aacgcctatt | SEQ ID NO: 67 | GGCTGGAAAG GATGGATGTC | SEQ ID NO: 68 |
| skin (spoIVCB-spoIIIC) region | catactttg tggaggtgac | SEQ ID NO: 77 | GAGATCCGGC TTCTTCTG | SEQ ID NO: 78 |
| SKIN-Pro7 (spoIVCB-yraK) region | catactttg tggaggtgac | SEQ ID NO: 81 | CATTCTGTTT CCAATTGT | SEQ ID NO: 82 |
| ytxK-braB region | ctaagctgct tttaaaacac | SEQ ID NO: 87 | AACGCAGGCG TTCTGTGACA | SEQ ID NO: 88 |
| yunA-yurT region | aaatttctcg acaagggaa | SEQ ID NO: 95 | TCGAAGGAGG GAAAACAGT | SEQ ID NO: 96 |
| sbo-ywhH region | gggaggattc | SEQ ID | GACGATGTCT | SEQ ID |
| region | aattatgaaa | NO: 103 | GGATGTTTTT | NO: 104 |
| pdp-rocR region | ggcgccttcg cttccgcggc | SEQ ID NO: 111 | GATCAGGCTT CCTGCTCCGG | SEQ ID NO: 112 |
| yybP-yyaJ region | ccgcgtcggg atgctttttc | SEQ ID NO: 113 | GCAGATCCGC ACTGACTTTT | SEQ ID NO: 114. |

2. The *Bacillus subtilis* mutant strain according to claim 1, further comprising a gene encoding a target protein.

3. The *Bacillus subtilis* mutant strain according to claim 2, wherein the secretory productivity of the target protein is significantly increased compared with the secretory productivity when the same gene is introduced into the wild-type *Bacillus subtilis* 168 strain.

4. The *Bacillus subtilis* mutant strain according to claim 3, wherein the gene encoding the target protein contains a nucleotide sequence encoding a region corresponding to a secretion signal or the gene is appropriately ligated to DNA upstream thereof containing a nucleotide sequence that encodes a region corresponding to a secretion signal.

5. The *Bacillus subtilis* mutant strain according to claim 4, wherein the target protein is at least one enzyme selected from the group consisting of cellulase, protease, and amylase.

6. The *Bacillus subtilis* mutant strain according to claim 1, wherein said group of deletion regions is (s) prophage6 (yoaV-yobO) region, prophage1 (ybbU-ybdE) region, prophage4 (yjcM-yjdJ) region, PBSX (ykdA-xlyA) region, prophage5 (ynxB-dut) region, prophage3 (ydiM-ydjC) region, spb (yodU-ypqP) region, pks (pksA-ymaC) region, skin (spoIVCB-spoIIIC) region, pps (ppsE-ppsA) region, prophage2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, SKIN-Pro7 (spoIVCB-yraK) region, sbo-ywhH region, yybP-yyaJ region, and yncM-fosB region.

* * * * *

SEQUENCE LISTING

<160> NUMBER OF SEQ ID NOS: 463

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
    Oligonucleotide defining one terminal of prophage1 (ybbU-ybdE)

region

<400> SEQUENCE: 1
taagattatc taaagggtg                                                    20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of prophage1
      (ybbU-ybdE) region

<400> SEQUENCE: 2
catacaagac ggaaattt                                                     18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of ybbU-ybdG-yceK region

<400> SEQUENCE: 3
taagattatc taaagggtg                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ybbU-ybdG-yceK
      region

<400> SEQUENCE: 4
cacccattat gtattatagt                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of ycxB-ydbP region

<400> SEQUENCE: 5
atataaaagg atcagcactg                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ycxB-ydbP region

<400> SEQUENCE: 6
ttgaaaagga gatgtgacat                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:

Oligonucleotide defining one terminal of ycxB-sipU region

<400> SEQUENCE: 7
atataaaagg atcagcactg                                         20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ycxB-sipU region

<400> SEQUENCE: 8
ccatgttctt tttgcattgc                                         20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of ydcD-ydcK region

<400> SEQUENCE: 9
ggtggaggtg tatgtttttt                                         20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide defining the other terminal of ydcD-ydcK region

<400> SEQUENCE: 10
ccatattcgt caacctttt                                          19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of prophage2 (ydcL-ydeJ)
      region

<400> SEQUENCE: 11
gcccacaaac tgcccactta                                         20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of prophage2
      (ydcL-ydeJ) region

<400> SEQUENCE: 12
tcctatctat tccatggt                                           18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:

-continued

Oligonucleotide defining one terminal of ydcL-ydeK-ydhU region

<400> SEQUENCE: 13
gcccacaaac tgcccactta                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ydcL-ydeK-ydhU
      region

<400> SEQUENCE: 14
gggcaatccg tggaacgggt                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of prophage3 (ydiM-ydjC)
      region

<400> SEQUENCE: 15
agcgatgtga ggtgaaaatt                                              20

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of prophage3
      (ydiM-ydjC) region

<400> SEQUENCE: 16
ttattaaagt ctacaaat                                                18

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of ydiM-gutR-yebA region

<400> SEQUENCE: 17
agcgatgtga ggtgaaaatt                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ydiM-gutR-yebA
      region

<400> SEQUENCE: 18
tccatagcgc cgaagaatct                                              20

<210> SEQ ID NO 19
<211> LENGTH: 20
<212> TYPE: DNA
<213> ORGANISM: Artificial Sequence

```
<220> FEATURE:
<223> OTHER INFORMATION: Description of Artificial Sequence:
      Oligonucleotide defining one terminal of yeeK-yesX region

<400> SEQUENCE: 19
atgtgaagga gagagtaaat                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yeeK-yesX region

<400> SEQUENCE: 20
cgtcttatcc cttagtcctc                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of cspB-yhcT region

<400> SEQUENCE: 21 gcagttttc atatcaattt                                                     20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of cspB-yhcT region

<400> SEQUENCE: 22
tcgaaaagga gccatttaac                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yhdP-yhaL region

<400> SEQUENCE: 23
tatacaaggt gcttttctta                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yhdP-yhaL region

<400> SEQUENCE: 24
cattgagccg cacagctttt                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:
```

Oligonucleotide defining one terminal of yhxD-yhjP region

<400> SEQUENCE: 25
cagctccttt cataaagcta                                          20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yhxD-yhjP region

<400> SEQUENCE: 26
caaaaaagaa ccctcttttt                                          20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yisB-yitD region

<400> SEQUENCE: 27
gatgtaaggg aggagcggat                                          20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yisB-yitD region

<400> SEQUENCE: 28
cgacgagagc cccgcagccg                                          20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yitH-yitZ region

<400> SEQUENCE: 29
ctgttcggga aaaagagggg                                          20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yitH-yitZ region

<400> SEQUENCE: 30
gcggtgccgc atttcagccg                                          20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of oppA-yjbK region

```
<400> SEQUENCE: 31
tgaaaattat tattaggggg                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of oppA-yjbK region

<400> SEQUENCE: 32
gggcggaaag gaagagcatc                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of prophage4 (yjcM-yjdJ)
      region

<400> SEQUENCE: 33
ttattaagta gcggaaggca                                              20

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of prophage4
      (yjcM-yjdJ) region

<400> SEQUENCE: 34
tgcaaaaaga gccacaca                                                18

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yjcM-ctaO-yjgB region

<400> SEQUENCE: 35
aacgatttag tatcaattta                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yjcM-ctaO-yjgB
      region

<400> SEQUENCE: 36
ggtagatcaa ttaggaggga                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of PBSX (ykdA-xlyA) region
```

<400> SEQUENCE: 37
gacctgcaag tgctgctgat                                                        20

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of PBSX (ykdA-xlyA)
      region

<400> SEQUENCE: 38
gatcttctct ttcgtcgc                                                          18

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yjqB-htrA region

<400> SEQUENCE: 39
ggtaaagggg ggcgttcaag                                                        20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yjqB-htrA region

<400> SEQUENCE: 40
agagaaacgg agtgaacatg                                                        20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of ykuS-ykqB region

<400> SEQUENCE: 41
gcactctagt aaacggaggt                                                        20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ykuS-ykqB region

<400> SEQUENCE: 42
gacggcttat ttggctgcta                                                        20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide defining one terminal of slp-ylaM region

```
<400> SEQUENCE: 43
cccgctttga gcgagggct                                                    19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of slp-ylaM region

<400> SEQUENCE: 44
taagcatatg acataaatta                                                   20

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide defining one terminal of ctaA-ylbE region

<400> SEQUENCE: 45
cgcctaaggc tttggtctt                                                    19

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ctaA-ylbE region

<400> SEQUENCE: 46
cccttcttcg gggcctttta                                                   20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of gid-ylxL region

<400> SEQUENCE: 47
taaactagga gatgtgaaag                                                   20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of gid-ylxL region

<400> SEQUENCE: 48
cacagcttta tccgacaatc                                                   20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of pks (pksA-ymaC) region

<400> SEQUENCE: 49
```

-continued atcagaggaa ggtaataatg                                              20

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of pks (pksA-ymaC)
      region

<400> SEQUENCE: 50
cattctgttt ccaattgt                                                18

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of spoVS-ymzA region

<400> SEQUENCE: 51
aaaactaagg gggagcagaa                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of spoVS-ymzA region

<400> SEQUENCE: 52
cataacatga aaaaaaactg                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of prophage5 (ynxB-dut)
      region

<400> SEQUENCE: 53
ccataattac gttgaaatct                                              20

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of prophage5
      (ynxB-dut) region

<400> SEQUENCE: 54
aatcacacag catggaga                                                18

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yncM-fosB region

<400> SEQUENCE: 55

```
gcggcttttt gctgcttcgt                                               20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yncM-fosB region

<400> SEQUENCE: 56
ccttatatga aatatggttg                                               20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of pps (ppsE-ppsA) region

<400> SEQUENCE: 57
cctcttatta tgagaactgg                                               20

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of pps (ppsE-ppsA)
      region

<400> SEQUENCE: 58
ctctgtccgc taatccgc                                                 18

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of prophage6 (yoaV-yobO)
      region

<400> SEQUENCE: 59
tgctgatatg ctgcgggatt                                               20

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of prophage6
      (yoaV-yobO) region

<400> SEQUENCE: 60
acgccacatt cgtgtgtg                                                 18

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yoxC-yocS region
```

```
<400> SEQUENCE: 61
ataagaaaag gagtgaacat                                               20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yoxC-yocS region

<400> SEQUENCE: 62
gtaccctttt tgatgcatat                                               20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yojO-yozE region

<400> SEQUENCE: 63
cgccaaaaag cataggatta                                               20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yojO-yozE region

<400> SEQUENCE: 64
gacatcagga ggggaaaccc                                               20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of spb (yodU-ypqP) region

<400> SEQUENCE: 65
atgtcattaa tatcagtaca                                               20

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of spb (yodU-ypqP)
      region

<400> SEQUENCE: 66
gttcacagga gatacagc                                                 18

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of cgeE-ypmQ region

<400> SEQUENCE: 67
```

```
ggtttgtgca aacgcctatt                                               20
```

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of cgeE-ypmQ region

<400> SEQUENCE: 68

```
ggctggaaag gatggatgtc                                               20
```

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of ypzC-drm region

<400> SEQUENCE: 69

```
agcatgaggt tacgggcagt                                               20
```

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ypzC-drm region

<400> SEQUENCE: 70

```
ggaggctttc aagatgcctg                                               20
```

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yqxK-yqjP region

<400> SEQUENCE: 71

```
gaactgagtt aatctttagc                                               20
```

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yqxK-yqjP region

<400> SEQUENCE: 72

```
tgaagacaag gagcgaaagg                                               20
```

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of zwf-yqzF region

<400> SEQUENCE: 73

```
cgaataaagt gaggtacttt                                               20
```

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of zwf-yqzF region

<400> SEQUENCE: 74
cgcgggctga cttgattgcg                                              20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yqgZ-yqgN region

<400> SEQUENCE: 75
agcggatctt cggtttttca                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yqgZ-yqgN region

<400> SEQUENCE: 76
ctattccgag ggggatgaga                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of skin (spoIVCB-spoIIIC)
      region

<400> SEQUENCE: 77 catactttg tggaggtgac                                               20

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of skin
      (spoIVCB-spoIIIC) region

<400> SEQUENCE: 78
gagatccggc ttcttctg                                                18

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of prophage7 (yrkM-yraK)
      region

<400> SEQUENCE: 79

```
atcagaggaa ggtaataatg                                              20
```

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of prophage7
      (yrkM-yraK) region

<400> SEQUENCE: 80

```
cattctgttt ccaattgt                                                18
```

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of SKIN-Pro7
      (spoIVCB-yraK) region

<400> SEQUENCE: 81

```
catactttg tggaggtgac                                               20
```

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of SKIN-Pro7
      (spoIVCB-yraK) region

<400> SEQUENCE: 82

```
cattctgttt ccaattgt                                                18
```

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yqeD-yrzL region

<400> SEQUENCE: 83

```
gagtgaccat agacatgtta                                              20
```

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide defining the other terminal of yqeD-yrzL region

<400> SEQUENCE: 84

```
gcgaatttgg gaaagagg                                                18
```

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yrzF-yrxA region

<400> SEQUENCE: 85
gagcaaagaa ggtgaatgaa                                                   20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yrzF-yrxA region

<400> SEQUENCE: 86
gccggcttct tcgagggctt                                                   20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of ytxK-braB region

<400> SEQUENCE: 87
ctaagctgct tttaaaacac                                                   20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ytxK-braB region

<400> SEQUENCE: 88
aacgcaggcg ttctgtgaca                                                   20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of ytzH-ytbQ region

<400> SEQUENCE: 89
ctgaagggat gtgtaccgtt                                                   20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ytzH-ytbQ region

<400> SEQUENCE: 90
cggcaaatta tgaggagctg                                                   20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of ytvB-ytoA region

<400> SEQUENCE: 91
cgggcggaga ttgaggacaa                                                   20

```
<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ytvB-ytoA region

<400> SEQUENCE: 92
ggtaaagtaa gacgaagcag                                               20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of pckA-mntA region

<400> SEQUENCE: 93
acgataaagg aaggtttcat                                               20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of pckA-mntA region

<400> SEQUENCE: 94
tggcaaagag gaggagaaat                                               20

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide defining one terminal of yunA-yurT region

<400> SEQUENCE: 95
aaatttctcg acaagggaa                                                19

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yunA-yurT region

<400> SEQUENCE: 96
tcgaaggagg gaaaaacagt                                               20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yurZ-yuxN region

<400> SEQUENCE: 97
ttttcggaat attccttctc                                               20
```

```
<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yurZ-yuxN region

<400> SEQUENCE: 98
gctgttccgc atctttggcg                                              20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of smpB-yvbK region

<400> SEQUENCE: 99
cgaatcaagc actatgcctt                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of smpB-yvbK region

<400> SEQUENCE: 100
cggcggcttt tttatgcttt                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yvdM-yvcP region

<400> SEQUENCE: 101
aggaattgac tcccttattc                                              20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yvdM-yvcP region

<400> SEQUENCE: 102
gtacatataa ggggatcaa                                               20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of sbo-ywhH region

<400> SEQUENCE: 103
gggaggattc aattatgaaa                                              20

<210> SEQ ID NO 104
<211> LENGTH: 20
```

```
<212> TYPE: DNA
<213> ORGANISM: Artificial Sequence
<220> FEATURE:
<223> OTHER INFORMATION: Description of Artificial Sequence:
      Oligonucleotide defining the other terminal of sbo-ywhH region

<400> SEQUENCE: 104
gacgatgtct ggatgttttt                                                     20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of ywcB-ywaE region

<400> SEQUENCE: 105
cgaataaaag gaggaaagcc                                                     20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of ywcB-ywaE region

<400> SEQUENCE: 106
tactggattc ccgtcaaagc                                                     20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of dltA-rocR region

<400> SEQUENCE: 107
ccgcgaatac cggttcatat                                                     20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of dltA-rocR region

<400> SEQUENCE: 108
gatcaggctt cctgctccgg                                                     20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of dltA-hutM region

<400> SEQUENCE: 109
ccgcgaatac cggttcatat                                                     20

<210> SEQ ID NO 110
<211> LENGTH: 20
<212> TYPE: DNA
<213> ORGANISM: Artificial Sequence
```

```
<220> FEATURE:
<223> OTHER INFORMATION: Description of Artificial Sequence:
      Oligonucleotide defining the other terminal of dltA-hutM region

<400> SEQUENCE: 110
ccatgctgag cggggtgtgc                                              20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of pdp-rocR region

<400> SEQUENCE: 111
ggcgccttcg cttccgcggc                                              20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of pdp-rocR region

<400> SEQUENCE: 112
gatcaggctt cctgctccgg                                              20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining one terminal of yybP-yyaJ region

<400> SEQUENCE: 113
ccgcgtcggg atgcttttc                                               20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide defining the other terminal of yybP-yyaJ region

<400> SEQUENCE: 114
gcagatccgc actgactttt                                              20

<210> SEQ ID NO 115
<211> LENGTH: 3150
<212> TYPE: DNA
<213> ORGANISM: Bacillus sp. KSM-S237
<220> FEATURE:
<221> NAME/KEY: CDS
<222> LOCATION: (573)..(3044)
<220> FEATURE:
<221> NAME/KEY: sig_peptide
<222> LOCATION: (573)..(659)
<220> FEATURE:
<221> NAME/KEY: mat_peptide
<222> LOCATION: (660)..(3044)

<400> SEQUENCE: 115
gatttgccga tgcaacaggc ttatatttag aggaaatttc ttttaaatt gaatacggaa    60 taaaatcagg taaacaggtc ctgattttat tttttgagt ttttagaga actgaagatt    120
```

```
gaaataaaag tagaagacaa aggacataag aaaattgcat tagttttaat tatagaaaac      180 gccttttat aattatttat acctagaacg aaaatactgt ttcgaaagcg gtttactata       240
aaaccttata ttccggctct tttttaaaac aggggtaaa aattcactct agtattctaa      300
tttcaacatg ctataataaa tttgtaagac gcaatatgca tctcttttt tacgatatat      360 gtaagcggtt aaccttgtgc tatatgccga tttaggaagg ggggtagatt gagtcaagta      420
gtaataatat agataactta taagttgttg agaagcagga gagcatctgg gttactcaca      480 agtttttta aaactttaac gaaagcactt tcggtaatgc ttatgaattt agctatttga       540
ttcaattact ttaaaaatat ttaggaggta at atg atg tta aga aag aaa aca       593
                                   Met Met Leu Arg Lys Lys Thr
                                                          -25 aag cag ttg att tct tcc att ctt att tta gtt tta ctt cta tct tta       641
Lys Gln Leu Ile Ser Ser Ile Leu Ile Leu Val Leu Leu Leu Ser Leu
        -20             -15                 -10 ttt ccg gca gct ctt gca gca gaa gga aac act cgt gaa gac aat ttt       689
Phe Pro Ala Ala Leu Ala Ala Glu Gly Asn Thr Arg Glu Asp Asn Phe
 -5              -1   1                 5                      10 aaa cat tta tta ggt aat gac aat gtt aaa cgc cct tct gag gct ggc       737
Lys His Leu Leu Gly Asn Asp Asn Val Lys Arg Pro Ser Glu Ala Gly
                15                  20                  25 gca tta caa tta caa gaa gtc gat gga caa atg aca tta gta gat caa       785
Ala Leu Gln Leu Gln Glu Val Asp Gly Gln Met Thr Leu Val Asp Gln
            30                  35                  40 cat gga gaa aaa att caa tta cgt gga atg agt aca cac gga tta cag       833
His Gly Glu Lys Ile Gln Leu Arg Gly Met Ser Thr His Gly Leu Gln
        45                  50                  55 tgg ttt cct gag atc ttg aat gat aac gca tac aaa gct ctt tct aac       881
Trp Phe Pro Glu Ile Leu Asn Asp Asn Ala Tyr Lys Ala Leu Ser Asn
    60                  65                  70 gat tgg gat tcc aat atg att cgt ctt gct atg tat gta ggt gaa aat       929
Asp Trp Asp Ser Asn Met Ile Arg Leu Ala Met Tyr Val Gly Glu Asn
75                  80                  85                  90 ggg tac gct aca aac cct gag tta atc aaa caa aga gtg att gat gga       977
Gly Tyr Ala Thr Asn Pro Glu Leu Ile Lys Gln Arg Val Ile Asp Gly
                95                  100                 105 att gag tta gcg att gaa aat gac atg tat gtt att gtt gac tgg cat      1025
Ile Glu Leu Ala Ile Glu Asn Asp Met Tyr Val Ile Val Asp Trp His
            110                 115                 120 gtt cat gcg cca ggt gat cct aga gat cct gtt tat gca ggt gct aaa      1073
Val His Ala Pro Gly Asp Pro Arg Asp Pro Val Tyr Ala Gly Ala Lys
        125                 130                 135 gat ttc ttt aga gaa att gca gct tta tac cct aat aat cca cac att      1121
Asp Phe Phe Arg Glu Ile Ala Ala Leu Tyr Pro Asn Asn Pro His Ile
    140                 145                 150 att tat gag tta gcg aat gag ccg agt agt aat aat aat ggt gga gca      1169
Ile Tyr Glu Leu Ala Asn Glu Pro Ser Ser Asn Asn Asn Gly Gly Ala
155                 160                 165                 170 ggg att ccg aat aac gaa gaa ggt tgg aaa gcg gta aaa gaa tat gct      1217
Gly Ile Pro Asn Asn Glu Glu Gly Trp Lys Ala Val Lys Glu Tyr Ala
                175                 180                 185 gat cca att gta gaa atg tta cgt aaa agc ggt aat gca gat gac aac      1265
Asp Pro Ile Val Glu Met Leu Arg Lys Ser Gly Asn Ala Asp Asp Asn
            190                 195                 200 att atc att gtt ggt agt cca aac tgg agt cag cgt ccg gac tta gca      1313
Ile Ile Ile Val Gly Ser Pro Asn Trp Ser Gln Arg Pro Asp Leu Ala
        205                 210                 215 gct gat aat cca att gat gat cac cat aca atg tat act gtt cac ttc      1361
Ala Asp Asn Pro Ile Asp Asp His His Thr Met Tyr Thr Val His Phe
```

```
Ala Asp Asn Pro Ile Asp Asp His His Thr Met Tyr Thr Val His Phe
    220             225             230 tac act ggt tca cat gct gct tca act gaa agc tat ccg tct gaa act    1409
Tyr Thr Gly Ser His Ala Ala Ser Thr Glu Ser Tyr Pro Ser Glu Thr
235                 240             245             250 cct aac tct gaa aga gga aac gta atg agt aac act cgt tat gcg tta    1457
Pro Asn Ser Glu Arg Gly Asn Val Met Ser Asn Thr Arg Tyr Ala Leu
                255             260             265 gaa aac gga gta gcg gta ttt gca aca gag tgg gga acg agt caa gct    1505
Glu Asn Gly Val Ala Val Phe Ala Thr Glu Trp Gly Thr Ser Gln Ala
            270             275             280 agt gga gac ggt ggt cct tac ttt gat gaa gca gat gta tgg att gaa    1553
Ser Gly Asp Gly Gly Pro Tyr Phe Asp Glu Ala Asp Val Trp Ile Glu
        285             290             295 ttt tta aat gaa aac aac att agc tgg gct aac tgg tct tta acg aat    1601
Phe Leu Asn Glu Asn Asn Ile Ser Trp Ala Asn Trp Ser Leu Thr Asn
    300             305             310 aaa aat gaa gta tct ggt gca ttt aca cca ttc gag tta ggt aag tct    1649
Lys Asn Glu Val Ser Gly Ala Phe Thr Pro Phe Glu Leu Gly Lys Ser
315             320             325             330 aac gca acc aat ctt gac cca ggt cca gat cat gtg tgg gca cca gaa    1697
Asn Ala Thr Asn Leu Asp Pro Gly Pro Asp His Val Trp Ala Pro Glu
                335             340             345 gaa tta agt ctt tct gga gaa tat gta cgt gct cgt att aaa ggt gtg    1745
Glu Leu Ser Leu Ser Gly Glu Tyr Val Arg Ala Arg Ile Lys Gly Val
            350             355             360 aac tat gag cca atc gac cgt aca aaa tac acg aaa gta ctt tgg gac    1793
Asn Tyr Glu Pro Ile Asp Arg Thr Lys Tyr Thr Lys Val Leu Trp Asp
        365             370             375 ttt aat gat gga acg aag caa gga ttt gga gtg aat tcg gat tct cca    1841
Phe Asn Asp Gly Thr Lys Gln Gly Phe Gly Val Asn Ser Asp Ser Pro
    380             385             390 aat aaa gaa ctt att gca gtt gat aat gaa aac aac act ttg aaa gtt    1889
Asn Lys Glu Leu Ile Ala Val Asp Asn Glu Asn Asn Thr Leu Lys Val
395             400             405             410 tcg gga tta gat gta agt aac gat gtt tca gat ggc aac ttc tgg gct    1937
Ser Gly Leu Asp Val Ser Asn Asp Val Ser Asp Gly Asn Phe Trp Ala
                415             420             425 aat gct cgt ctt tct gcc aac ggt tgg gga aaa agt gtt gat att tta    1985
Asn Ala Arg Leu Ser Ala Asn Gly Trp Gly Lys Ser Val Asp Ile Leu
            430             435             440 ggt gct gag aag ctt aca atg gat gtt att gtt gat gaa cca acg acg    2033
Gly Ala Glu Lys Leu Thr Met Asp Val Ile Val Asp Glu Pro Thr Thr
        445             450             455 gta gct att gcg gcg att cca caa agt agt aaa agt gga tgg gca aat    2081
Val Ala Ile Ala Ala Ile Pro Gln Ser Ser Lys Ser Gly Trp Ala Asn
    460             465             470 cca gag cgt gct gtt cga gtg aac gcg gaa gat ttt gtc cag caa acg    2129
Pro Glu Arg Ala Val Arg Val Asn Ala Glu Asp Phe Val Gln Gln Thr
475             480             485             490 gac ggt aag tat aaa gct gga tta aca att aca gga gaa gat gct cct    2177
Asp Gly Lys Tyr Lys Ala Gly Leu Thr Ile Thr Gly Glu Asp Ala Pro
                495             500             505 aac cta aaa aat atc gct ttt cat gaa gaa gat aac aat atg aac aac    2225
Asn Leu Lys Asn Ile Ala Phe His Glu Glu Asp Asn Asn Met Asn Asn
            510             515             520 atc att ctg ttc gtg gga act gat gca gct gac gtt att tac tta gat    2273
Ile Ile Leu Phe Val Gly Thr Asp Ala Ala Asp Val Ile Tyr Leu Asp
        525             530             535 aac att aaa gta att gga aca gaa gtt gaa att cca gtt gtt cat gat    2321
```

```
                Asn Ile Lys Val Ile Gly Thr Glu Val Glu Ile Pro Val Val His Asp
                    540                 545                 550 cca aaa gga gaa gct gtt ctt cct tct gtt ttt gaa gac ggt aca cgt        2369
Pro Lys Gly Glu Ala Val Leu Pro Ser Val Phe Glu Asp Gly Thr Arg
555                 560                 565                 570 caa ggt tgg gac tgg gct gga gag tct ggt gtg aaa aca gct tta aca        2417
Gln Gly Trp Asp Trp Ala Gly Glu Ser Gly Val Lys Thr Ala Leu Thr
                575                 580                 585 att gaa gaa gca aac ggt tct aac gcg tta tca tgg gaa ttt gga tat        2465
Ile Glu Glu Ala Asn Gly Ser Asn Ala Leu Ser Trp Glu Phe Gly Tyr
                590                 595                 600 cca gaa gta aaa cct agt gat aac tgg gca aca gct cca cgt tta gat        2513
Pro Glu Val Lys Pro Ser Asp Asn Trp Ala Thr Ala Pro Arg Leu Asp
                605                 610                 615 ttc tgg aaa tct gac ttg gtt cgc ggt gag aat gat tat gta gct ttt        2561
Phe Trp Lys Ser Asp Leu Val Arg Gly Glu Asn Asp Tyr Val Ala Phe
                620                 625                 630 gat ttc tat cta gat cca gtt cgt gca aca gaa ggc gca atg aat atc        2609
Asp Phe Tyr Leu Asp Pro Val Arg Ala Thr Glu Gly Ala Met Asn Ile
635                 640                 645                 650 aat tta gta ttc cag cca cct act aac ggg tat tgg gta caa gca cca        2657
Asn Leu Val Phe Gln Pro Pro Thr Asn Gly Tyr Trp Val Gln Ala Pro
                655                 660                 665 aaa acg tat acg att aac ttt gat gaa tta gag gaa gcg aat caa gta        2705
Lys Thr Tyr Thr Ile Asn Phe Asp Glu Leu Glu Glu Ala Asn Gln Val
                670                 675                 680 aat ggt tta tat cac tat gaa gtg aaa att aac gta aga gat att aca        2753
Asn Gly Leu Tyr His Tyr Glu Val Lys Ile Asn Val Arg Asp Ile Thr
                685                 690                 695 aac att caa gat gac acg tta cta cgt aac atg atg atc att ttt gca        2801
Asn Ile Gln Asp Asp Thr Leu Leu Arg Asn Met Met Ile Ile Phe Ala
700                 705                 710 gat gta gaa agt gac ttt gca ggg aga gtc ttt gta gat aat gtt cgt        2849
Asp Val Glu Ser Asp Phe Ala Gly Arg Val Phe Val Asp Asn Val Arg
715                 720                 725                 730 ttt gag ggg gct gct act act gag ccg gtt gaa cca gag cca gtt gat        2897
Phe Glu Gly Ala Ala Thr Thr Glu Pro Val Glu Pro Glu Pro Val Asp
                735                 740                 745 cct ggc gaa gag acg cca cct gtc gat gag aag gaa gcg aaa aaa gaa        2945
Pro Gly Glu Glu Thr Pro Pro Val Asp Glu Lys Glu Ala Lys Lys Glu
                750                 755                 760 caa aaa gaa gca gag aaa gaa gag aaa gaa gca gta aaa gaa gaa aag        2993
Gln Lys Glu Ala Glu Lys Glu Glu Lys Glu Ala Val Lys Glu Glu Lys
                765                 770                 775 aaa gaa gct aaa gaa gaa aag aaa gca gtc aaa aat gag gct aag aaa        3041
Lys Glu Ala Lys Glu Glu Lys Lys Ala Val Lys Asn Glu Ala Lys Lys
780                 785                 790 aaa taatctatta aactagttat agggttatct aaaggtctga tgtagatctt             3094
Lys
795 ttagataacc ttttcttgc ataactggac acagagttgt tattaaagaa agtaag           3150

<210> SEQ ID NO 116
<211> LENGTH: 824
<212> TYPE: PRT
<213> ORGANISM: Bacillus sp. KSM-S237

<400> SEQUENCE: 116

Met Met Leu Arg Lys Lys Thr Lys Gln Leu Ile Ser Ser Ile Leu Ile
            -25                 -20                 -15
```

```
Leu Val Leu Leu Leu Ser Leu Phe Pro Ala Ala Leu Ala Ala Glu Gly
            -10             -5              -1   1

Asn Thr Arg Glu Asp Asn Phe Lys His Leu Leu Gly Asn Asp Asn Val
         5              10             15

Lys Arg Pro Ser Glu Ala Gly Ala Leu Gln Leu Gln Glu Val Asp Gly
 20              25              30              35

Gln Met Thr Leu Val Asp Gln His Gly Glu Lys Ile Gln Leu Arg Gly
             40              45              50

Met Ser Thr His Gly Leu Gln Trp Phe Pro Glu Ile Leu Asn Asp Asn
             55              60              65

Ala Tyr Lys Ala Leu Ser Asn Asp Trp Asp Ser Asn Met Ile Arg Leu
         70              75              80

Ala Met Tyr Val Gly Glu Asn Gly Tyr Ala Thr Asn Pro Glu Leu Ile
 85              90              95

Lys Gln Arg Val Ile Asp Gly Ile Glu Leu Ala Ile Glu Asn Asp Met
100             105             110             115

Tyr Val Ile Val Asp Trp His Val His Ala Pro Gly Asp Pro Arg Asp
             120             125             130

Pro Val Tyr Ala Gly Ala Lys Asp Phe Phe Arg Glu Ile Ala Ala Leu
             135             140             145

Tyr Pro Asn Asn Pro His Ile Ile Tyr Glu Leu Ala Asn Glu Pro Ser
             150             155             160

Ser Asn Asn Asn Gly Gly Ala Gly Ile Pro Asn Asn Glu Glu Gly Trp
165             170             175

Lys Ala Val Lys Glu Tyr Ala Asp Pro Ile Val Glu Met Leu Arg Lys
180             185             190             195

Ser Gly Asn Ala Asp Asp Asn Ile Ile Ile Val Gly Ser Pro Asn Trp
             200             205             210

Ser Gln Arg Pro Asp Leu Ala Ala Asp Asn Pro Ile Asp Asp His His
             215             220             225

Thr Met Tyr Thr Val His Phe Tyr Thr Gly Ser His Ala Ala Ser Thr
             230             235             240

Glu Ser Tyr Pro Ser Glu Thr Pro Asn Ser Glu Arg Gly Asn Val Met
245             250             255

Ser Asn Thr Arg Tyr Ala Leu Glu Asn Gly Val Ala Val Phe Ala Thr
260             265             270             275

Glu Trp Gly Thr Ser Gln Ala Ser Gly Asp Gly Pro Tyr Phe Asp
             280             285             290

Glu Ala Asp Val Trp Ile Glu Phe Leu Asn Glu Asn Asn Ile Ser Trp
             295             300             305

Ala Asn Trp Ser Leu Thr Asn Lys Asn Glu Val Ser Gly Ala Phe Thr
             310             315             320

Pro Phe Glu Leu Gly Lys Ser Asn Ala Thr Asn Leu Asp Pro Gly Pro
325             330             335

Asp His Val Trp Ala Pro Glu Glu Leu Ser Leu Ser Gly Glu Tyr Val
340             345             350             355

Arg Ala Arg Ile Lys Gly Val Asn Tyr Glu Pro Ile Asp Arg Thr Lys
             360             365             370

Tyr Thr Lys Val Leu Trp Asp Phe Asn Asp Gly Thr Lys Gln Gly Phe
             375             380             385

Gly Val Asn Ser Asp Ser Pro Asn Lys Glu Leu Ile Ala Val Asp Asn
             390             395             400

Glu Asn Asn Thr Leu Lys Val Ser Gly Leu Asp Val Ser Asn Asp Val
405             410             415
```

```
Ser Asp Gly Asn Phe Trp Ala Asn Ala Arg Leu Ser Ala Asn Gly Trp
420                 425                 430                 435

Gly Lys Ser Val Asp Ile Leu Gly Ala Glu Lys Leu Thr Met Asp Val
            440                 445                 450

Ile Val Asp Glu Pro Thr Thr Val Ala Ile Ala Ala Ile Pro Gln Ser
                455                 460                 465

Ser Lys Ser Gly Trp Ala Asn Pro Glu Arg Ala Val Arg Val Asn Ala
        470                 475                 480

Glu Asp Phe Val Gln Gln Thr Asp Gly Lys Tyr Lys Ala Gly Leu Thr
485                 490                 495

Ile Thr Gly Glu Asp Ala Pro Asn Leu Lys Asn Ile Ala Phe His Glu
500                 505                 510                 515

Glu Asp Asn Asn Met Asn Asn Ile Ile Leu Phe Val Gly Thr Asp Ala
                520                 525                 530

Ala Asp Val Ile Tyr Leu Asp Asn Ile Lys Val Ile Gly Thr Glu Val
            535                 540                 545

Glu Ile Pro Val Val His Asp Pro Lys Gly Glu Ala Val Leu Pro Ser
        550                 555                 560

Val Phe Glu Asp Gly Thr Arg Gln Gly Trp Asp Trp Ala Gly Glu Ser
565                 570                 575

Gly Val Lys Thr Ala Leu Thr Ile Glu Glu Ala Asn Gly Ser Asn Ala
580                 585                 590                 595

Leu Ser Trp Glu Phe Gly Tyr Pro Glu Val Lys Pro Ser Asp Asn Trp
                600                 605                 610

Ala Thr Ala Pro Arg Leu Asp Phe Trp Lys Ser Asp Leu Val Arg Gly
            615                 620                 625

Glu Asn Asp Tyr Val Ala Phe Asp Phe Tyr Leu Asp Pro Val Arg Ala
        630                 635                 640

Thr Glu Gly Ala Met Asn Ile Asn Leu Val Phe Gln Pro Pro Thr Asn
645                 650                 655

Gly Tyr Trp Val Gln Ala Pro Lys Thr Tyr Thr Ile Asn Phe Asp Glu
660                 665                 670                 675

Leu Glu Glu Ala Asn Gln Val Asn Gly Leu Tyr His Tyr Glu Val Lys
                680                 685                 690

Ile Asn Val Arg Asp Ile Thr Asn Ile Gln Asp Asp Thr Leu Leu Arg
            695                 700                 705

Asn Met Met Ile Ile Phe Ala Asp Val Glu Ser Asp Phe Ala Gly Arg
        710                 715                 720

Val Phe Val Asp Asn Val Arg Phe Glu Gly Ala Ala Thr Thr Glu Pro
725                 730                 735

Val Glu Pro Glu Pro Val Asp Pro Gly Glu Thr Pro Pro Val Asp
740                 745                 750                 755

Glu Lys Glu Ala Lys Lys Glu Gln Lys Glu Ala Glu Lys Glu Lys
                760                 765                 770

Glu Ala Val Lys Glu Glu Lys Lys Glu Ala Lys Glu Glu Lys Lys Ala
            775                 780                 785

Val Lys Asn Glu Ala Lys Lys Lys
        790                 795

<210> SEQ ID NO 117
<211> LENGTH: 3332
<212> TYPE: DNA
<213> ORGANISM: Bacillus sp. KSM-64
<220> FEATURE:
<221> NAME/KEY: CDS
```

-continued

```
<222> LOCATION: (610)..(3075)
<220> FEATURE:
<221> NAME/KEY: sig_peptide
<222> LOCATION: (610)..(696)
<220> FEATURE:
<221> NAME/KEY: mat_peptide
<222> LOCATION: (697)..(3075)

<400> SEQUENCE: 117
agtacttacc attttagagt caaaagatag aagccaagca ggatttgccg atgcaaccgg    60
cttatattta gagggaattt cttttttaaat tgaatacgga ataaaatcag gtaaacaggt   120
cctgatttta ttttttttgaa ttttttttgag aactaaagat tgaaatagaa gtagaagaca   180
acggacataa gaaaattgta ttagttttaa ttatagaaaa cgcttttcta taattattta   240
tacctagaac gaaaatactg tttcgaaagc ggtttactat aaaaccttat attccggctc   300 ttttttttaaa caggggggtga aaattcactc tagtattcta atttcaacat gctataataa   360
atttgtaaga cgcaatatac atcttttttt tatgatattt gtaagcggtt aaccttgtgc   420
tatatgccga tttaggaagg gggtagattg agtcaagtag tcataattta gataacttat   480
aagttgttga gaagcaggag agaatctggg ttactcacaa gttttttaaa acattatcga   540
aagcactttc ggttatgctt atgaatttag ctatttgatt caattacttt aataatttta   600
```

```
ggaggtaat atg atg tta aga aag aaa aca aag cag ttg att tct tcc att    651
          Met Met Leu Arg Lys Lys Thr Lys Gln Leu Ile Ser Ser Ile
              -25                 -20 ctt att tta gtt tta ctt cta tct tta ttt ccg aca gct ctt gca gca     699
Leu Ile Leu Val Leu Leu Leu Ser Leu Phe Pro Thr Ala Leu Ala Ala
-15             -10                 -5              -1  1 gaa gga aac act cgt gaa gac aat ttt aaa cat tta tta ggt aat gac     747
Glu Gly Asn Thr Arg Glu Asp Asn Phe Lys His Leu Leu Gly Asn Asp
            5                   10                  15 aat gtt aaa cgc cct tct gag gct ggc gca tta caa tta caa gaa gtc     795
Asn Val Lys Arg Pro Ser Glu Ala Gly Ala Leu Gln Leu Gln Glu Val
        20                  25                  30 gat gga caa atg aca tta gta gat caa cat gga gaa aaa att caa tta     843
Asp Gly Gln Met Thr Leu Val Asp Gln His Gly Glu Lys Ile Gln Leu
    35                  40                  45 cgt gga atg agt aca cac gga tta caa tgg ttt cct gag atc ttg aat     891
Arg Gly Met Ser Thr His Gly Leu Gln Trp Phe Pro Glu Ile Leu Asn
50                  55                  60                  65 gat aac gca tac aaa gct ctt gct aac gat tgg gaa tca aat atg att     939
Asp Asn Ala Tyr Lys Ala Leu Ala Asn Asp Trp Glu Ser Asn Met Ile
                70                  75                  80 cgt cta gct atg tat gtc ggt gaa aat ggc tat gct tca aat cca gag     987
Arg Leu Ala Met Tyr Val Gly Glu Asn Gly Tyr Ala Ser Asn Pro Glu
            85                  90                  95 tta att aaa agc aga gtc att aaa gga ata gat ctt gct att gaa aat    1035
Leu Ile Lys Ser Arg Val Ile Lys Gly Ile Asp Leu Ala Ile Glu Asn
        100                 105                 110 gac atg tat gtc atc gtt gat tgg cat gta cat gca cct ggt gat cct    1083
Asp Met Tyr Val Ile Val Asp Trp His Val His Ala Pro Gly Asp Pro
    115                 120                 125 aga gat ccc gtt tac gct gga gca gaa gat ttc ttt aga gat att gca    1131
Arg Asp Pro Val Tyr Ala Gly Ala Glu Asp Phe Phe Arg Asp Ile Ala
130                 135                 140                 145 gca tta tat cct aac aat cca cac att att tat gag tta gcg aat gag    1179
Ala Leu Tyr Pro Asn Asn Pro His Ile Ile Tyr Glu Leu Ala Asn Glu
                150                 155                 160 cca agt agt aac aat aat ggt gga gct ggg att cca aat aat gaa gaa    1227
Pro Ser Ser Asn Asn Asn Gly Gly Ala Gly Ile Pro Asn Asn Glu Glu
```

```
                       165                 170                 175
ggt tgg aat gcg gta aaa gaa tac gct gat cca att gta gaa atg tta    1275
Gly Trp Asn Ala Val Lys Glu Tyr Ala Asp Pro Ile Val Glu Met Leu
            180                 185                 190 cgt gat agc ggg aac gca gat gac aat att atc att gtg ggt agt cca    1323
Arg Asp Ser Gly Asn Ala Asp Asp Asn Ile Ile Ile Val Gly Ser Pro
195                 200                 205 aac tgg agt cag cgt cct gac tta gca gct gat aat cca att gat gat    1371
Asn Trp Ser Gln Arg Pro Asp Leu Ala Ala Asp Asn Pro Ile Asp Asp
210                 215                 220                 225 cac cat aca atg tat act gtt cac ttc tac act ggt tca cat gct gct    1419
His His Thr Met Tyr Thr Val His Phe Tyr Thr Gly Ser His Ala Ala
            230                 235                 240 tca act gaa agc tat ccg cct gaa act cct aac tct gaa aga gga aac    1467
Ser Thr Glu Ser Tyr Pro Pro Glu Thr Pro Asn Ser Glu Arg Gly Asn
            245                 250                 255 gta atg agt aac act cgt tat gcg tta gaa aac gga gta gca gta ttt    1515
Val Met Ser Asn Thr Arg Tyr Ala Leu Glu Asn Gly Val Ala Val Phe
            260                 265                 270 gca aca gag tgg gga act agc caa gca aat gga gat ggt ggt cct tac    1563
Ala Thr Glu Trp Gly Thr Ser Gln Ala Asn Gly Asp Gly Gly Pro Tyr
275                 280                 285 ttt gat gaa gca gat gta tgg att gag ttt tta aat gaa aac aac att    1611
Phe Asp Glu Ala Asp Val Trp Ile Glu Phe Leu Asn Glu Asn Asn Ile
290                 295                 300                 305 agc tgg gct aac tgg tct tta acg aat aaa aat gaa gta tct ggt gca    1659
Ser Trp Ala Asn Trp Ser Leu Thr Asn Lys Asn Glu Val Ser Gly Ala
            310                 315                 320 ttt aca cca ttc gag tta ggt aag tct aac gca aca agt ctt gac cca    1707
Phe Thr Pro Phe Glu Leu Gly Lys Ser Asn Ala Thr Ser Leu Asp Pro
            325                 330                 335 ggg cca gac caa gta tgg gta cca gaa gag tta agt ctt tct gga gaa    1755
Gly Pro Asp Gln Val Trp Val Pro Glu Glu Leu Ser Leu Ser Gly Glu
            340                 345                 350 tat gta cgt gct cgt att aaa ggt gtg aac tat gag cca atc gac cgt    1803
Tyr Val Arg Ala Arg Ile Lys Gly Val Asn Tyr Glu Pro Ile Asp Arg
355                 360                 365 aca aaa tac acg aaa gta ctt tgg gac ttt aat gat gga acg aag caa    1851
Thr Lys Tyr Thr Lys Val Leu Trp Asp Phe Asn Asp Gly Thr Lys Gln
370                 375                 380                 385 gga ttt gga gtg aat gga gat tct cca gtt gaa gat gta gtt att gag    1899
Gly Phe Gly Val Asn Gly Asp Ser Pro Val Glu Asp Val Val Ile Glu
            390                 395                 400 aat gaa gcg ggc gct tta aaa ctt tca gga tta gat gca agt aat gat    1947
Asn Glu Ala Gly Ala Leu Lys Leu Ser Gly Leu Asp Ala Ser Asn Asp
            405                 410                 415 gtt tct gaa ggt aat tac tgg gct aat gct cgt ctt tct gcc gac ggt    1995
Val Ser Glu Gly Asn Tyr Trp Ala Asn Ala Arg Leu Ser Ala Asp Gly
            420                 425                 430 tgg gga aaa agt gtt gat att tta ggt gct gaa aaa ctt act atg gat    2043
Trp Gly Lys Ser Val Asp Ile Leu Gly Ala Glu Lys Leu Thr Met Asp
435                 440                 445 gtg att gtt gat gag ccg acc acg gta tca att gct gca att cca caa    2091
Val Ile Val Asp Glu Pro Thr Thr Val Ser Ile Ala Ala Ile Pro Gln
450                 455                 460                 465 ggg cca tca gcc aat tgg gtt aat cca aat cgt gca att aag gtt gag    2139
Gly Pro Ser Ala Asn Trp Val Asn Pro Asn Arg Ala Ile Lys Val Glu
            470                 475                 480 cca act aat ttc gta ccg tta gga gat aag ttt aaa gcg gaa tta act    2187
Pro Thr Asn Phe Val Pro Leu Gly Asp Lys Phe Lys Ala Glu Leu Thr
```

```
                    485                 490                 495
ata act tca gct gac tct cca tcg tta gaa gct att gcg atg cat gct       2235
Ile Thr Ser Ala Asp Ser Pro Ser Leu Glu Ala Ile Ala Met His Ala
            500                 505                 510 gaa aat aac aac atc aac aac atc att ctt ttt gta gga act gaa ggt       2283
Glu Asn Asn Asn Ile Asn Asn Ile Ile Leu Phe Val Gly Thr Glu Gly
515                 520                 525 gct gat gtt atc tat tta gat aac att aaa gta att gga aca gaa gtt       2331
Ala Asp Val Ile Tyr Leu Asp Asn Ile Lys Val Ile Gly Thr Glu Val
530                 535                 540                 545 gaa att cca gtt gtt cat gat cca aaa gga gaa gct gtt ctt cct tct       2379
Glu Ile Pro Val Val His Asp Pro Lys Gly Glu Ala Val Leu Pro Ser
            550                 555                 560 gtt ttt gaa gac ggt aca cgt caa ggt tgg gac tgg gct gga gag tct       2427
Val Phe Glu Asp Gly Thr Arg Gln Gly Trp Asp Trp Ala Gly Glu Ser
            565                 570                 575 ggt gtg aaa aca gct tta aca att gaa gaa gca aac ggt tct aac gcg       2475
Gly Val Lys Thr Ala Leu Thr Ile Glu Glu Ala Asn Gly Ser Asn Ala
            580                 585                 590 tta tca tgg gaa ttt gga tac cca gaa gta aaa cct agt gat aac tgg       2523
Leu Ser Trp Glu Phe Gly Tyr Pro Glu Val Lys Pro Ser Asp Asn Trp
595                 600                 605 gca aca gct cca cgt tta gat ttc tgg aaa tct gac ttg gtt cgc ggt       2571
Ala Thr Ala Pro Arg Leu Asp Phe Trp Lys Ser Asp Leu Val Arg Gly
610                 615                 620                 625 gaa aat gat tat gta act ttt gat ttc tat cta gat cca gtt cgt gca       2619
Glu Asn Asp Tyr Val Thr Phe Asp Phe Tyr Leu Asp Pro Val Arg Ala
            630                 635                 640 aca gaa ggc gca atg aat atc aat tta gta ttc cag cca cct act aac       2667
Thr Glu Gly Ala Met Asn Ile Asn Leu Val Phe Gln Pro Pro Thr Asn
            645                 650                 655 ggg tat tgg gta caa gca cca aaa acg tat acg att aac ttt gat gaa       2715
Gly Tyr Trp Val Gln Ala Pro Lys Thr Tyr Thr Ile Asn Phe Asp Glu
            660                 665                 670 tta gag gaa gcg aat caa gta aat ggt tta tat cac tat gaa gtg aaa       2763
Leu Glu Glu Ala Asn Gln Val Asn Gly Leu Tyr His Tyr Glu Val Lys
675                 680                 685 att aac gta aga gat att aca aac att caa gat gac acg tta cta cgt       2811
Ile Asn Val Arg Asp Ile Thr Asn Ile Gln Asp Asp Thr Leu Leu Arg
690                 695                 700                 705 aac atg atg atc att ttt gca gat gta gaa agt gac ttt gca ggg aga       2859
Asn Met Met Ile Ile Phe Ala Asp Val Glu Ser Asp Phe Ala Gly Arg
            710                 715                 720 gtc ttt gta gat aat gtt cgt ttt gag ggg gct gct act act gag ccg       2907
Val Phe Val Asp Asn Val Arg Phe Glu Gly Ala Ala Thr Thr Glu Pro
            725                 730                 735 gtt gaa cca gag cca gtt gat cct ggc gaa gag acg ccg cct gtc gat       2955
Val Glu Pro Glu Pro Val Asp Pro Gly Glu Glu Thr Pro Pro Val Asp
            740                 745                 750 gag aag gaa gcg aaa aaa gaa caa aaa gaa gca gag aaa gaa gag aaa       3003
Glu Lys Glu Ala Lys Lys Glu Gln Lys Glu Ala Glu Lys Glu Glu Lys
755                 760                 765 gaa gca gta aaa gaa gaa aag aaa gaa gct aaa gaa gaa aag aaa gca       3051
Glu Ala Val Lys Glu Glu Lys Lys Glu Ala Lys Glu Glu Lys Lys Ala
770                 775                 780                 785 atc aaa aat gag gct acg aaa aaa taatctaata aactagttat agggttatct      3105
Ile Lys Asn Glu Ala Thr Lys Lys
            790 aaaggtctga tgcagatctt ttagataacc ttttttttgca taactggaca tagaatggtt    3165
```

```
attaaagaaa gcaaggtgtt tatacgatat taaaaaggta gcgattttaa attgaaacct    3225
ttaataatgt cttgtgatag aatgatgaag taatttaaga gggggaaacg aagtgaaaac    3285
ggaaatttct agtagaagaa aaacagacca agaaatactg caagctt                 3332

<210> SEQ ID NO 118
<211> LENGTH: 822
<212> TYPE: PRT
<213> ORGANISM: Bacillus sp. KSM-64

<400> SEQUENCE: 118
```

Met Met Leu Arg Lys Lys Thr Lys Gln Leu Ile Ser Ser Ile Leu Ile
             -25                 -20                 -15

Leu Val Leu Leu Leu Ser Leu Phe Pro Thr Ala Leu Ala Ala Glu Gly
         -10                  -5                 -1   1

Asn Thr Arg Glu Asp Asn Phe Lys His Leu Leu Gly Asn Asp Asn Val
          5                  10                  15

Lys Arg Pro Ser Glu Ala Gly Ala Leu Gln Leu Gln Glu Val Asp Gly
 20                  25                  30                  35

Gln Met Thr Leu Val Asp Gln His Gly Glu Lys Ile Gln Leu Arg Gly
             40                  45                  50

Met Ser Thr His Gly Leu Gln Trp Phe Pro Glu Ile Leu Asn Asp Asn
         55                  60                  65

Ala Tyr Lys Ala Leu Ala Asn Asp Trp Glu Ser Asn Met Ile Arg Leu
     70                  75                  80

Ala Met Tyr Val Gly Glu Asn Gly Tyr Ala Ser Asn Pro Glu Leu Ile
 85                  90                  95

Lys Ser Arg Val Ile Lys Gly Ile Asp Leu Ala Ile Glu Asn Asp Met
100                 105                 110                 115

Tyr Val Ile Val Asp Trp His Val His Ala Pro Gly Asp Pro Arg Asp
             120                 125                 130

Pro Val Tyr Ala Gly Ala Glu Asp Phe Phe Arg Asp Ile Ala Ala Leu
         135                 140                 145

Tyr Pro Asn Asn Pro His Ile Ile Tyr Glu Leu Ala Asn Glu Pro Ser
     150                 155                 160

Ser Asn Asn Asn Gly Gly Ala Gly Ile Pro Asn Asn Glu Glu Gly Trp
165                 170                 175

Asn Ala Val Lys Glu Tyr Ala Asp Pro Ile Val Glu Met Leu Arg Asp
180                 185                 190                 195

Ser Gly Asn Ala Asp Asp Asn Ile Ile Ile Val Gly Ser Pro Asn Trp
             200                 205                 210

Ser Gln Arg Pro Asp Leu Ala Ala Asp Asn Pro Ile Asp Asp His His
         215                 220                 225

Thr Met Tyr Thr Val His Phe Tyr Thr Gly Ser His Ala Ala Ser Thr
     230                 235                 240

Glu Ser Tyr Pro Pro Glu Thr Pro Asn Ser Glu Arg Gly Asn Val Met
245                 250                 255

Ser Asn Thr Arg Tyr Ala Leu Glu Asn Gly Val Ala Val Phe Ala Thr
260                 265                 270                 275

Glu Trp Gly Thr Ser Gln Ala Asn Gly Asp Gly Gly Pro Tyr Phe Asp
             280                 285                 290

Glu Ala Asp Val Trp Ile Glu Phe Leu Asn Glu Asn Asn Ile Ser Trp
         295                 300                 305

Ala Asn Trp Ser Leu Thr Asn Lys Asn Glu Val Ser Gly Ala Phe Thr
     310                 315                 320

-continued

Pro Phe Glu Leu Gly Lys Ser Asn Ala Thr Ser Leu Asp Pro Gly Pro
325                 330                 335

Asp Gln Val Trp Val Pro Glu Glu Leu Ser Leu Ser Gly Glu Tyr Val
340                 345                 350                 355

Arg Ala Arg Ile Lys Gly Val Asn Tyr Glu Pro Ile Asp Arg Thr Lys
            360                 365                 370

Tyr Thr Lys Val Leu Trp Asp Phe Asn Asp Gly Thr Lys Gln Gly Phe
            375                 380                 385

Gly Val Asn Gly Asp Ser Pro Val Glu Asp Val Val Ile Glu Asn Glu
        390                 395                 400

Ala Gly Ala Leu Lys Leu Ser Gly Leu Asp Ala Ser Asn Asp Val Ser
405                 410                 415

Glu Gly Asn Tyr Trp Ala Asn Ala Arg Leu Ser Ala Asp Gly Trp Gly
420                 425                 430                 435

Lys Ser Val Asp Ile Leu Gly Ala Glu Lys Leu Thr Met Asp Val Ile
            440                 445                 450

Val Asp Glu Pro Thr Thr Val Ser Ile Ala Ala Ile Pro Gln Gly Pro
            455                 460                 465

Ser Ala Asn Trp Val Asn Pro Asn Arg Ala Ile Lys Val Glu Pro Thr
            470                 475                 480

Asn Phe Val Pro Leu Gly Asp Lys Phe Lys Ala Glu Leu Thr Ile Thr
485                 490                 495

Ser Ala Asp Ser Pro Ser Leu Glu Ala Ile Ala Met His Ala Glu Asn
500                 505                 510                 515

Asn Asn Ile Asn Asn Ile Ile Leu Phe Val Gly Thr Glu Gly Ala Asp
            520                 525                 530

Val Ile Tyr Leu Asp Asn Ile Lys Val Ile Gly Thr Glu Val Glu Ile
            535                 540                 545

Pro Val Val His Asp Pro Lys Gly Glu Ala Val Leu Pro Ser Val Phe
            550                 555                 560

Glu Asp Gly Thr Arg Gln Gly Trp Asp Trp Ala Gly Glu Ser Gly Val
565                 570                 575

Lys Thr Ala Leu Thr Ile Glu Glu Ala Asn Gly Ser Asn Ala Leu Ser
580                 585                 590                 595

Trp Glu Phe Gly Tyr Pro Glu Val Lys Pro Ser Asp Asn Trp Ala Thr
            600                 605                 610

Ala Pro Arg Leu Asp Phe Trp Lys Ser Asp Leu Val Arg Gly Glu Asn
            615                 620                 625

Asp Tyr Val Thr Phe Asp Phe Tyr Leu Asp Pro Val Arg Ala Thr Glu
            630                 635                 640

Gly Ala Met Asn Ile Asn Leu Val Phe Gln Pro Pro Thr Asn Gly Tyr
645                 650                 655

Trp Val Gln Ala Pro Lys Thr Tyr Thr Ile Asn Phe Asp Glu Leu Glu
660                 665                 670                 675

Glu Ala Asn Gln Val Asn Gly Leu Tyr His Tyr Glu Val Lys Ile Asn
            680                 685                 690

Val Arg Asp Ile Thr Asn Ile Gln Asp Asp Thr Leu Leu Arg Asn Met
            695                 700                 705

Met Ile Ile Phe Ala Asp Val Glu Ser Asp Phe Ala Gly Arg Val Phe
            710                 715                 720

Val Asp Asn Val Arg Phe Glu Gly Ala Ala Thr Thr Glu Pro Val Glu
            725                 730                 735

Pro Glu Pro Val Asp Pro Gly Glu Glu Thr Pro Pro Val Asp Glu Lys
740                 745                 750                 755

```
Glu Ala Lys Lys Glu Gln Lys Glu Ala Glu Lys Glu Lys Glu Ala
                760                 765                 770
Val Lys Glu Glu Lys Lys Glu Ala Lys Glu Glu Lys Lys Ala Ile Lys
            775                 780                 785
Asn Glu Ala Thr Lys Lys
            790

<210> SEQ ID NO 119
<211> LENGTH: 380
<212> TYPE: PRT
<213> ORGANISM: Bacillus clausii KSM-K16

<400> SEQUENCE: 119

Met Lys Lys Pro Leu Gly Lys Ile Val Ala Ser Thr Ala Leu Leu Ile
 1               5                  10                  15
Ser Val Ala Phe Ser Ser Ser Ile Ala Ser Ala Ala Glu Glu Ala Lys
            20                  25                  30
Glu Lys Tyr Leu Ile Gly Phe Asn Glu Gln Glu Ala Val Ser Glu Phe
        35                  40                  45
Val Glu Gln Ile Glu Ala Asn Asp Asp Val Ala Ile Leu Ser Glu Glu
 50                  55                  60
Glu Glu Val Glu Ile Glu Leu Leu His Glu Phe Glu Thr Ile Pro Val
 65                  70                  75                  80
Leu Ser Val Glu Leu Ser Pro Glu Asp Val Asp Ala Leu Glu Leu Asp
                 85                  90                  95
Pro Thr Ile Ser Tyr Ile Glu Glu Asp Ala Glu Val Thr Met Ala
                100                 105                 110
Gln Ser Val Pro Trp Gly Ile Ser Arg Val Gln Ala Pro Ala Ala His
            115                 120                 125
Asn Arg Gly Leu Thr Gly Ser Gly Val Lys Val Ala Val Leu Asp Thr
130                 135                 140
Gly Ile Ser Thr His Pro Asp Leu Asn Ile Arg Gly Gly Ala Ser Phe
145                 150                 155                 160
Val Pro Gly Glu Pro Ser Thr Gln Asp Gly Asn Gly His Gly Thr His
                165                 170                 175
Val Ala Gly Thr Ile Ala Ala Leu Asn Asn Ser Ile Gly Val Leu Gly
            180                 185                 190
Val Ala Pro Ser Ala Glu Leu Tyr Ala Val Lys Val Leu Gly Ala Ser
        195                 200                 205
Gly Ser Gly Ser Val Ser Ser Ile Ala Gln Gly Leu Glu Trp Ala Gly
210                 215                 220
Asn Asn Gly Met His Val Ala Asn Leu Ser Leu Gly Ser Pro Ser Pro
225                 230                 235                 240
Ser Ala Thr Leu Glu Gln Ala Val Asn Ser Ala Thr Ser Arg Gly Val
                245                 250                 255
Leu Val Val Ala Ala Ser Gly Asn Ser Gly Ala Gly Ser Ile Ser Tyr
            260                 265                 270
Pro Ala Arg Tyr Ala Asn Ala Met Ala Val Gly Ala Thr Asp Gln Asn
        275                 280                 285
Asn Asn Arg Ala Ser Phe Ser Gln Tyr Gly Ala Gly Leu Asp Ile Val
290                 295                 300
Ala Pro Gly Val Asn Val Gln Ser Thr Tyr Pro Gly Ser Thr Tyr Ala
305                 310                 315                 320
Ser Leu Asn Gly Thr Ser Met Ala Thr Pro His Val Ala Gly Val Ala
                325                 330                 335
```

```
Ala Leu Val Lys Gln Lys Asn Pro Ser Trp Ser Asn Val Gln Ile Arg
            340                 345                 350

Asn His Leu Lys Asn Thr Ala Thr Gly Leu Gly Asn Thr Asn Leu Tyr
            355                 360                 365

Gly Ser Gly Leu Val Asn Ala Glu Ala Ala Thr Arg
            370                 375                 380

<210> SEQ ID NO 120
<211> LENGTH: 480
<212> TYPE: PRT
<213> ORGANISM: Bacillus sp. KSM-K38

<400> SEQUENCE: 120

Asp Gly Leu Asn Gly Thr Met Met Gln Tyr Tyr Glu Trp His Leu Glu
  1               5                  10                  15

Asn Asp Gly Gln His Trp Asn Arg Leu His Asp Ala Ala Ala Leu
             20                  25                  30

Ser Asp Ala Gly Ile Thr Ala Ile Trp Ile Pro Pro Ala Tyr Lys Gly
         35                  40                  45

Asn Ser Gln Ala Asp Val Gly Tyr Gly Ala Tyr Asp Leu Tyr Asp Leu
 50                  55                  60

Gly Glu Phe Asn Gln Lys Gly Thr Val Arg Thr Lys Tyr Gly Thr Lys
 65                  70                  75                  80

Ala Gln Leu Glu Arg Ala Ile Gly Ser Leu Lys Ser Asn Asp Ile Asn
                 85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
            115                 120                 125

Ile Ser Gly Ala Tyr Thr Ile Asp Ala Trp Thr Gly Phe Asp Phe Ser
        130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
            245                 250                 255

Phe Val Val Gly Glu Tyr Trp Lys Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
    290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
            325                 330                 335
```

```
Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
            355                 360                 365

Ile Pro Asn Asp Asn Ile Ser Ala Lys Lys Asp Met Ile Asp Glu Leu
370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Arg
            405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
            435                 440                 445

Leu Thr Gly Asn Asn Gly Ala Ser Val Thr Ile Asn Gly Asp Gly Trp
            450                 455                 460

Gly Glu Phe Phe Thr Asn Gly Gly Ser Val Ser Val Tyr Val Asn Gln
465                 470                 475                 480
```

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of upp gene

<400> SEQUENCE: 121
agtcaacttc agcggtgttc                                                   20

<210> SEQ ID NO 122
<211> LENGTH: 43
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of upp
      gene and erythromycin resistant gene

<400> SEQUENCE: 122
gtgcgcggaa cccctatttg tcccatcaac aattacacac ttc                         43

<210> SEQ ID NO 123
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of upp
      gene and erythromycin resistant gene

<400> SEQUENCE: 123
cgttactaaa gggaatgtat gaaatcccca aaaggggg                               38

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of upp gene

<400> SEQUENCE: 124
gcggacgaaa tcaacaatcc                                                    20

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide as forward PCR primer for amplification of
      erythromycin resistant gene

<400> SEQUENCE: 125
acaaataggg gttccgcgca c                                                  21

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide as reverse PCR primer for amplification of
      erythromycin resistant gene

<400> SEQUENCE: 126
acattccctt tagtaacg                                                      18

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide as forward PCR primer for amplification of
      chloramphenicol resistant gene

<400> SEQUENCE: 127
cgcattaaag cttatcggca atagttaccc                                         30

<210> SEQ ID NO 128
<211> LENGTH: 64
<212> TYPE: DNA
<213> ORGANISM: Artificial Sequence
<220> FEATURE:
<223> OTHER INFORMATION: Description of Artificial Sequence:
      Oligonucleotide as reverse PCR primer for amplification of
      chloramphenicol resistant gene

<400> SEQUENCE: 128
gcccaagcgg gttttaggat catcgatccc ggaaatcgat tataggtatg tggttttgta        60
ttgg                                                                     64

<210> SEQ ID NO 129
<211> LENGTH: 71
<212> TYPE: DNA
<213> ORGANISM: Artificial Sequence
<220> FEATURE:
<223> OTHER INFORMATION: Description of Artificial Sequence:
      Oligonucleotide as forward PCR primer for amplification of upp
      gene

<400> SEQUENCE: 129
gccattccaa tacaaaacca catacctata atcgatgatc ctaaaacccg cttgggctta        60
tgcccggcgg g                                                             71

<210> SEQ ID NO 130
<211> LENGTH: 63
<212> TYPE: DNA

<213> ORGANISM: Artificial Sequence
<220> FEATURE:
<223> OTHER INFORMATION: Description of Artificial Sequence:
    Oligonucleotide as reverse PCR primer for amplification of upp
    gene

<400> SEQUENCE: 130

```
atcgatttcc ggtaccggaa ctcgagcctt gagctcaaaa aatcattcat ccgcaagcct    60
tgc                                                                  63
```

<210> SEQ ID NO 131
<211> LENGTH: 27
<212> TYPE: DNA
<213> ORGANISM: Artificial Sequence
<220> FEATURE:
<223> OTHER INFORMATION: Description of Artificial Sequence:
    Oligonucleotide as PCR primer for upstream region of ybbU gene

<400> SEQUENCE: 131

```
ctgcaaacgc aatggaagct ctatgcg                                        27
```

<210> SEQ ID NO 132
<211> LENGTH: 60
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of ybbU
    gene and chloramphenicol resistant gene

<400> SEQUENCE: 132

```
gggtaactat tgccgataag ctttaatgcg ataaaaacac ccctttagat aatcttatcc    60
```

<210> SEQ ID NO 133
<211> LENGTH: 60
<212> TYPE: DNA
<213> ORGANISM: Artificial Sequence
<220> FEATURE:
<223> OTHER INFORMATION: Description of Artificial Sequence:
    Oligonucleotide as SOE-PCR primer for downstream region of ybdE
    gene and upp gene

<400> SEQUENCE: 133

```
aaggctcgag ttccggtacc ggaaatcgat aaatttccgt cttgtatgtg cgacaaacgg    60
```

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence:
    Oligonucleotide as PCR primer for downstream region of ybdE
    gene

<400> SEQUENCE: 134

```
tgaaaacttg ctgtacagcc cc                                             22
```

<210> SEQ ID NO 135
<211> LENGTH: 60
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of ybbU
    gene and downstream region of ybdE gene

<400> SEQUENCE: 135

```
ccgtttgtcg cacatacaag acggaaattt ataaaaacac ccctttagat aatcttatcc    60
```

<210> SEQ ID NO 136
<211> LENGTH: 60
<212> TYPE: DNA
<213> ORGANISM: Artificial Sequence
<220> FEATURE:
<223> OTHER INFORMATION: Description of Artificial Sequence:
Oligonucleotide as SOE-PCR primer for downstream region of ybdE
gene and upstream region of ybbU gene

<400> SEQUENCE: 136
ggataagatt atctaaaggg gtgtttttat aaatttccgt cttgtatgtg cgacaaacgg    60

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence:
Oligonucleotide as PCR primer for upstream region of ydiM gene

<400> SEQUENCE: 137
ccagatttag atggaaagcc                                                20

<210> SEQ ID NO 138
<211> LENGTH: 56
<212> TYPE: DNA
<213> ORGANISM: Artificial Sequence
<220> FEATURE:
<223> OTHER INFORMATION: Description of Artificial Sequence:
Oligonucleotide as SOE-PCR primer for upstream region of ydiM
gene and chloramphenicol resistant gene

<400> SEQUENCE: 138
gggtaactat tgccgataag ctttaatgcg ataaaaggg gcagaactga ttcagc         56

<210> SEQ ID NO 139
<211> LENGTH: 60
<212> TYPE: DNA
<213> ORGANISM: Artificial Sequence
<220> FEATURE:
<223> OTHER INFORMATION: Description of Artificial Sequence:
Oligonucleotide as SOE-PCR primer for downstream region of ydjC
gene and upp gene

<400> SEQUENCE: 139
aaggctcgag ttccggtacc ggaaatcgat atttgtagac tttaataaga aacgaaaggc    60

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence:
Oligonucleotide as PCR primer for downstream region of ydjC gene

<400> SEQUENCE: 140
tcacgatgcc tatgatctaa aggtttgggg                                     30

<210> SEQ ID NO 141
<211> LENGTH: 60
<212> TYPE: DNA
<213> ORGANISM: Artificial Sequence
<220> FEATURE:
<223> OTHER INFORMATION: Description of Artificial Sequence:
Oligonucleotide as SOE-PCR primer for upstream region of ydiM
gene and downstream region of ydjC gene

<400> SEQUENCE: 141
gcctttcgtt tcttattaaa gtctacaaat ccccaatcaa atagatggaa aattaggctc    60

<210> SEQ ID NO 142
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ydjC
      gene and upstream region of ydiM gene

<400> SEQUENCE: 142
gagcctaatt ttccatctat ttgattgggg atttgtagac tttaataaga aacgaaaggc    60

<210> SEQ ID NO 143
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yjcM gene

<400> SEQUENCE: 143
gccagtccaa gaccgtcact tcagccatgc                                     30

<210> SEQ ID NO 144
<211> LENGTH: 67
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yjcM
      gene and chloramphenicol resistant gene

<400> SEQUENCE: 144
gggtaactat tgccgataag ctttaatgcg ataaaaaatg ccttccgcta cttaataagc    60
tgttggg                                                              67

<210> SEQ ID NO 145
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yjdJ
      gene and upp gene

<400> SEQUENCE: 145
aaggctcgag ttccggtacc ggaaatcgat tgtgtggctc ttttttgcatc              50

<210> SEQ ID NO 146
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yjdJ gene

<400> SEQUENCE: 146
cggtatgggt gaaacgaacg tctgtgtgga gc                                  32

<210> SEQ ID NO 147
<211> LENGTH: 40
<212> TYPE: DNA
<213> ORGANISM: Artificial Sequence
<220> FEATURE:
<223> OTHER INFORMATION: Description of Artificial Sequence:

Oligonucleotide as SOE-PCR primer for upstream region of yjcM
gene and downstream region of yjdJ gene

<400> SEQUENCE: 147
gatgcaaaaa gagccacaca ctacttaata agctgttggg          40

<210> SEQ ID NO 148
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yjdJ
      gene and upstream region of yjcM gene

<400> SEQUENCE: 148
cccaacagct tattaagtag tgtgtggctc tttttgcatc          40

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yrkM gene

<400> SEQUENCE: 149
tccgcactac acattgccgt gataaatggg          30

<210> SEQ ID NO 150
<211> LENGTH: 67
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yrkM
      gene and chloramphenicol resistant gene

<400> SEQUENCE: 150
gggtaactat tgccgataag ctttaatgcg ataaaaacat tattccttc ctctgataat     60 gaaatat          67

<210> SEQ ID NO 151
<211> LENGTH: 62
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yraK
      gene and upp gene

<400> SEQUENCE: 151
aaggctcgag ttccggtacc ggaaatcgat cggaacaatt ggaaacagaa tgggttgaat     60
tc          62

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yraK gene

<400> SEQUENCE: 152
gcctcatgag ctgccaatgt ttgatgatcc          30

```
<210> SEQ ID NO 153
<211> LENGTH: 62
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yrkM
      gene and downstream region of yraK gene

<400> SEQUENCE: 153
gaattcaacc cattctgttt ccaattgttc cgcattatta ccttcctctg ataatgaaat    60
at                                                                   62

<210> SEQ ID NO 154
<211> LENGTH: 62
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yraK
      gene and upstream region of yrkM gene

<400> SEQUENCE: 154
atatttcatt atcagaggaa ggtaataatg cggaacaatt ggaaacagaa tgggttgaat    60
tc                                                                   62

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ykdA gene

<400> SEQUENCE: 155
tgcggaggcc caaggacgcc                                                20

<210> SEQ ID NO 156
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ykdA
      gene and chloramphenicol resistant gene

<400> SEQUENCE: 156
gggtaactat tgccgataag ctttaatgcg ataaaaaatc agcagcactt gcaggtcgct    60

<210> SEQ ID NO 157
<211> LENGTH: 52
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of xlyA
      gene and upp gene

<400> SEQUENCE: 157
aaggctcgag ttccggtacc ggaaatcgat gcgacgaaag agaagatcgc ag            52

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of xlyA gene
```

<400> SEQUENCE: 158
gtctgacagc attgtcacgg                                           20

<210> SEQ ID NO 159
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ykdA
      gene and downstream region of xlyA gene

<400> SEQUENCE: 159
gcgatcttct ctttcgtcgc cagcagcact tgcaggtcgc                     40

<210> SEQ ID NO 160
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of xlyA
      gene and upstream region of ykdA gene

<400> SEQUENCE: 160
gcgacctgca agtgctgctg gcgacgaaag agaagatcgc                     40

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yodU gene

<400> SEQUENCE: 161
tttttcccta gttacgtccg                                           20

<210> SEQ ID NO 162
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yodU
      gene and chloramphenicol resistant gene

<400> SEQUENCE: 162
gggtaactat tgccgataag ctttaatgcg ataaaaatgt actgatatta atgacatgc     59

<210> SEQ ID NO 163
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ypqP
      gene and upp gene

<400> SEQUENCE: 163
aaggctcgag ttccggtacc ggaaatcgat gctgtatctc ctgtgaacac aatgggtgcc    60

<210> SEQ ID NO 164
<211> LENGTH: 20
<212> TYPE: DNA
<213> ORGANISM: Artificial Sequence
<220> FEATURE:

```
<223> OTHER INFORMATION: Description of Artificial Sequence:
      Oligonucleotide as PCR primer for downstream region of ypqP
      gene

<400> SEQUENCE: 164
tctttcgtaa tgagcggggc                                                    20

<210> SEQ ID NO 165
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yodU
      gene and downstream region of ypqP gene

<400> SEQUENCE: 165
gtgttcacag gagatacagc tactgatatt aatgacatgc                              40

<210> SEQ ID NO 166
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ypqP
      gene and upstream region of yodU gene

<400> SEQUENCE: 166
gcatgtcatt aatatcagta gctgtatctc ctgtgaacac                              40

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of pksA gene

<400> SEQUENCE: 167
ctgcaagcgc gatggccgcg                                                    20

<210> SEQ ID NO 168
<211> LENGTH: 67
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of pksA
      gene and chloramphenicol resistant gene

<400> SEQUENCE: 168
gggtaactat tgccgataag ctttaatgcg ataaaaaatg tccttaattc ggtccgttac        60
cttttct                                                                  67

<210> SEQ ID NO 169
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ymaC
      gene and upp gene

<400> SEQUENCE: 169
aaggctcgag ttccggtacc ggaaatcgat aaatcaagga gcatcaatat gtggtggctt        60
```

```
<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ymaC gene

<400> SEQUENCE: 170
cgataggagc agccatgctg                                              20

<210> SEQ ID NO 171
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of pksA
      gene and downstream region of ymaC gene

<400> SEQUENCE: 171
ccaccacata ttgatgctcc ccttaattcg gtccgttacc                        40

<210> SEQ ID NO 172
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ymaC
      gene and upstream region of pksA gene

<400> SEQUENCE: 172
ggtaacggac cgaattaagg ggagcatcaa tatgtggtgg                        40

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ydcL gene

<400> SEQUENCE: 173
agttctcaac catcggcccg                                              20

<210> SEQ ID NO 174
<211> LENGTH: 57
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ydcL
      gene and chloramphenicol resistant gene

<400> SEQUENCE: 174
gggtaactat tgccgataag ctttaatgcg ataaaaataa gtgggcagtt tgtgggc     57

<210> SEQ ID NO 175
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ydeJ
      gene and upp gene

<400> SEQUENCE: 175
aaggctcgag ttccggtacc ggaaatcgat accatggaat agataggatg             50
```

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ydeJ gene

<400> SEQUENCE: 176
aactttcacg gcgtctgggg                                            20

<210> SEQ ID NO 177
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ydcL
      gene and downstream region of ydeJ gene

<400> SEQUENCE: 177
catcctatct attccatggt taagtgggca gtttgtgggc                      40

<210> SEQ ID NO 178
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ydeJ
      gene and upstream region of ydcL gene

<400> SEQUENCE: 178
gcccacaaac tgcccactta accatggaat agataggatg                      40

<210> SEQ ID NO 179
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ynxB gene

<400> SEQUENCE: 179
tagcgtattg cttgctgcag gattagacgg                                 30

<210> SEQ ID NO 180
<211> LENGTH: 67
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ynxB
      gene and chloramphenicol resistant gene

<400> SEQUENCE: 180
gggtaactat tgccgataag ctttaatgcg ataaaaaaga tttcaacgta attatggatt  60
catttgg                                                          67

<210> SEQ ID NO 181
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of dut
      gene and upp gene

<400> SEQUENCE: 181
aaggctcgag ttccggtacc ggaaatcgat tctccatgct gtgtgattga tcaatggagg    60

<210> SEQ ID NO 182
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of dut gene

<400> SEQUENCE: 182
ctatttattc cctggcgaca taccgggggc                                     30

<210> SEQ ID NO 183
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ynxB
      gene and downstream region of dut gene

<400> SEQUENCE: 183
cctccattga tcaatcacac agcatggaga agatttcaac gtaattatgg attcatttgg    60

<210> SEQ ID NO 184
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of dut
      gene and upstream region of ynxB gene

<400> SEQUENCE: 184
ccaaatgaat ccataattac gttgaaatct tctccatgct gtgtgattga tcaatggagg    60

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yoaV gene

<400> SEQUENCE: 185
aattcatgac atcccccgc                                                 20

<210> SEQ ID NO 186
<211> LENGTH: 67
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yoaV
      gene and chloramphenicol resistant gene

<400> SEQUENCE: 186
gggtaactat tgccgataag ctttaatgcg ataaaaaaat cccgcagcat atcagcagtg    60
cgccgag                                                              67

<210> SEQ ID NO 187
<211> LENGTH: 60
<212> TYPE: DNA
<213> ORGANISM: Artificial Sequence

```
<220> FEATURE:
<223> OTHER INFORMATION: Description of Artificial Sequence:
      Oligonucleotide as SOE-PCR primer for downstream region of yobO
      gene and upp gene

<400> SEQUENCE: 187
aaggctcgag ttccggtacc ggaaatcgat cacacacgaa tgtggcgtgt ggtgcatcgc    60

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yobO gene

<400> SEQUENCE: 188
catcgcttcc gttctatcgg                                                20

<210> SEQ ID NO 189
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yoaV
      gene and downstream region of yobO gene

<400> SEQUENCE: 189
ggagggcgaa ggaatgcaag tgaagcccaa atgacagggg                          40

<210> SEQ ID NO 190
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yobO
      gene and upstream region of yoaV gene

<400> SEQUENCE: 190
cccctgtcat ttgggcttca cttgcattcc ttcgccctcc                          40

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of spoIVCB
      gene

<400> SEQUENCE: 191
accacttcgg ctcattaccc                                                20

<210> SEQ ID NO 192
<211> LENGTH: 57
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of spoIVCB
      gene and chloramphenicol resistant gene

<400> SEQUENCE: 192
gggtaactat tgccgataag ctttaatgcg ataaaaagtc acctccacaa aagtatg       57

<210> SEQ ID NO 193
```

```
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      spoIIIC gene and upp gene

<400> SEQUENCE: 193
aaggctcgag ttccggtacc ggaaatcgat cagaagaagc cggatctc                48

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of spoIIIC
      gene

<400> SEQUENCE: 194
tgttcaacaa agtggacagc                                               20

<210> SEQ ID NO 195
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of
      spoIVCB gene and downstream region of spoIIIC gene

<400> SEQUENCE: 195
gagatccggc ttcttctgca cgtcacctcc acaaaagtat g                       41

<210> SEQ ID NO 196
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      spoIIIC gene and upstream region of spoIVCB gene

<400> SEQUENCE: 196 catactttg tggaggtgac gtgcagaaga agccggatct c                        41

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ppsE gene

<400> SEQUENCE: 197
catcctgccc tcgaaggcgc                                               20

<210> SEQ ID NO 198
<211> LENGTH: 68
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ppsE
      gene and chloramphenicol resistant gene

<400> SEQUENCE: 198
gggtaactat tgccgataag ctttaatgcg ataaaaaacg gattccctcc agttctcata   60
``` ataagagg    68

<210> SEQ ID NO 199
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ppsA
      gene and upp gene

<400> SEQUENCE: 199
aaggctcgag ttccggtacc ggaaatcgat agcggattag cggacagagg ccattctctg    60

<210> SEQ ID NO 200
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ppsA gene

<400> SEQUENCE: 200
tccggtcggg tcatctgcgg cg    22

<210> SEQ ID NO 201
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ppsE
      gene and downstream region of ppsA gene

<400> SEQUENCE: 201
ggcctctgtc cgctaatccg ccagttctca taataagagg    40

<210> SEQ ID NO 202
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ppsA
      gene and upstream region of ppsE gene

<400> SEQUENCE: 202
cctcttatta tgagaactgg cggattagcg gacagaggcc    40

<210> SEQ ID NO 203
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yodU
      gene and tetracycline resistant gene

<400> SEQUENCE: 203
gtaaataagc tgttcatatc tgtactgata ttaatgacat gc    42

<210> SEQ ID NO 204
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ypqP gene and tetracycline resistant gene

<400> SEQUENCE: 204
cccgcttggg cttatgcccg gctgtatctc ctgtgaacac aatgggtgcc        50

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as forward PCR primer for amplification of
      tetracycline resistant gene

<400> SEQUENCE: 205
tcctaatatc ggttatgaag        20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as reverse PCR primer for amplification of
      tetracycline resistant gene

<400> SEQUENCE: 206
tacattcaag gtaaccagcc        20

<210> SEQ ID NO 207
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of pksA
      gene and tetracycline resistant gene

<400> SEQUENCE: 207
gtaaataagc tgttcatatc atgtccttaa ttcggtccgt tacctttct        50

<210> SEQ ID NO 208
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ymaC
      gene and tetracycline resistant gene

<400> SEQUENCE: 208
cccgcttggg cttatgcccg aaatcaagga gcatcaatat gtggtggctt        50

<210> SEQ ID NO 209
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of
      spoIVCB gene and tetracycline resistant gene

<400> SEQUENCE: 209
gtaaataagc tgttcatatc gtcacctcca caaaagtatg        40

<210> SEQ ID NO 210
<211> LENGTH: 38
<212> TYPE: DNA

```
<213> ORGANISM: Artificial Sequence
<220> FEATURE:
<223> OTHER INFORMATION: Description of Artificial Sequence:
      Oligonucleotide as SOE-PCR primer for downstream region of
      spoIIIC gene and tetracycline resistant gene

<400> SEQUENCE: 210
cccgcttggg cttatgcccg cagaagaagc cggatctc                              38

<210> SEQ ID NO 211
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ppsE
      gene and tetracycline resistant gene

<400> SEQUENCE: 211
gtaaataagc tgttcatatc acggattccc tccagttctc ataataagag g               51

<210> SEQ ID NO 212
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ppsA
      gene and tetracycline resistant gene

<400> SEQUENCE: 212
cccgcttggg cttatgcccg agcggattag cggacagagg ccattctctg                 50

<210> SEQ ID NO 213
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ydcL
      gene and tetracycline resistant gene

<400> SEQUENCE: 213
gtaaataagc tgttcatatc taagtgggca gtttgtgggc                            40

<210> SEQ ID NO 214
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ydeJ
      gene and tetracycline resistant gene

<400> SEQUENCE: 214
cccgcttggg cttatgcccg accatggaat agataggatg                            40

<210> SEQ ID NO 215
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ynxB
      gene and tetracycline resistant gene

<400> SEQUENCE: 215
gtaaataagc tgttcatatc agatttcaac gtaattatgg attcatttgg                 50
```

```
<210> SEQ ID NO 216
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of dut
      gene and tetracycline resistant gene

<400> SEQUENCE: 216
cccgcttggg cttatgcccg tctccatgct gtgtgattga tcaatggagg            50

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ycxB gene

<400> SEQUENCE: 217
gaaacatgcg cacgtctccc                                            20

<210> SEQ ID NO 218
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ycxB
      gene and tetracycline resistant gene

<400> SEQUENCE: 218
gtaaataagc tgttcatatc cagtgctgat cctttatat                       40

<210> SEQ ID NO 219
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of sipU
      gene and tetracycline resistant gene

<400> SEQUENCE: 219
cccgcttggg cttatgcccg gcaatgcaaa aagaacatgg                      40

<210> SEQ ID NO 220
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of sipU
      gene

<400> SEQUENCE: 220
ggggaccact ttgtacaaga aagctgggta actctcaaag cgaacggg             48

<210> SEQ ID NO 221
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ycxB
      gene and downstream region of sipU gene

<400> SEQUENCE: 221
```
ccatgttctt tttgcattgc cagtgctgat cctttttatat        40

<210> SEQ ID NO 222
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of sipU
      gene and upstream region of ycxB gene

<400> SEQUENCE: 222
atataaaagg atcagcactg gcaatgcaaa aagaacatgg        40

<210> SEQ ID NO 223
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ydcL gene

<400> SEQUENCE: 223
ggggacaagt ttgtacaaaa aagcaggcta gtatctgtac gacctgcggc c        51

<210> SEQ ID NO 224
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ydcL
      gene and tetracycline resistant gene

<400> SEQUENCE: 224
gtaaataagc tgttcatatc taagtgggca gtttgtgggc        40

<210> SEQ ID NO 225
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      ydhU gene and tetracycline resistant gene

<400> SEQUENCE: 225
cccgcttggg cttatgcccg acccgttcca cggattgccc        40

<210> SEQ ID NO 226
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ydhU gene

<400> SEQUENCE: 226
atgccggtac ctggctcgag gacctgcatc gtgcaggccc        40

<210> SEQ ID NO 227
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ydcL
      gene and downstream region of ydhU gene

<400> SEQUENCE: 227
gggcaatccg tggaacgggt taagtgggca gtttgtgggc                          40

<210> SEQ ID NO 228
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      ydhU gene and upstream region of ydcL gene

<400> SEQUENCE: 228
gcccacaaac tgcccactta acccgttcca cggattgccc                          40

<210> SEQ ID NO 229
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ydiM gene

<400> SEQUENCE: 229
ttttgtgttt tgctaatcgg gtattgaccc                                     30

<210> SEQ ID NO 230
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ydiM
      gene and tetracycline resistant gene

<400> SEQUENCE: 230
gtaaataagc tgttcatatc aattttcacc tcacatcgct                          40

<210> SEQ ID NO 231
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yebA
      gene and tetracycline resistant gene

<400> SEQUENCE: 231
cccgcttggg cttatgcccg agattcttcg gcgctatgga                          40

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yebA gene

<400> SEQUENCE: 232
tccgcttcat catcaaacac                                                20

<210> SEQ ID NO 233
<211> LENGTH: 40
<212> TYPE: DNA
<213> ORGANISM: Artificial Sequence
<220> FEATURE:
<223> OTHER INFORMATION: Description of Artificial Sequence:

Oligonucleotide as SOE-PCR primer for upstream region of ydiM gene and downstream region of yebA gene

<400> SEQUENCE: 233
tccatagcgc cgaagaatct aattttcacc tcacatcgct        40

<210> SEQ ID NO 234
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yebA gene and upstream region of ydiM gene

<400> SEQUENCE: 234
agcgatgtga ggtgaaaatt agattcttcg gcgctatgga        40

<210> SEQ ID NO 235
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yeeK gene

<400> SEQUENCE: 235
aaaaagcagg ctagctcgag agatattcta aagggagag         40

<210> SEQ ID NO 236
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yeeK
      gene and tetracycline resistant gene

<400> SEQUENCE: 236
gtaaataagc tgttcatatc atttactctc tccttcacat        40

<210> SEQ ID NO 237
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yesX
      gene and tetracycline resistant gene

<400> SEQUENCE: 237
cccgcttggg cttatgcccg gaggactaag ggataagacg        40

<210> SEQ ID NO 238
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yesX gene

<400> SEQUENCE: 238
aagaaagctg ggtactcgag gctgtggtga tgatggcggc        40

<210> SEQ ID NO 239
<211> LENGTH: 40
<212> TYPE: DNA
<213> ORGANISM: Artificial Sequence

```
<220> FEATURE:
<223> OTHER INFORMATION: Description of Artificial Sequence:
      Oligonucleotide as SOE-PCR primer for upstream region of yeeK
      gene and downstream region of yesX gene

<400> SEQUENCE: 239
cgtcttatcc cttagtcctc atttactctc tccttcacat                              40

<210> SEQ ID NO 240
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yesX gene and upstream region of yeeK gene

<400> SEQUENCE: 240
atgtgaagga gagagtaaat gaggactaag ggataagacg                              40

<210> SEQ ID NO 241
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of cspB gene

<400> SEQUENCE: 241
aaaaagcagg ctagctcgag gagcagccga gtgaagccgc                              40

<210> SEQ ID NO 242
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of cspB
      gene and tetracycline resistant gene

<400> SEQUENCE: 242
gtaaataagc tgttcatatc aaattgatat gaaaaactgc                              40

<210> SEQ ID NO 243
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yhcT gene and tetracycline resistant gene

<400> SEQUENCE: 243
cccgcttggg cttatgcccg gttaaatggc tccttttcga                              40

<210> SEQ ID NO 244
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yhcT
      gene

<400> SEQUENCE: 244
aagaaagctg ggtactcgag gtatctagaa taagcccgtc                              40

<210> SEQ ID NO 245
```

```
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of
      cspB gene and downstream region of yhcT gene

<400> SEQUENCE: 245
tcgaaaagga gccatttaac aaattgatat gaaaaactgc                              40

<210> SEQ ID NO 246
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yhcT gene and upstream region of cspB gene

<400> SEQUENCE: 246 gcagttttc atatcaattt gttaaatggc tccttttcga                               40

<210> SEQ ID NO 247
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yncM gene

<400> SEQUENCE: 247
aaaaagcagg ctagctcgag atggaatctc agacgaagag                              40

<210> SEQ ID NO 248
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yncM
      gene and tetracycline resistant gene

<400> SEQUENCE: 248
gtaaataagc tgttcatatc acgaagcagc aaaaagccgc                              40

<210> SEQ ID NO 249
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      fosB gene and tetracycline resistant gene

<400> SEQUENCE: 249
cccgcttggg cttatgcccg caaccatatt tcatataagg                              40

<210> SEQ ID NO 250
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of fosB
      gene

<400> SEQUENCE: 250
aagaaagctg ggtactcgag aaggcaactt gatatcctcc                              40
```

<210> SEQ ID NO 251
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of yncM
    gene and downstream region of fosB gene

<400> SEQUENCE: 251
ccttatatga aatatggttg acgaagcagc aaaaagccgc                40

<210> SEQ ID NO 252
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for downstream region of
    fosB gene and upstream region of yncM gene

<400> SEQUENCE: 252
gcggcttttt gctgcttcgt caaccatatt tcatataagg                40

<210> SEQ ID NO 253
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as PCR primer for upstream region of cgeE gene

<400> SEQUENCE: 253
aaaaagcagg ctagctcgag ctcataatca cacctgaccc                40

<210> SEQ ID NO 254
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of cgeE
    gene and tetracycline resistant gene

<400> SEQUENCE: 254
gtaaataagc tgttcatatc aataggcgtt tgcacaaacc                40

<210> SEQ ID NO 255
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for downstream region of
    ypmQ gene and tetracycline resistant gene

<400> SEQUENCE: 255
cccgcttggg cttatgcccg gacatccatc ctttccagcc                40

<210> SEQ ID NO 256
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as PCR primer for downstream region of ypmQ gene

<400> SEQUENCE: 256
aagaaagctg ggtactcgag ggccttctct ctggggtagg                    40

<210> SEQ ID NO 257
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of cgeE
      gene and downstream region of ypmQ gene

<400> SEQUENCE: 257
ggctggaaag gatggatgtc aataggcgtt tgcacaaacc                    40

<210> SEQ ID NO 258
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ypmQ
      gene and upstream region of cgeE gene

<400> SEQUENCE: 258
ggtttgtgca aacgcctatt gacatccatc ctttccagcc                    40

<210> SEQ ID NO 259
<211> LENGTH: 52
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yraK gene and tetracycline resistant gene

<400> SEQUENCE: 259
cccgcttggg cttatgcccg cggaacaatt ggaaacagaa tgggttgaat tc      52

<210> SEQ ID NO 260
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of
      spoIVCB gene and downstream region of yraK gene

<400> SEQUENCE: 260
gaattcaacc cattctgttt ccaattgttc cgcgtcacct ccacaaaagt atg     53

<210> SEQ ID NO 261
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yraK gene and upstream region of spoIVCB gene

<400> SEQUENCE: 261 catactttg tggaggtgac gcggaacaat tggaaacaga atgggttgaa ttc      53

<210> SEQ ID NO 262
<211> LENGTH: 40
<212> TYPE: DNA
<213> ORGANISM: Artificial Sequence
<220> FEATURE:
<223> OTHER INFORMATION: Description of Artificial Sequence:

Oligonucleotide as PCR primer for upstream region of ytxK gene

<400> SEQUENCE: 262
aaaaagcagg ctagctcgag gtagcttcaa cgatgtcacg        40

<210> SEQ ID NO 263
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of ytxK
    gene and tetracycline resistant gene

<400> SEQUENCE: 263
gtaaataagc tgttcatatc gtgttttaaa agcagcttag        40

<210> SEQ ID NO 264
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for downstream region of braB
    gene and tetracycline resistant gene

<400> SEQUENCE: 264
cccgcttggg cttatgcccg tgtcacagaa cgcctgcgtt        40

<210> SEQ ID NO 265
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as PCR primer for downstream region of braB gene

<400> SEQUENCE: 265
aagaaagctg ggtactcgag gaagaagaaa cagaaggcgg        40

<210> SEQ ID NO 266
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of ytxK
    gene and downstream region of braB gene

<400> SEQUENCE: 266
aacgcaggcg ttctgtgaca gtgttttaaa agcagcttag        40

<210> SEQ ID NO 267
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for downstream region of braB
    gene and upstream region of ytxK gene

<400> SEQUENCE: 267
ctaagctgct tttaaaacac tgtcacagaa cgcctgcgtt        40

<210> SEQ ID NO 268
<211> LENGTH: 40
<212> TYPE: DNA
<213> ORGANISM: Artificial Sequence

```
<220> FEATURE:
<223> OTHER INFORMATION: Description of Artificial Sequence:
      Oligonucleotide as PCR primer for upstream region of sbo gene

<400> SEQUENCE: 268
aaaaagcagg ctagctcgag ccgacagccg ccccgcgcgc                                40

<210> SEQ ID NO 269
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of sbo
      gene and tetracycline resistant gene

<400> SEQUENCE: 269
gtaaataagc tgttcatatc tttcataatt gaatcctccc                                40

<210> SEQ ID NO 270
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ywhH
      gene and tetracycline resistant gene

<400> SEQUENCE: 270
cccgcttggg cttatgcccg aaaaacatcc agacatcgtc                                40

<210> SEQ ID NO 271
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ywhH
      gene

<400> SEQUENCE: 271
aagaaagctg ggtactcgag cgcagacgga caacccatgg                                40

<210> SEQ ID NO 272
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of sbo
      gene and downstream region of ywhH gene

<400> SEQUENCE: 272
gacgatgtct ggatgttttt tttcataatt gaatcctccc                                40

<210> SEQ ID NO 273
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ywhH
      gene and upstream region of sbo gene

<400> SEQUENCE: 273
gggaggattc aattatgaaa aaaaacatcc agacatcgtc                                40

<210> SEQ ID NO 274
```

-continued

```
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of pdp gene

<400> SEQUENCE: 274
ggggacaagt ttgtacaaaa aagcaggctg tactggatca attgggtgg                49

<210> SEQ ID NO 275
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of pdp
      gene and tetracycline resistant gene

<400> SEQUENCE: 275
gtaaataagc tgttcatatc ccgcggaagc gaaggcgccg                          40

<210> SEQ ID NO 276
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of rocR
      gene and tetracycline resistant gene

<400> SEQUENCE: 276
cccgcttggg cttatgcccg ccggagcagg aagcctgatc                          40

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of rocR
      gene

<400> SEQUENCE: 277
ggctgggagc ggctctggcg                                                20

<210> SEQ ID NO 278
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of pdp
      gene and
      downstream region of rocR gene

<400> SEQUENCE: 278
gatcaggctt cctgctccgg ccgcggaagc gaaggcgccg                          40

<210> SEQ ID NO 279
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of rocR
      gene and upstream region of pdp gene

<400> SEQUENCE: 279
```

```
cggcgccttc gcttccgcgg ccggagcagg aagcctgatc                           40
```

<210> SEQ ID NO 280
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yybP gene

<400> SEQUENCE: 280

```
ggggacaagt ttgtacaaaa aagcaggcta tccactttcc gccaatgac                49
```

<210> SEQ ID NO 281
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yybP
      gene and tetracycline resistant gene

<400> SEQUENCE: 281

```
gtaaataagc tgttcatatc gaaaaagcat cccgacgcgg                           40
```

<210> SEQ ID NO 282
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yyaJ gene and tetracycline resistant gene

<400> SEQUENCE: 282

```
cccgcttggg cttatgcccg aaaagtcagt gcggatctgc                           40
```

<210> SEQ ID NO 283
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yyaJ
      gene

<400> SEQUENCE: 283

```
ggggaccact ttgtacaaga aagctgggta gttgaaatca taggcgaggg               50
```

<210> SEQ ID NO 284
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yybP
      gene and downstream region of yyaJ gene

<400> SEQUENCE: 284

```
gcagatccgc actgactttt gaaaaagcat cccgacgcgg                           40
```

<210> SEQ ID NO 285
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yyaJ
      gene and upstream region of yybP gene

```
<400> SEQUENCE: 285
ccgcgtcggg atgcttttc aaaagtcagt gcggatctgc                           40

<210> SEQ ID NO 286
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yisB gene

<400> SEQUENCE: 286
atgccggtac ctggctcgag ctgtccagca ggatctaaag c                        41

<210> SEQ ID NO 287
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yisB
      gene and tetracycline resistant gene

<400> SEQUENCE: 287
gggtaactat tgccgataag ctttaatgcg atccgctcct cccttacatc               50

<210> SEQ ID NO 288
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yitD
      gene and tetracycline resistant gene

<400> SEQUENCE: 288
aaggctcgag ttccggtacc ggaaatcgat gcggctgcgg ggctctcgtc g             51

<210> SEQ ID NO 289
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yitD
      gene

<400> SEQUENCE: 289
atgccggtac ctggctcgag cggcgtcaga gcatccgccc                          40

<210> SEQ ID NO 290
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yisB
      gene and downstream region of yitD gene

<400> SEQUENCE: 290
gctgttcata tcgacctgct cgaggaattc gatccgctcc tcccttacat c             51

<210> SEQ ID NO 291
<211> LENGTH: 50
<212> TYPE: DNA
<213> ORGANISM: Artificial Sequence
<220> FEATURE:
```

<223> OTHER INFORMATION: Description of Artificial Sequence:
     Oligonucleotide as SOE-PCR primer for downstream region of
     yitD gene and upstream region of yisB gene

<400> SEQUENCE: 291
gggatcaact tgggagaga gctcgagggg cggctgcggg gctctcgtcg         50

<210> SEQ ID NO 292
<211> LENGTH: 32
<212> TYPE: DNA
<213> ORGANISM: Artificial Sequence
<220> FEATURE:
<223> OTHER INFORMATION: Description of Artificial Sequence:
     Oligonucleotide as PCR primer for upstream region of ykuS gene

<400> SEQUENCE: 292
ggcgagctcg ccgtaaaagt gaacgggacg gc         32

<210> SEQ ID NO 293
<211> LENGTH: 52
<212> TYPE: DNA
<213> ORGANISM: Artificial Sequence
<220> FEATURE:
<223> OTHER INFORMATION: Description of Artificial Sequence:
     Oligonucleotide as SOE-PCR primer for upstream region of ykuS
     gene and tetracycline resistant gene

<400> SEQUENCE: 293
gctgttcata tcgacctgct cgaggaattc gcacctccgt ttactagagt gc         52

<210> SEQ ID NO 294
<211> LENGTH: 49
<212> TYPE: DNA
<213> ORGANISM: Artificial Sequence
<220> FEATURE:
<223> OTHER INFORMATION: Description of Artificial Sequence:
     Oligonucleotide as SOE-PCR primer for downstream region of ykqB
     gene and tetracycline resistant gene

<400> SEQUENCE: 294
gggatcaact tgggagaga gctcgagggt agcagccaaa taagccgtc         49

<210> SEQ ID NO 295
<211> LENGTH: 33
<212> TYPE: DNA
<213> ORGANISM: Artificial Sequence
<220> FEATURE:
<223> OTHER INFORMATION: Description of Artificial Sequence:
     Oligonucleotide as PCR primer for downstream region of ykqB gene

<400> SEQUENCE: 295
cggggtaccc cgggcttgaa tcgccatttt cac         33

<210> SEQ ID NO 296
<211> LENGTH: 40
<212> TYPE: DNA
<213> ORGANISM: Artificial Sequence
<220> FEATURE:
<223> OTHER INFORMATION: Description of Artificial Sequence:
     Oligonucleotide as SOE-PCR primer for upstream region of ykuS
     gene and downstream region of ykqB gene

<400> SEQUENCE: 296
gacggcttat ttggctgcta acctccgttt actagagtgc         40

<210> SEQ ID NO 297
<211> LENGTH: 40
<212> TYPE: DNA

```
<213> ORGANISM: Artificial Sequence
<220> FEATURE:
<223> OTHER INFORMATION: Description of Artificial Sequence:
      Oligonucleotide as SOE-PCR primer for downstream region of
      ykqB gene and upstream region of ykuS gene

<400> SEQUENCE: 297
gcactctagt aaacggaggt tagcagccaa ataagccgtc                             40

<210> SEQ ID NO 298
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yunA gene

<400> SEQUENCE: 298
atgccggtac ctggctcgag gcttcgttta cttgttcatc                             40

<210> SEQ ID NO 299
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yunA
      gene and tetracycline resistant gene

<400> SEQUENCE: 299
gctgttcata tcgacctgct cgaggaattc gcttcccttg tcgagaaatt t                51

<210> SEQ ID NO 300
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yurT gene and tetracycline resistant gene

<400> SEQUENCE: 300
gggatcaact ttgggagaga gctcgaggga ctgttttttcc ctccttcga                  49

<210> SEQ ID NO 301
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yurT
      gene

<400> SEQUENCE: 301
atgccggtac ctggctcgag ctacaatcgt atcaaaatcg                             40

<210> SEQ ID NO 302
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yunA
      gene and downstream region of yurT gene

<400> SEQUENCE: 302
tcgaaggagg gaaaaacagt cttcccttgt cgagaaattt                             40
```

<210> SEQ ID NO 303
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yurT gene and upstream region of yunA gene

<400> SEQUENCE: 303
aaatttctcg acaagggaag actgtttttc cctccttcga                              40

<210> SEQ ID NO 304
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ybbU gene

<400> SEQUENCE: 304
ctgcaaacgc aatggaagct ctatgcg                                            27

<210> SEQ ID NO 305
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ybbU
      gene and chloramphenicol resistant gene

<400> SEQUENCE: 305
gggtaactat tgccgataag ctttaatgcg ataaaaacac ccctttagat aatcttatcc        60

<210> SEQ ID NO 306
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yceK gene and upp gene

<400> SEQUENCE: 306
aaggctcgag ttccggtacc ggaaatcgat actataatac ataatgggtg                   50

<210> SEQ ID NO 307
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yceK
      gene

<400> SEQUENCE: 307
atgccggtac ctggctcgag ggaatattcg catcggacac                              40

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ycxB gene

<400> SEQUENCE: 308
gaaacatgcg cacgtctccc                                                    20

<210> SEQ ID NO 309
<211> LENGTH: 57
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of ycxB
    gene and chloramphenicol resistant gene

<400> SEQUENCE: 309
gggtaactat tgccgataag ctttaatgcg ataaaaacag tgctgatcct tttatat      57

<210> SEQ ID NO 310
<211> LENGTH: 50
<212> TYPE: DNA
<213> ORGANISM: Artificial Sequence
<220> FEATURE:
<223> OTHER INFORMATION: Description of Artificial Sequence:
    Oligonucleotide as SOE-PCR primer for downstream region of
    ydbP gene and upp gene

<400> SEQUENCE: 310
aaggctcgag ttccggtacc ggaaatcgat atgtcacatc tccttttcaa              50

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence:
    Oligonucleotide as PCR primer for downstream region of ydbP
    gene

<400> SEQUENCE: 311
ccacaagctg ttcaatcagg                                               20

<210> SEQ ID NO 312
<211> LENGTH: 57
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of ydcL
    gene and chloramphenicol resistant gene

<400> SEQUENCE: 312
gggtaactat tgccgataag ctttaatgcg ataaaaataa gtgggcagtt tgtgggc      57

<210> SEQ ID NO 313
<211> LENGTH: 50
<212> TYPE: DNA
<213> ORGANISM: Artificial Sequence
<220> FEATURE:
<223> OTHER INFORMATION: Description of Artificial Sequence:
    Oligonucleotide as SOE-PCR primer for downstream region of
    ydhU gene and upp gene

<400> SEQUENCE: 313
aaggctcgag ttccggtacc ggaaatcgat acccgttcca cggattgccc              50

<210> SEQ ID NO 314
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as PCR primer for upstream region of yhxD gene

<400> SEQUENCE: 314
atgccggtac ctggctcgag cagcatggca agccgacggt 40

<210> SEQ ID NO 315
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yhxD
      gene and chloramphenicol resistant gene

<400> SEQUENCE: 315
gggtaactat tgccgataag ctttaatgcg tagctttatg aaaggagctg 50

<210> SEQ ID NO 316
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yhjP
      gene and upp gene

<400> SEQUENCE: 316
aaggctcgag ttccggtacc ggaaatcgat taaaagagg gttctttttt g 51

<210> SEQ ID NO 317
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yhjP
      gene

<400> SEQUENCE: 317
atgccggtac ctggctcgag tgaccaatct gatctattgg 40

<210> SEQ ID NO 318
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yisB gene

<400> SEQUENCE: 318
atgccggtac ctggctcgag ctgtccagca ggatctaaag c 41

<210> SEQ ID NO 319
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yisB
      gene and chloramphenicol resistant gene

<400> SEQUENCE: 319
gggtaactat tgccgataag ctttaatgcg atccgctcct cccttacatc 50

<210> SEQ ID NO 320
<211> LENGTH: 51
<212> TYPE: DNA
<213> ORGANISM: Artificial Sequence
<220> FEATURE:
<223> OTHER INFORMATION: Description of Artificial Sequence:

```
           Oligonucleotide as SOE-PCR primer for downstream region of yitD
           gene and upp gene

<400> SEQUENCE: 320
aaggctcgag ttccggtacc ggaaatcgat gcggctgcgg ggctctcgtc g              51

<210> SEQ ID NO 321
<211> LENGTH: 40
<212> TYPE: DNA
<213> ORGANISM: Artificial Sequence
<220> FEATURE:
<223> OTHER INFORMATION: Description of Artificial Sequence:
           Oligonucleotide as PCR primer for downstream region of yitD
           gene

<400> SEQUENCE: 321
atgccggtac ctggctcgag cggcgtcaga gcatccgccc                           40

<210> SEQ ID NO 322
<211> LENGTH: 41
<212> TYPE: DNA
<213> ORGANISM: Artificial Sequence
<220> FEATURE:
<223> OTHER INFORMATION: Description of Artificial Sequence:
           Oligonucleotide as PCR primer for upstream region of yitH gene

<400> SEQUENCE: 322
atgccggtac ctggctcgag ctgctcagta caagaacact g                         41

<210> SEQ ID NO 323
<211> LENGTH: 50
<212> TYPE: DNA
<213> ORGANISM: Artificial Sequence
<220> FEATURE:
<223> OTHER INFORMATION: Description of Artificial Sequence:
           Oligonucleotide as SOE-PCR primer for upstream region of yitH
           gene and chloramphenicol resistant gene

<400> SEQUENCE: 323
gggtaactat tgccgataag ctttaatgcg ccctcttttt tcccgaacag               50

<210> SEQ ID NO 324
<211> LENGTH: 51
<212> TYPE: DNA
<213> ORGANISM: Artificial Sequence
<220> FEATURE:
<223> OTHER INFORMATION: Description of Artificial Sequence:
           Oligonucleotide as SOE-PCR primer for downstream region of yitZ
           gene and upp gene

<400> SEQUENCE: 324
aaggctcgag ttccggtacc ggaaatcgat gcggctgaaa tgcggcaccg c              51

<210> SEQ ID NO 325
<211> LENGTH: 40
<212> TYPE: DNA
<213> ORGANISM: Artificial Sequence
<220> FEATURE:
<223> OTHER INFORMATION: Description of Artificial Sequence:
           Oligonucleotide as PCR primer for downstream region of yitZ gene

<400> SEQUENCE: 325
atgccggtac ctggctcgag gggtcacggc gatatcacag                           40

<210> SEQ ID NO 326
<211> LENGTH: 20
<212> TYPE: DNA
<213> ORGANISM: Artificial Sequence
```

```
<220> FEATURE:
<223> OTHER INFORMATION: Description of Artificial Sequence:
      Oligonucleotide as PCR primer for upstream region of oppA gene

<400> SEQUENCE: 326
caagatccgt tccgtacagc                                              20

<210> SEQ ID NO 327
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of oppA
      gene and chloramphenicol resistant gene

<400> SEQUENCE: 327
tgccgataag ctttaatgcg ccccctaata ataattttca gctcc                  45

<210> SEQ ID NO 328
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yjbK
      gene and upp gene

<400> SEQUENCE: 328
ttccggtacc ggaaatcgat gatgctcttc ctttccgccc                        40

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yjbK
      gene

<400> SEQUENCE: 329
atttcatgct cttcttcccc                                              20

<210> SEQ ID NO 330
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yjcM gene

<400> SEQUENCE: 330
ggggacaagt ttgtacaaaa aagcaggcta ccacaccgca ataaaccccc             50

<210> SEQ ID NO 331
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yjcM
      gene and chloramphenicol resistant gene

<400> SEQUENCE: 331
tgccgataag ctttaatgcg taaattgata ctaaatcgtt                        40

<210> SEQ ID NO 332
<211> LENGTH: 40
```

```
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yjgB gene and upp gene

<400> SEQUENCE: 332
ttccggtacc ggaaatcgat tccctcctaa ttgatctacc                         40

<210> SEQ ID NO 333
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yjgB
      gene

<400> SEQUENCE: 333
ggggaccact tgtacaaga aagctgggta gaatccgggc caaacgcctc               50

<210> SEQ ID NO 334
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of gid gene

<400> SEQUENCE: 334
atgccggtac ctggctcgag gcccaggatg cccacgaagc                         40

<210> SEQ ID NO 335
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of gid
      gene and chloramphenicol resistant gene

<400> SEQUENCE: 335
gggtaactat tgccgataag ctttaatgcg ctttcacatc tcctagttta              50

<210> SEQ ID NO 336
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      ylxL gene and upp gene

<400> SEQUENCE: 336
aaggctcgag ttccggtacc ggaaatcgat tgattgtcgg ataaagctgt g            51

<210> SEQ ID NO 337
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ylxL gene

<400> SEQUENCE: 337
atgccggtac ctggctcgag ccttctgctg cgatacggtc                         40
```

```
<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of spoVS gene

<400> SEQUENCE: 338
gcgaattatg gtgaagccgg                                                    20

<210> SEQ ID NO 339
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of
      spoVS gene and chloramphenicol resistant gene

<400> SEQUENCE: 339
tgccgataag ctttaatgcg ttctgctccc ccttagtttt                              40

<210> SEQ ID NO 340
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      ymzA gene and upp gene

<400> SEQUENCE: 340
ttccggtacc ggaaatcgat gcagtttttt ttcatgttat g                            41

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ymzA gene

<400> SEQUENCE: 341
ttaagagaaa ccccgccacc                                                    20

<210> SEQ ID NO 342
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yqeD gene

<400> SEQUENCE: 342
atgccggtac ctggctcgag cgggcatcct ctgtcgtctg                              40

<210> SEQ ID NO 343
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yqeD
      gene and chloramphenicol resistant gene

<400> SEQUENCE: 343
tgccgataag ctttaatgcg taacatgtct atggtcactc cc                           42
```

```
<210> SEQ ID NO 344
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yrzL gene and upp gene

<400> SEQUENCE: 344
ttccggtacc ggaaatcgat cctctttccc aaattcgc                              38

<210> SEQ ID NO 345
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yrzL gene

<400> SEQUENCE: 345
atgccggtac ctggctcgag taaacgaaaa gatctgggcg                            40

<210> SEQ ID NO 346
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yvdM gene

<400> SEQUENCE: 346
atgccggtac ctggctcgag cggctgggag aaagaccatg                            40

<210> SEQ ID NO 347
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yvdM
      gene and chloramphenicol resistant gene

<400> SEQUENCE: 347
gggtaactat tgccgataag ctttaatgcg gttgatcccc cttatatgta c               51

<210> SEQ ID NO 348
<211> LENGTH: 52
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yvcP gene and upp gene

<400> SEQUENCE: 348
aaggctcgag ttccggtacc ggaaatcgat gaataaggga gtcaattcct tg              52

<210> SEQ ID NO 349
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yvcP gene

<400> SEQUENCE: 349
atgccggtac ctggctcgag caggcaatgg gtagaaccgg                            40
```

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of dltA gene

<400> SEQUENCE: 350
ccatgggctt gcggcaccgg                                              20

<210> SEQ ID NO 351
<211> LENGTH: 61
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of dltA
      gene and chloramphenicol resistant gene

<400> SEQUENCE: 351
gggtaactat tgccgataag ctttaatgcg tcgttataaa tatatgaacc ggtattcgcg    60
g                                                                   61

<210> SEQ ID NO 352
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of rocR
      gene and upp gene

<400> SEQUENCE: 352
aaggctcgag ttccggtacc ggaaatcgat acgaataatc cggagcagga agcctgatc    59

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of rocR gene

<400> SEQUENCE: 353
ggctgggagc ggctctggcg                                              20

<210> SEQ ID NO 354
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ydcD gene

<400> SEQUENCE: 354
aaaaagcagg ctagctcgag cggaaattga cttgtccgcg                        40

<210> SEQ ID NO 355
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ydcD
      gene and tetracycline resistant gene

```
<400> SEQUENCE: 355
gtaaataagc tgttcatatc aaaaaacata cacctccacc                           40

<210> SEQ ID NO 356
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      ydcK gene and tetracycline resistant gene

<400> SEQUENCE: 356
cccgcttggg cttatgcccg aaaaggttga cgaatatggc                           40

<210> SEQ ID NO 357
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ydcK gene

<400> SEQUENCE: 357
aagaaagctg ggtactcgag ttagacattc acatgatacc                           40

<210> SEQ ID NO 358
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for tetracycline resistant
      gene and chloramphenicol resistant gene

<400> SEQUENCE: 358
tgccgataag ctttaatgcg cagtttgtac tcgcaggtgg                           40

<210> SEQ ID NO 359
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for chloramphenicol resistant
      gene and tetracycline resistant gene

<400> SEQUENCE: 359
atcctaaaac ccgcttgggc cttatcgtta gcgtgctgtc                           40

<210> SEQ ID NO 360
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ydiM
      gene and tetracycline resistant gene

<400> SEQUENCE: 360
gtaaataagc tgttcatatc aattttcacc tcacatcgct                           40

<210> SEQ ID NO 361
<211> LENGTH: 40
<212> TYPE: DNA
<213> ORGANISM: Artificial Sequence
<220> FEATURE:
<223> OTHER INFORMATION: Description of Artificial Sequence:
```

Oligonucleotide as SOE-PCR primer for downstream region of yebA gene and tetracycline resistant gene

<400> SEQUENCE: 361
cccgcttggg cttatgcccg agattcttcg gcgctatgga          40

<210> SEQ ID NO 362
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yeeK
      gene and tetracycline resistant gene

<400> SEQUENCE: 362
gtaaataagc tgttcatatc atttactctc tccttcacat          40

<210> SEQ ID NO 363
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yesX
      gene and tetracycline resistant gene

<400> SEQUENCE: 363
cccgcttggg cttatgcccg gaggactaag ggataagacg          40

<210> SEQ ID NO 364
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of cspB
      gene and tetracycline resistant gene

<400> SEQUENCE: 364
gtaaataagc tgttcatatc aaattgatat gaaaaactgc          40

<210> SEQ ID NO 365
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yhcT
      gene and tetracycline resistant gene

<400> SEQUENCE: 365
cccgcttggg cttatgcccg gttaaatggc tccttttcga          40

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yhdP gene

<400> SEQUENCE: 366
cggcagttta tgcagagggc          20

<210> SEQ ID NO 367
<211> LENGTH: 43
<212> TYPE: DNA

```
<213> ORGANISM: Artificial Sequence
<220> FEATURE:
<223> OTHER INFORMATION: Description of Artificial Sequence:
      Oligonucleotide as SOE-PCR primer for upstream region of yhdP
      gene and tetracycline resistant gene

<400> SEQUENCE: 367
gtaaataagc tgttcatatc taagaaaagc accttgtata ggg                43

<210> SEQ ID NO 368
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yhaL
      gene and tetracycline resistant gene

<400> SEQUENCE: 368
cccgcttggg cttatgcccg aaaaagctgt gcggctcaat g                  41

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yhaL gene

<400> SEQUENCE: 369
gaaacgatta ggcgctagtg                                          20

<210> SEQ ID NO 370
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yjqB gene

<400> SEQUENCE: 370
ggggacaagt ttgtacaaaa aagcaggcta caaacggtcc gggaaaccgc         50

<210> SEQ ID NO 371
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yjqB
      gene and tetracycline resistant gene

<400> SEQUENCE: 371
gtaaataagc tgttcatatc cttgaacgcc cccctttacc                    40

<210> SEQ ID NO 372
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of htrA
      gene and tetracycline resistant gene

<400> SEQUENCE: 372
cccgcttggg cttatgcccg catgttcact ccgtttctct                    40

<210> SEQ ID NO 373
```

```
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of htrA gene

<400> SEQUENCE: 373
ggggaccact tgtacaaga aagctgggta gtcatgataa gccgtccgcg                50

<210> SEQ ID NO 374
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ykuS gene

<400> SEQUENCE: 374
ggcgagctcg ccgtaaaagt gaacgggacg gc                                  32

<210> SEQ ID NO 375
<211> LENGTH: 52
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ykuS
      gene and tetracycline resistant gene

<400> SEQUENCE: 375
gctgttcata tcgacctgct cgaggaattc gcacctccgt ttactagagt gc            52

<210> SEQ ID NO 376
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      ykqB gene and tetracycline resistant gene

<400> SEQUENCE: 376
gggatcaact ttgggagaga gctcgagggt agcagccaaa taagccgtc                49

<210> SEQ ID NO 377
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ykqB gene

<400> SEQUENCE: 377
cggggtaccc cgggcttgaa tcgccatttt cac                                 33

<210> SEQ ID NO 378
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 378
ggcgagctcg cccattgcta ctggttctcg tc                                  32

<210> SEQ ID NO 379
```

<210> SEQ ID NO 379
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of slp gene

<400> SEQUENCE: 379
gctgttcata tcgacctgct cgaggaattc gcagccctcg ctcaaagcgg g          51

<210> SEQ ID NO 380
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      ylaM gene and tetracycline resistant gene

<400> SEQUENCE: 380
gggatcaact ttgggagaga gctcgagggt aatttatgtc atatgctta            49

<210> SEQ ID NO 381
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ylaM gene

<400> SEQUENCE: 381
cggggtaccc cgctcccgtt aacagatggt cg                              32

<210> SEQ ID NO 382
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ctaA gene

<400> SEQUENCE: 382
ggcgagctcg ccggcaggag ccgattacag tc                              32

<210> SEQ ID NO 383
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ctaA
      gene and tetracycline resistant gene

<400> SEQUENCE: 383
gctgttcata tcgacctgct cgaggaattc gcaagaccaa agccttaggc g          51

<210> SEQ ID NO 384
<211> LENGTH: 49
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ylbE
      gene and tetracycline resistant gene

<400> SEQUENCE: 384
gggatcaact ttgggagaga gctcgagggt aaaaggcccc gaagaaggg            49

```
<210> SEQ ID NO 385
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ylbE gene

<400> SEQUENCE: 385
cggggtaccc cggatgttgt tgccaaccgc gg                              32

<210> SEQ ID NO 386
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yncM
      gene and tetracycline resistant gene

<400> SEQUENCE: 386
gtaaataagc tgttcatatc acgaagcagc aaaaagccgc                      40

<210> SEQ ID NO 387
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of fosB
      gene and tetracycline resistant gene

<400> SEQUENCE: 387
cccgcttggg cttatgcccg caaccatatt tcatataagg                      40

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yoxC gene

<400> SEQUENCE: 388
tctctcttgc tctgtcatcg                                            20

<210> SEQ ID NO 389
<211> LENGTH: 43
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yoxC
      gene and tetracycline resistant gene

<400> SEQUENCE: 389
gtaaataagc tgttcatatc atgttcactc cttttcttat gtc                  43

<210> SEQ ID NO 390
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yocS
      gene and tetracycline resistant gene

<400> SEQUENCE: 390
cccgcttggg cttatgcccg atatgcatca aaagggtac                       40
```

<210> SEQ ID NO 391
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yocS gene

<400> SEQUENCE: 391
ggtgactatg tagaacaggg tg                                              22

<210> SEQ ID NO 392
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yojO gene

<400> SEQUENCE: 392
aaaaagcagg ctagctcgag tgtgccgctc ttgtgctgcc                           40

<210> SEQ ID NO 393
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yojO
      gene and tetracycline resistant gene

<400> SEQUENCE: 393
gtaaataagc tgttcatatc taatcctatg cttttggcg                            40

<210> SEQ ID NO 394
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yozE
      gene and tetracycline resistant gene

<400> SEQUENCE: 394
cccgcttggg cttatgcccg gggtttcccc tcctgatgtc                           40

<210> SEQ ID NO 395
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yozE gene

<400> SEQUENCE: 395
aagaaagctg ggtactcgag caggcggtga tgggctgctc                           40

<210> SEQ ID NO 396
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of cgeE gene

<400> SEQUENCE: 396
aaaaagcagg ctagctcgag ctcataatca cacctgaccc                           40

<210> SEQ ID NO 397
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of cgeE
    gene and tetracycline resistant gene

<400> SEQUENCE: 397
gtaaataagc tgttcatatc aataggcgtt tgcacaaacc                40

<210> SEQ ID NO 398
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for downstream region of ypmQ
    gene and tetracycline resistant gene

<400> SEQUENCE: 398
cccgcttggg cttatgcccg gacatccatc ctttccagcc                40

<210> SEQ ID NO 399
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as PCR primer for downstream region of ypmQ gene

<400> SEQUENCE: 399
aagaaagctg ggtactcgag ggccttctct ctggggtagg                40

<210> SEQ ID NO 400
<211> LENGTH: 50
<212> TYPE: DNA
<213> ORGANISM: Artificial Sequence
<220> FEATURE:
<223> OTHER INFORMATION: Description of Artificial Sequence:
    Oligonucleotide as PCR primer for upstream region of ypzC gene

<400> SEQUENCE: 400
ggggacaagt ttgtacaaaa aagcaggcta tcctggatgg tgtattcctc        50

<210> SEQ ID NO 401
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of ypzC
    gene and tetracycline resistant gene

<400> SEQUENCE: 401
gtaaataagc tgttcatatc actgcccgta acctcatgct                40

<210> SEQ ID NO 402
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for downstream region of drm
    gene and tetracycline resistant gene

<400> SEQUENCE: 402

```
cccgcttggg cttatgcccg caggcatctt gaaagcctcc                      40
```

<210> SEQ ID NO 403
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of drm gene

<400> SEQUENCE: 403

```
ggggaccact ttgtacaaga aagctgggta attatgctat gatatgggtg           50
```

<210> SEQ ID NO 404
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yqxK gene

<400> SEQUENCE: 404

```
ggggacaagt ttgtacaaaa aagcaggcta gggcatcaaa catttcgggc           50
```

<210> SEQ ID NO 405
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yqxK
      gene and tetracycline resistant gene

<400> SEQUENCE: 405

```
gtaaataagc tgttcatatc gctaaagatt aactcagttc                      40
```

<210> SEQ ID NO 406
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yqjP
      gene and tetracycline resistant gene

<400> SEQUENCE: 406

```
cccgcttggg cttatgcccg cctttcgctc cttgtcttca                      40
```

<210> SEQ ID NO 407
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yqjP gene

<400> SEQUENCE: 407

```
ggggaccact ttgtacaaga aagctgggta ctctctaagg cggcaccggc           50
```

<210> SEQ ID NO 408
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of zwf gene

<400> SEQUENCE: 408

```
gggggacaagt tgtacaaaaa aagcaggcta gatgtaattt cggtctcccg          50
```

<210> SEQ ID NO 409
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of zwf
      gene and tetracycline resistant gene

<400> SEQUENCE: 409

```
gtaaataagc tgttcatatc aaagtacctc actttattcg                     40
```

<210> SEQ ID NO 410
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yqzF gene and tetracycline resistant gene

<400> SEQUENCE: 410

```
cccgcttggg cttatgcccg cgcaatcaag tcagcccgcg                     40
```

<210> SEQ ID NO 411
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yqzF gene

<400> SEQUENCE: 411

```
ggggaccact tgtacaaga aagctgggta atgtgagttt ccctcggcc             50
```

<210> SEQ ID NO 412
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yqgZ gene

<400> SEQUENCE: 412

```
aaaaagcagg ctagctcgag tagacacctt gggcggctgg                     40
```

<210> SEQ ID NO 413
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yqgZ
      gene and tetracycline resistant gene

<400> SEQUENCE: 413

```
gtaaataagc tgttcatatc tgaaaaaccg aagatccgct                     40
```

<210> SEQ ID NO 414
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      yqgN gene and tetracycline resistant gene

```
<400> SEQUENCE: 414
cccgcttggg cttatgcccg ctctcatccc cctcggaata g                    41

<210> SEQ ID NO 415
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yqgN gene

<400> SEQUENCE: 415
aagaaagctg ggtactcgag ctttgatctg attcatgccc                      40

<210> SEQ ID NO 416
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yrzF gene

<400> SEQUENCE: 416
aaaaagcagg ctagctcgag tatcaatgga gtatgtaccc                      40

<210> SEQ ID NO 417
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yrzF
      gene and tetracycline resistant gene

<400> SEQUENCE: 417
gtaaataagc tgttcatatc ttcattcacc ttctttgctc                      40

<210> SEQ ID NO 418
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yrxA
      gene and tetracycline resistant gene

<400> SEQUENCE: 418
cccgcttggg cttatgcccg aagccctcga agaagccggc                      40

<210> SEQ ID NO 419
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yrxA gene

<400> SEQUENCE: 419
aagaaagctg ggtactcgag agatgccgtt caaaaggtcg                      40

<210> SEQ ID NO 420
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ytrI gene
```

```
<400> SEQUENCE: 420
aaaaagcagg ctagctcgag ttttgcattt cttcgagtgg                            40

<210> SEQ ID NO 421
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ytrI
      gene and tetracycline resistant gene

<400> SEQUENCE: 421
gtaaataagc tgttcatatc gaagaaagat gctcctgggt                            40

<210> SEQ ID NO 422
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ytlI
      gene and tetracycline resistant gene

<400> SEQUENCE: 422
cccgcttggg cttatgcccg ctgaaaaaat aaaaaccacc                            40

<210> SEQ ID NO 423
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ytlI gene

<400> SEQUENCE: 423
aagaaagctg ggtactcgag ttattcaaag cggttattcc                            40

<210> SEQ ID NO 424
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ytxK
      gene and tetracycline resistant gene

<400> SEQUENCE: 424
gtaaataagc tgttcatatc gtgttttaaa agcagcttag                            40

<210> SEQ ID NO 425
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of braB
      gene and tetracycline resistant gene

<400> SEQUENCE: 425
cccgcttggg cttatgcccg tgtcacagaa cgcctgcgtt                            40

<210> SEQ ID NO 426
<211> LENGTH: 40
<212> TYPE: DNA
<213> ORGANISM: Artificial Sequence
<220> FEATURE:
```

<223> OTHER INFORMATION: Description of Artificial Sequence:
      Oligonucleotide as PCR primer for upstream region of ytzH gene

<400> SEQUENCE: 426
aaaaagcagg ctagctcgag tgatgatatt gagcccatcc         40

<210> SEQ ID NO 427
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ytzH
      gene and tetracycline resistant gene

<400> SEQUENCE: 427
gtaaataagc tgttcatatc aacggtacac atcccttcag         40

<210> SEQ ID NO 428
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of ytbQ
      gene and tetracycline resistant gene

<400> SEQUENCE: 428
cccgcttggg cttatgcccg cagctcctca taatttgccg         40

<210> SEQ ID NO 429
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ytbQ
      gene

<400> SEQUENCE: 429
aagaaagctg ggtactcgag tcaggacctt tcacatgtgc         40

<210> SEQ ID NO 430
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of ytvB gene

<400> SEQUENCE: 430
aaaaagcagg ctagctcgag atgcgtgttc cggggcaagg         40

<210> SEQ ID NO 431
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of ytvB
      gene and tetracycline resistant gene

<400> SEQUENCE: 431
gtaaataagc tgttcatatc ttgtcctcaa tctccgcccg         40

<210> SEQ ID NO 432
<211> LENGTH: 43
<212> TYPE: DNA

```
<213> ORGANISM: Artificial Sequence
<220> FEATURE:
<223> OTHER INFORMATION: Description of Artificial Sequence:
      Oligonucleotide as SOE-PCR primer for downstream region of
      ytoA gene and tetracycline resistant gene

<400> SEQUENCE: 432
cccgcttggg cttatgcccg gacctgcttc gtcttacttt acc                43

<210> SEQ ID NO 433
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ytoA gene

<400> SEQUENCE: 433
aagaaagctg ggtactcgag tggatttggg cgttatcggc                    40

<210> SEQ ID NO 434
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of pckA gene

<400> SEQUENCE: 434
atgccggtac ctggctcgag gccgtcaggg cgaaggtacg                    40

<210> SEQ ID NO 435
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of
      pckA gene and tetracycline resistant gene

<400> SEQUENCE: 435
gtaaataagc tgttcatatc atgaaacctt cctttatcgt                    40

<210> SEQ ID NO 436
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of mntA
      gene and tetracycline resistant gene

<400> SEQUENCE: 436
cccgcttggg cttatgcccg atttctcctc ctctttgcca                    40

<210> SEQ ID NO 437
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of mntA gene

<400> SEQUENCE: 437
atgccggtac ctggctcgag ggcattgggc ggaacaagag                    40

<210> SEQ ID NO 438
<211> LENGTH: 40
```

-continued

<212> TYPE: DNA
<213> ORGANISM: Artificial Sequence
<220> FEATURE:
<223> OTHER INFORMATION: Description of Artificial Sequence:
      Oligonucleotide as PCR primer for upstream region of yueJ gene

<400> SEQUENCE: 438
atgccggtac ctggctcgag gcaacgagtt tataaactgc                                    40

<210> SEQ ID NO 439
<211> LENGTH: 41
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yueJ
      gene and tetracycline resistant gene

<400> SEQUENCE: 439
gtaaataagc tgttcatatc taaggaaggg gaaaaacagt g                                  41

<210> SEQ ID NO 440
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yukJ
      gene and tetracycline resistant gene

<400> SEQUENCE: 440
cccgcttggg cttatgcccg taagatagaa aaagagactg                                    40

<210> SEQ ID NO 441
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of yukJ gene

<400> SEQUENCE: 441
atgccggtac ctggctcgag ctgtgttcat ccggcggggg                                    40

<210> SEQ ID NO 442
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yunA
      gene and tetracycline resistant gene

<400> SEQUENCE: 442
gtaaataagc tgttcatatc cttcccttgt cgagaaattt                                    40

<210> SEQ ID NO 443
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yurT
      gene and tetracycline resistant gene

<400> SEQUENCE: 443
cccgcttggg cttatgcccg actgttttc cctccttcga                                     40

<210> SEQ ID NO 444
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as PCR primer for upstream region of yurZ gene

<400> SEQUENCE: 444
aaaaagcagg ctagctcgag ccggatttta caacgcggcc                40

<210> SEQ ID NO 445
<211> LENGTH: 43
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of yurZ
    gene and tetracycline resistant gene

<400> SEQUENCE: 445
gtaaataagc tgttcatatc gagaaggaat attccgaaaa acc            43

<210> SEQ ID NO 446
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for downstream region of yuxN
    gene and tetracycline resistant gene

<400> SEQUENCE: 446
cccgcttggg cttatgcccg cgccaaagat gcggaacagc                40

<210> SEQ ID NO 447
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as PCR primer for downstream region of yuxN gene

<400> SEQUENCE: 447
aagaaagctg ggtactcgag gtacgatgac aacttcccgc                40

<210> SEQ ID NO 448
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as PCR primer for upstream region of smpB gene

<400> SEQUENCE: 448
aaaaagcagg ctagctcgag ggaaatggac agctgcatcg                40

<210> SEQ ID NO 449
<211> LENGTH: 40
<212> TYPE: DNA
<213> ORGANISM: Artificial Sequence
<220> FEATURE:
<223> OTHER INFORMATION: Description of Artificial Sequence:
    Oligonucleotide as SOE-PCR primer for upstream region of smpB
    gene and tetracycline resistant gene

<400> SEQUENCE: 449
gtaaataagc tgttcatatc aaggcatagt gcttgattcg                40

<210> SEQ ID NO 450
<211> LENGTH: 40
<212> TYPE: DNA
<213> ORGANISM: Artificial Sequence
<220> FEATURE:
<223> OTHER INFORMATION: Description of Artificial Sequence:
     Oligonucleotide as SOE-PCR primer for downstream region of
     yvbK gene and tetracycline resistant gene

<400> SEQUENCE: 450
cccgcttggg cttatgcccg aaagcataaa aaagccgccg                          40

<210> SEQ ID NO 451
<211> LENGTH: 40
<212> TYPE: DNA
<213> ORGANISM: Artificial Sequence
<220> FEATURE:
<223> OTHER INFORMATION: Description of Artificial Sequence:
     Oligonucleotide as PCR primer for downstream region of yvbK gene

<400> SEQUENCE: 451
aagaaagctg ggtactcgag ggttgagctt cgtgacggcg                          40

<210> SEQ ID NO 452
<211> LENGTH: 40
<212> TYPE: DNA
<213> ORGANISM: Artificial Sequence
<220> FEATURE:
<223> OTHER INFORMATION: Description of Artificial Sequence:
     Oligonucleotide as SOE-PCR primer for upstream region of sbo
     gene and tetracycline resistant gene

<400> SEQUENCE: 452
gtaaataagc tgttcatatc tttcataatt gaatcctccc                          40

<210> SEQ ID NO 453
<211> LENGTH: 40
<212> TYPE: DNA
<213> ORGANISM: Artificial Sequence
<220> FEATURE:
<223> OTHER INFORMATION: Description of Artificial Sequence:
     Oligonucleotide as SOE-PCR primer for downstream region of
     ywhH gene and tetracycline resistant gene

<400> SEQUENCE: 453
cccgcttggg cttatgcccg aaaaacatcc agacatcgtc                          40

<210> SEQ ID NO 454
<211> LENGTH: 50
<212> TYPE: DNA
<213> ORGANISM: Artificial Sequence
<220> FEATURE:
<223> OTHER INFORMATION: Description of Artificial Sequence:
     Oligonucleotide as PCR primer for upstream region of ywcB gene

<400> SEQUENCE: 454
ggggacaagt ttgtacaaaa aagcaggcta atttcactga ctcccgctcc              50

<210> SEQ ID NO 455
<211> LENGTH: 40
<212> TYPE: DNA
<213> ORGANISM: Artificial Sequence
<220> FEATURE:
<223> OTHER INFORMATION: Description of Artificial Sequence:
     Oligonucleotide as SOE-PCR primer for upstream region of ywcB
     gene and tetracycline resistant gene

<400> SEQUENCE: 455
gtaaataagc tgttcatatc ggctttcctc cttttattcg        40

<210> SEQ ID NO 456
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of
      ywaE gene and tetracycline resistant gene

<400> SEQUENCE: 456
cccgcttggg cttatgcccg gctttgacgg gaatccagta        40

<210> SEQ ID NO 457
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of ywaE gene

<400> SEQUENCE: 457
ggggaccact tgtacaaga aagctgggta cttctgctgc tttctctccg        50

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide as PCR primer for upstream region of dltA gene

<400> SEQUENCE: 458
ccatgggctt gcggcaccgg        20

<210> SEQ ID NO 459
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of dltA
      gene and tetracycline resistant gene

<400> SEQUENCE: 459
gtaaataagc tgttcatatc atatgaaccg gtattcgcgg        40

<210> SEQ ID NO 460
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of hutM
      gene and tetracycline resistant gene

<400> SEQUENCE: 460
cccgcttggg cttatgcccg gcacaccccg ctcagcatgg        40

<210> SEQ ID NO 461
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide as PCR primer for downstream region of hutM gene

<400> SEQUENCE: 461

```
ggggaccact tgtacaaga aagctgggcc aggatatgag tgaccgtg         48

<210> SEQ ID NO 462
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for upstream region of yybP
      gene and tetracycline resistant gene

<400> SEQUENCE: 462
gtaaataagc tgttcatatc gaaaaagcat cccgacgcgg               40

<210> SEQ ID NO 463
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide as SOE-PCR primer for downstream region of yyaJ
      gene and tetracycline resistant gene

<400> SEQUENCE: 463
cccgcttggg cttatgcccg aaaagtcagt gcggatctgc               40
```